United States Patent [19]
Pan

[11] Patent Number: 6,043,086
[45] Date of Patent: Mar. 28, 2000

[54] NEUROTACTIN AND USES THEREFOR

[75] Inventor: Yang Pan, Brookline, Mass.

[73] Assignee: Millenium BioTherapeutics, Inc., Cambridge, Mass.

[21] Appl. No.: 09/143,470

[22] Filed: Aug. 28, 1998

Related U.S. Application Data

[63] Continuation-in-part of application No. 08/991,426, Dec. 16, 1997, which is a continuation-in-part of application No. 08/851,160, May 5, 1997, which is a continuation-in-part of application No. 08/643,798, May 7, 1996.

[51] Int. Cl.⁷ .............................. C12N 5/06; C07K 16/24; C07K 16/25
[52] U.S. Cl. .................... 435/335; 435/336; 530/388.23; 530/388.24
[58] Field of Search ..................................... 435/325, 335, 435/336; 530/388.23, 388.24, 868

[56] References Cited

FOREIGN PATENT DOCUMENTS

WO 95/17092  6/1995  WIPO .
WO 95/32282  11/1995  WIPO .

OTHER PUBLICATIONS

Baggiolini et al., "CC chemokines in allergic inflammation" Immun. Today 15:(3)127–133, 1994.

Barthalay et al., "Drosophila neurotactin mediates heterophilic cell Adhesion" EMBO Journal 9:(11)3603–3609, 1990.

Burkly et al., "T–Cell tolerance by clonal anergy in transgenic mice with nonlymphoid expression: . . . " Nature 342:564–566, 1989.

Cocket et al., "The use of engineered E1A genes to transactivate the hCMV–MIE promoter in permanent CHO cell lines" Nucl. Acids Res. 19:319–325, 1991.

Kelner et al., "Lymphotactin: A cytokine that represents a new class of cemokine" Science 266:1395–1399, 1994.

Massague et al., "Membrane–Anchored Growth Factors" Annu. Rev. Biochem. 62:515–41, 1993.

Owens et al., "Inflammatory cytokines in the brain: does the CNS shape immune responses?" Immun. Today 15:(12)566–571, 1994.

Pan et al., "Neurotactin, a membrane–anchored chemokine upregulated in brain inflammation" Nature 387: 611–617, 1997.

Rowland, L., "Blood–Brain Barrier, Cerbrospinal Fluid, Brain Edema, and Hydrocephalus" Appendix, *Brain Fluids and Their Disorders*, pp. 837–844.

Santiago et al., "Characterization and gene cloning of neurotactin, a Drosophila transmembrane protein related to cholinesterases" EMBO Journal 9:3593–3601, 1990.

*Primary Examiner*—David Saunders
*Assistant Examiner*—F. Pierre VanderVegt
*Attorney, Agent, or Firm*—Fish & Richardson P.C.

[57] ABSTRACT

The present invention relates to the identification and characterization of a novel, membrane-anchored chemokine, neurotactin. Sequence analysis of neurotactin reveals that, while it includes an amino terminal domain which resembles that of other chemokines, it has an overall structure which distinguishes it from all presently identified chemokines. Neurotactin is highly expressed in normal mammalian brain. Inhibitors of neurotactin expression or activity can be used to treat inflammation.

4 Claims, 10 Drawing Sheets

```
GTCGACCCAC GCGTCCGGCC GAATTCCTGC ACTCCAGCC ATG GCT CCC TCG CCG        54
                                            Met Ala Pro Ser Pro
                                            1               5

CTC GCG TGG CTG CTG CGC CTG GCC GCG TTC TTC CAT TTG TGT ACT CTG       102
Leu Ala Trp Leu Leu Arg Leu Ala Ala Phe Phe His Leu Cys Thr Leu
            10                  15                  20

CTG CCG GGT CAG CAC CTC GGC ATG ACG AAA TGC GAA ATC ATG TGC GAC       150
Leu Pro Gly Gln His Leu Gly Met Thr Lys Cys Glu Ile Met Cys Asp
                25                  30                  35

AAG ATG ACC TCA CGA ATC CCA GTG GCT TTG CTC ATC CGC TAT CAG CTA       198
Lys Met Thr Ser Arg Ile Pro Val Ala Leu Leu Ile Arg Tyr Gln Leu
        40                  45                  50

AAC CAG GAG TCC TGC GGC AAG CGT GCC ATT GTC CTG GAG ACG ACA CAG       246
Asn Gln Glu Ser Cys Gly Lys Arg Ala Ile Val Leu Glu Thr Thr Gln
55                  60                  65

CAC AGA CGC TTC TGT GCT GAC CCG AAG GAG AAA TGG GTC CAA GAC GCC       294
His Arg Arg Phe Cys Ala Asp Pro Lys Glu Lys Trp Val Gln Asp Ala
70                  75                  80                  85

ATG AAG CAT CTG GAT CAC CAG GCT GCT GCC CTC ACT AAA AAT GGT GGC       342
Met Lys His Leu Asp His Gln Ala Ala Ala Leu Thr Lys Asn Gly Gly
                90                  95                  100

AAG TTT GAG AAG CGG GTG GAC AAT GTG ACA CCT GGG ATC ACC TTG GCC       390
Lys Phe Glu Lys Arg Val Asp Asn Val Thr Pro Gly Ile Thr Leu Ala
            105                 110                 115

ACT AGG GGA CTG TCC CCA TCT GCC CTG ACA AAG CCT GAA TCC GCC ACA       438
Thr Arg Gly Leu Ser Pro Ser Ala Leu Thr Lys Pro Glu Ser Ala Thr
        120                 125                 130

TTG GAA GAC CTT GCT TTG GAA CTG ACT ACT ATT TCC CAG GAG GCC AGG       486
Leu Glu Asp Leu Ala Leu Glu Leu Thr Thr Ile Ser Gln Glu Ala Arg
135                 140                 145

GGG ACC ATG GGG ACT TCC CAA GAG CCA CCG GCA GCA GTG ACC GGA TCA       534
Gly Thr Met Gly Thr Ser Gln Glu Pro Pro Ala Ala Val Thr Gly Ser
150                 155                 160                 165

TCT CTC TCA ACT TCC GAG GCA CAG GAT GCA GGG CTT ACG GCT AAG CCT       582
Ser Leu Ser Thr Ser Glu Ala Gln Asp Ala Gly Leu Thr Ala Lys Pro
                170                 175                 180

CAG AGC ATT GGA AGT TTT GAG GCG GCT GAC ATC TCC ACC ACC GTT TGG       630
Gln Ser Ile Gly Ser Phe Glu Ala Ala Asp Ile Ser Thr Thr Val Trp
            185                 190                 195

CCG AGT CCT GCT GTC TAC CAA TCT GGA TCT AGC TCC TGG GCT GAG GAA       678
Pro Ser Pro Ala Val Tyr Gln Ser Gly Ser Ser Ser Trp Ala Glu Glu
        200                 205                 210

AAA GCT ACT GAG TCC CCC TCC ACT ACA GCC CCA TCT CCT CAG GTG TCC       726
Lys Ala Thr Glu Ser Pro Ser Thr Thr Ala Pro Ser Pro Gln Val Ser
215                 220                 225

ACT ACT TCA CCT TCA ACC CCA GAG GAA AAT GTT GGG TCC GAA GGC CAA       774
Thr Thr Ser Pro Ser Thr Pro Glu Glu Asn Val Gly Ser Glu Gly Gln
230                 235                 240                 245

CCC CCA TGG GTC CAG GGA CAG GAC CTC AGT CCA GAG AAG TCT CTA GGG       822
Pro Pro Trp Val Gln Gly Gln Asp Leu Ser Pro Glu Lys Ser Leu Gly
                250                 255                 260
```

FIG. 1A

```
TCT GAG GAG ATA AAC CCA GTT CAT ACT GAT AAT TTC CAG GAG AGG GGG      870
Ser Glu Glu Ile Asn Pro Val His Thr Asp Asn Phe Gln Glu Arg Gly
            265                 270                 275

CCT GGC AAC ACA GTC CAC CCC TCA GTG GCT CCC ATC TCC TCT GAA GAG      918
Pro Gly Asn Thr Val His Pro Ser Val Ala Pro Ile Ser Ser Glu Glu
        280                 285                 290

ACC CCC AGC CCA GAG CTG GTG GCC TCG GGC AGC CAG GCT CCT AAG ATA      966
Thr Pro Ser Pro Glu Leu Val Ala Ser Gly Ser Gln Ala Pro Lys Ile
    295                 300                 305

GAG GAA CCC ATC CAT GCC ACT GCA GAT CCC CAG AAA CTG AGT GTG CTT     1014
Glu Glu Pro Ile His Ala Thr Ala Asp Pro Gln Lys Leu Ser Val Leu
310                 315                 320                 325

ATC ACT CCT GTC CCC GAC ACC CAG GCA GCC ACA AGG AGG CAG GCA GTG     1062
Ile Thr Pro Val Pro Asp Thr Gln Ala Ala Thr Arg Arg Gln Ala Val
                330                 335                 340

GGG CTA CTG GCT TTC CTT GGT CTT CTT TTC TGC CTA GGG GTG GCC ATG     1110
Gly Leu Leu Ala Phe Leu Gly Leu Leu Phe Cys Leu Gly Val Ala Met
            345                 350                 355

TTT GCT TAC CAG AGC CTT CAG GGC TGT CCC CGC AAA ATG GCG GGG GAA     1158
Phe Ala Tyr Gln Ser Leu Gln Gly Cys Pro Arg Lys Met Ala Gly Glu
        360                 365                 370

ATG GTA GAA GGC CTC CGC TAC GTC CCC CGT AGC TGT GGC AGT AAC TCA     1206
Met Val Glu Gly Leu Arg Tyr Val Pro Arg Ser Cys Gly Ser Asn Ser
    375                 380                 385

TAC GTC CTG GTG CCA GTG TGAGCTGCTT GCCTGCCTGC CTGTGTCCAG AGTGTGAT   1262
Tyr Val Leu Val Pro Val
390                 395

TCGGACAGCT GTCTGGGGAC CCCCCCCAT CCTCATACCC ACCTTCATCC ACGCTGGGGA   1322

AATGGGAATG GAGAAGCTGG ACCCTCCAGG GGCTGTGGGC TCCATCCAAT CCCCCCTCCC   1382

CCGAGGGGTG GCCCCGGAGG CCACCCTAGA CCACTATTCA CTTATCAGAG ACAGAGCAGG   1442

TGACCTTCCA GCTCCTCTAT ATTTGAAAGA ATCCTCTGCT GCTGGCTGGT TAGAGGGGCC   1502

CTTGACACCC CAACTCCAGT GAACAATTAT TTATTGGATT CCCAGCCCCT GCGACGACAC   1562

CTGTTTCCCG CGCGCACCGT GGTCCGCCCA TATCACAAGC AGCAGGCCAG GCCTATCTGC   1622

CTGTCCCCCT GACCTCCTTG TGTCTCCTGG CTTTGCTGCA GTCGCCAGCC CTTCTCCTCC   1682

CCGGCCAGCT GCGGTGCTAT CTGCCCTATG TCTCCCTCTA TCCCCTGTAC AGAGCGCACC   1742

ACCATCACCA TCAAAAAAAA AAAAAAAAA AAGGGCGGCC GC                       1784
SEQ ID NO:1
```

FIG. 1B

```
AAGCTTGGCA CGAGGGCACT GAGCTCTGCC GCCTGGCTCT AGCCGCCTGC CTGGCCCCCG        60

CCGGGACTCT TGCCCACCCT CAGCC ATG GCT CCG ATA TCT CTG TCG TGG CTG        112
                            Met Ala Pro Ile Ser Leu Ser Trp Leu
                             1               5

CTC CGC TTG GCC ACC TTC TGC CAT CTG ACT GTC CTG CTG GCT GGA CAG        160
Leu Arg Leu Ala Thr Phe Cys His Leu Thr Val Leu Leu Ala Gly Gln
 10              15              20              25

CAC CAC GGT GTG ACG AAA TGC AAC ATC ACG TGC AGC AAG ATG ACA TCA        208
His His Gly Val Thr Lys Cys Asn Ile Thr Cys Ser Lys Met Thr Ser
             30              35              40

AAG ATA CCT GTA GCT TTG CTC ATC CAC TAT CAA CAG AAC CAG GCA TCA        256
Lys Ile Pro Val Ala Leu Leu Ile His Tyr Gln Gln Asn Gln Ala Ser
             45              50              55

TGC GGC AAA CGC GCA ATC ATC TTG GAG ACG AGA CAG CAC AGG CTG TTC        304
Cys Gly Lys Arg Ala Ile Ile Leu Glu Thr Arg Gln His Arg Leu Phe
         60              65              70

TGT GCC GAC CCG AAG GAG CAA TGG GTC AAG GAC GCG ATG CAG CAT CTG        352
Cys Ala Asp Pro Lys Glu Gln Trp Val Lys Asp Ala Met Gln His Leu
     75              80              85

GAC CGC CAG GCT GCT GCC CTA ACT CGA AAT GGC GGC ACC TTC GAG AAG        400
Asp Arg Gln Ala Ala Ala Leu Thr Arg Asn Gly Gly Thr Phe Glu Lys
 90              95             100             105

CAG ATC GGC GAG GTG AAG CCC AGG ACC ACC CCT GCC GCC GGG GGA ATG        448
Gln Ile Gly Glu Val Lys Pro Arg Thr Thr Pro Ala Ala Gly Gly Met
            110             115             120

GAC GAG TCT GTG GTC CTG GAG CCC GAA GCC ACA GGC GAA AGC AGT AGC        496
Asp Glu Ser Val Val Leu Glu Pro Glu Ala Thr Gly Glu Ser Ser Ser
            125             130             135

CTG GAG CCG ACT CCT TCT TCC CAG GAA GCA CAG AGG GCC CTG GGG ACC        544
Leu Glu Pro Thr Pro Ser Ser Gln Glu Ala Gln Arg Ala Leu Gly Thr
        140             145             150

TCC CCA GAG CTG CCG ACG GGC GTG ACT GGT TCC TCA GGG ACC AGG CTC        592
Ser Pro Glu Leu Pro Thr Gly Val Thr Gly Ser Ser Gly Thr Arg Leu
155             160             165

CCC CCG ACG CCA AAG GCT CAG GAT GGA GGG CCT GTG GGC ACG GAG CTT        640
Pro Pro Thr Pro Lys Ala Gln Asp Gly Gly Pro Val Gly Thr Glu Leu
170             175             180             185

TTC CGA GTG CCT CCC GTC TCC ACT GCC GCC ACG TGG CAG AGT TCT GCT        688
Phe Arg Val Pro Pro Val Ser Thr Ala Ala Thr Trp Gln Ser Ser Ala
            190             195             200

CCC CAC CAA CCT GGG CCC AGC CTC TGG GCT GAG GCA AAG ACC TCT GAG        736
Pro His Gln Pro Gly Pro Ser Leu Trp Ala Glu Ala Lys Thr Ser Glu
            205             210             215

GCC CCG TCC ACC CAG GAC CCC TCC ACC CAG GCC TCC ACT GCG TCC TCC        784
Ala Pro Ser Thr Gln Asp Pro Ser Thr Gln Ala Ser Thr Ala Ser Ser
        220             225             230

CCA GCC CCA GAG GAG AAT GCT CCG TCT GAA GGC CAG CGT GTG TGG GGT        832
Pro Ala Pro Glu Glu Asn Ala Pro Ser Glu Gly Gln Arg Val Trp Gly
235             240             245
```

FIG. 2A

```
CAG GGA CAG AGC CCC AGG CCA GAG AAC TCT CTG GAG CGG GAG GAG ATG        880
Gln Gly Gln Ser Pro Arg Pro Glu Asn Ser Leu Glu Arg Glu Glu Met
250                 255                 260                 265

GGT CCC GTG CCA GCG CAC ACG GAT GCC TTC CAG GAC TGG GGG CCT GGC        928
Gly Pro Val Pro Ala His Thr Asp Ala Phe Gln Asp Trp Gly Pro Gly
                270                 275                 280

AGC ATG GCC CAC GTC TCT GTG GTC CCT GTC TCC TCA GAA GGG ACC CCC        976
Ser Met Ala His Val Ser Val Val Pro Val Ser Ser Glu Gly Thr Pro
            285                 290                 295

AGC AGG GAG CCA GTG GCT TCA GGC AGC TGG ACC CCT AAG GCT GAG GAA        1024
Ser Arg Glu Pro Val Ala Ser Gly Ser Trp Thr Pro Lys Ala Glu Glu
        300                 305                 310

CCC ATC CAT GCC ACC ATG GAC CCC CAG AGG CTG GGC GTC CTT ATC ACT        1072
Pro Ile His Ala Thr Met Asp Pro Gln Arg Leu Gly Val Leu Ile Thr
    315                 320                 325

CCT GTC CCT GAC GCC CAG GCT GCC ACC CGG AGG CAG GCG GTG GGG CTG        1120
Pro Val Pro Asp Ala Gln Ala Ala Thr Arg Arg Gln Ala Val Gly Leu
330                 335                 340                 345

CTG GCC TTC CTT GGC CTC CTC TTC TGC CTG GGG GTG GCC ATG TTC ACC        1168
Leu Ala Phe Leu Gly Leu Leu Phe Cys Leu Gly Val Ala Met Phe Thr
                350                 355                 360

TAC CAG AGC CTC CAG GGC TGC CCT CGA AAG ATG GCA GGA GAG ATG GCG        1216
Tyr Gln Ser Leu Gln Gly Cys Pro Arg Lys Met Ala Gly Glu Met Ala
            365                 370                 375

GAG GGC CTT CGC TAC ATC CCC CGG AGC TGT GGT AGT AAT TCA TAT GTC        1264
Glu Gly Leu Arg Tyr Ile Pro Arg Ser Cys Gly Ser Asn Ser Tyr Val
        380                 385                 390

CTG GTG CCC GTG T GAACTCCTCT GGCCTGTGTC TAGTTGTTTG ATTCAGACAG          1317
Leu Val Pro Val
    395

CTGCCTGGGA TCCCTCATCC TCATACCCAC CCCCACCCAA GGGCCTGGCC TGAGCTGGGA      1377

TGATTGGAGG GGGGAGGTGG GATCCTCCAG GTGCACAAGC TCCAAGCTCC CAGGCATTCC      1437

CCAGGAGGCC AGCCTTGACC ATTCTCCACC TTCAGGGAC AGAGGGGGTG GCCTCCCAAC       1497

TCACCCCAGC CCCAAAACTC TCCTCTGCTG CTGGCTGGTT AGAGGTTCCC TTTGACGCCA      1557

TCCCAGCCCC AATGAACAAT TATTTATTAA ATGCCCAGCC CCTTCTGAAA AAAAAAAAA      1617

AAAAAAAAAA AAAAAAAAAA AAAATTCCTG CGGCCGC                               1654

SEQ ID NO:3
```

FIG. 2B

```
  1 MAPISLSWLLRLATFCHLTVLLAGQHHGVTKCNITCSKMTSKIPVALLIH  50
    |||  | |||||| | ||  ||:|||  :|||:|  | |||| :|||||||:
  1 MAPSFLAWLLRLAAFFHLCTLLPGQHLGMTKCEIMCDKMTSRIPVALLIR  50

51 YQQNQASCGKRAIILETRQHRLFCADPKEQWVKDAMQHLDRQAAALTRNG 100
    || ||.|||||||:|||  ||| |||||||.||.|||.|||:|||||| ||
 51 YQLNQESCGKRAIVLETTQHRRFCADPKEKWVQDAMKHLDHQAAALTKNG 100

101 GTFEKQIGEVKPRTTPAAGGMDESVVLEPE..ATGESSSLEPTPSSQEAQR 149
    |.|||.::: |.| .| | . |:..|.: .|| ||  |. || |: ||||.
101 GKFEKRVDNVTPGITLATRGLSPSALTKPESATLEDLALELTTISQEARG 150

150 ALGTSPELFTGVTGSSGTRLPPTPKAQDGG....PVGTELFRVPPVSTAA 195
    .:|||.|  |.:|||||     .|..|||:|    |  |:.:  |  :|| .
151 TMGTSQEPPAAVTGSS....LSTSEAQDAGLTAKPQSIGSFEAADIST.T 195

196 TWQSSAPHQPGPSLWAEAKTSEAPSTQDPSTQASTASSPAPEENAPSEGQ 245
    .|.|.|..|.|.| |||.|.. |.|||  .||.|.||.|. . |||| .||||
196 VWPSPAVYQSGSSSWAEEKATESPSTTAPSPQVSTTSPSTPEENVGSEGQ 245

246 RVWGQGQSPRPENSLEREEMGPVPAHTDAFQDWGPGSMAHVSVVPVSSEG 295
    ..|.|||. .||.||:.||:..|| |||.||::|||. .|.||.|:|||:
246 PPWVGQDLSPEKSLGSEEINPV...HTDNFQERGPGNTVHPSVAPISSEE 293

296 TPSREPVASGSWTPKAEEPIHATMDPQRLGVLITPVPDAQAATRRQAVGL 345
    |||.| |||||| .|| ||||||||  |||:|:|||||||||.|||||||||
294 TPSPELVASGSQAPKIEEPIHATADPQKLSVLITPVPDTQAATRRQAVGL 343

346 LAFLGLLFCLGVAMFTYQSLQGCPRKMAGEMAEGLRYIPRSCGSNSYVLV 395
    |||||||||||||||| |||||||||||||||| ||||||:|||||||||||
344 LAFLGLLFCLGVAMFAYQSLQGCPRKMAGEMVEGLRYVPRSCGSNSYVLV 393

NEUROTACTIN AND USES THEREFOR

This application is a continuation-in-part of U.S. Ser. No. 08/991,426, filed Dec. 16, 1997, now allowed which is a continuation-in-part of U.S. Ser. No. 08/851,160, filed May 5, 1997, still pending which is a continuation-in-part of U.S. Ser. No. 08/643,798 filed May 7, 1996, still pending. The contents of these applications are incorporated herein by reference in their entirety.

BACKGROUND OF THE INVENTION

This invention relates to a new chemokine, neurotactin, and methods of preparing and using neurotactin.

Chemokines are proteins involved in the activation and chemotaxis of leukocytes. They are believed to be important mediators of inflammation (Baggiolini et al., *Immunology Today* 15:127, 1994). Chemokines have been divided into three families based on the number and arrangement of their cysteines and disulfide bonds. Proteins in the C-X-C family and the C-C family have two disulfide bonds. Proteins in the third family, which is represented by a molecule called lymphotactin, have only one disulfide bond.

In chemokines of the C-X-C family, one amino acid separates the first two cysteines. Chemokines in this family are thought to be involved in the chemotaxis of neutrophils, induction of changes in cell shape, transient increase of intracellular calcium, granule exocytosis, and respiratory burst. Interleukin-8 (IL-8), neutrophil activating protein-2 (NAP-2) and granulocyte chemotactic protein (GCP) belong to this class. All known C-X-C chemokines have been mapped to human chromosome 4 and mouse chromosome 5.

In chemokines of the C-C family, the first two cysteines are adjacent to one another. Members of this family are chemotactic for monocytes, but not neutrophils. Recent studies have shown that they are capable of activating basophils and eosinophils. Proteins belonging to the C-C class of chemokines include monocyte chemotactic proteins 1, 2, and 3 (MCP-1, MCP-2, and MCP-3), RANTES, and macrophage inflammatory proteins α and β (MIP-1α and MIP-1β). Recently, three additional C-C chemokines, MIP-3, MIP-4, and MIP-1γ, have been described (see PCT Publication No. WO 95/17092). All known C-C chemokines have been mapped to human chromosome 17 and mouse chromosome 11.

An example of a third class of chemokine has also been identified. This chemokine, lymphotactin, was isolated from progenitor T lymphocytes. Lymphotactin is chemotactic to lymphocytes (Kelner et al., *Science* 266:1395, 1994). Unlike the chemokines of the C-C and C-X-C families in which two disulfide bonds stabilize the protein, lymphotactin has only one disulfide bond. Lymphotactin was mapped to human and mouse chromosome 1.

A variety of cell types are involved in the various inflammatory states. For example, acute infiltrates found after bacterial infection are mainly neutrophilic, while mononuclear cells predominate after infection by an intracellular pathogen. Basophils and eosinophils dominate in both immediate-type allergic response and autoimmune diseases. Increased understanding of the regulation of these various cell types by chemokines will facilitate the development of more effective therapies for disorders related to inflammation.

Brain inflammation is only partially understood. It appears that the brain regulates its own immune response rather than being an immunological privileged organ (Trevor et al., *Immunology Today* 15:566, 1994). Inflammatory cytokine production in the brain is initiated by infiltrating T cells but longer term inflammation is dependent on CNS resident cells, such as microglial cells.

SUMMARY OF THE INVENTION

The present invention relates to the identification and characterization of neurotactin, a novel membrane-anchored chemokine. Sequence analysis of neurotactin reveals that, while it includes an amino terminal domain which resembles that of other chemokines, it has an overall structure which distinguishes it from all presently identified chemokines.

The expression pattern of neurotactin is unusual for a chemokine in that it is highly expressed in normal mammalian brain. Similar to other chemokines, neurotactin is upregulated in bone marrow stromal cells, endothelial cells, and fibroblasts which have been treated with lipopolysaccharide (LPS) and phorbal myristate acid (PMA), both of which are activators.

A murine form of neurotactin described herein encodes a protein of 395 amino acids (FIGS. 1A–1B). This murine form of the protein (SEQ ID NO:2) begins with an approximately 21 amino acid long signal sequence followed by an apparent extracellular domain of approximately 318 amino acids extending from about amino acid 22 to about amino acid 339; a transmembrane domain of approximately 21 amino acids extending from about amino acid 340 to about amino acid 360; and a cytoplasmic domain of approximately 35 amino acids extending from about amino acid 361 to amino acid 395.

A human form of neurotactin described herein encodes a protein of 397 amino acids (FIGS. 2A–2B). This human form of the protein (SEQ ID NO:4) begins with an approximately 21 amino acid long signal sequence followed by an apparent extracellular domain of approximately 321 amino acids extending from about amino acid 22 to about amino acid 341; a transmembrane domain of approximately 22 amino acids extending from about amino acid 342 to about amino acid 362; and a cytoplasmic domain of approximately 35 amino acids extending from about amino acid 363 to amino acid 397.

Within the extracellular domain of both the murine form of neurotactin described herein and the human form of neurotactin described herein is a chemokine-like domain which extends from about amino acid 22 to about amino acid 92.

Overall, the human form of neurotactin described herein is 67% identical at the amino acid level to the murine form of neurotactin described herein. The highest homology between the two forms is found in transmembrane and cytoplasmic domains, suggesting that both domains have important functional roles. High homology between the two forms is also found in the chemokine-like amino terminal region.

The invention features an isolated nucleic acid which encodes a neurotactin polypeptide. The nucleic acid can have the nucleotide sequence of, e.g., FIGS. 1A–1B, SEQ ID NO:1 (murine), or FIGS. 2A–2B, SEQ ID NO:3 (human). Preferably, the neurotactin polypeptide includes an amino acid sequence substantially identical to the amino acid sequence shown in FIGS. 1A–1B (SEQ ID NO:2) or the amino acid sequence shown in FIGS. 2A–2B (SEQ ID NO4). Also considered within the scope of the invention are isolated nucleic acids that hybridize under stringent conditions to nucleic acids having the nucleotide sequence of, e.g., FIGS. 1A–1B, SEQ ID NO:1 (murine), or FIGS. 2A–2B, SEQ ID NO3 (human). Substantially pure polypeptides encoded by nucleic acids that hybridize under stringent conditions to, e.g., SEQ ID NO:1 or SEQ ID NO:3, are also featured in the invention.

Preferred neurotactin polypeptides have a sequence which is substantially identical to that of a naturally occurring neurotactin polypeptide, e.g., the mature form of human neurotactin described herein.

By "isolated nucleic acid" is meant DNA that is not immediately contiguous with both of the coding sequences with which it is immediately contiguous (one on the 5' end and one on the 3' end) in the naturally occurring genome of the organism from which it is derived. Thus, a recombinant nucleic acid could include some or all of the 5' non-coding (e.,g., promoter) sequences which are immediately contiguous to the coding sequence. The term therefore includes, for example, a recombinant DNA which is incorporated into a vector; into an autonomously replicating plasmid or virus, such as a retrovirus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "mature human neurotactin" is meant a polypeptide having the sequence shown in FIGS. 2A–2B (SEQ ID NO:4) from about amino acid 22 to amino acid 397. Polypeptides substantially identical to mature human neurotactin have an amino acid sequence which is at least 85%, preferably 90%, and most preferably 95% or even 99% identical to the amino acid sequence of the neurotactin polypeptide of FIGS. 2A–2B (SEQ ID NO:4).

By "substantially identical" is meant a polypeptide or nucleic acid having a sequence that is at least 85%, preferably 90%, and more preferably 95% or more identical to the sequence of the reference amino acid or nucleic acid sequence. For polypeptides, the length of the reference polypeptide sequence will generally be at least 16 amino acids, preferably at least 20 amino acids, more preferably at least 25 amino acids, and most preferably 35 amino acids. For nucleic acids, the length of the reference nucleic acid sequence will generally be at least 50 nucleotides, preferably at least 60 nucleotides, more preferably at least 75 nucleotides, and most preferably at least 110 nucleotides.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). Preferably, the two sequences are the same length.

The determination of percent homology between two sequences can be accomplished using a mathematical algorithm. A preferred, non-limiting example of a mathematical algorithm utilized for the comparison of two sequences is the algorithm of Karlin and Altschul, Proc. Natl. Acad. Sci. USA 87:2264–2268, 1990, modified as in Karlin and Altschul, Proc. Natl. Acad. Sci. USA 90:5873–5877, 1993. Such an algorithm is incorporated into the NBLAST and XBLAST programs of Altschul et al., J. Mol. Biol. 215:403–410, 1990. BLAST nucleotide searches can be performed with the NBLAST program, score=100, wordlength=12 to obtain nucleotide sequences homologous to neurotactin nucleic acid molecules of the invention. BLAST protein searches can be performed with the XBLAST program, score=50, wordlength=3 to obtain amino acid sequences homologous to neurotactin protein molecules of the invention. To obtain gapped alignments for comparison purposes, Gapped BLAST can be utilized as described in Altschul et al., Nucleic Acids Res. 25: 3389–3402, 1997. Alternatively, PSI-Blast can be used to perform an iterated search which detects distant relationships between molecules. Id. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) CABIOS 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

Polypeptides corresponding to one or more domains of neurotactin, e.g., the extracellular domain or the chemokine-like domain (about amino acid 22 to about amino acid 92 of a form of neurotactin described herein), are also within the scope of the invention. Preferred polypeptides are those which are soluble under normal physiological conditions. Also within the invention are soluble fusion proteins in which a full-length form of neurotactin or a portion (e.g., one or more domains) thereof is fused to an unrelated protein or polypeptide (i.e., a fusion partner) to create a fusion protein.

The invention also features isolated nucleic acid sequences that encode a portion of neurotactin, including but not limited to the extracellular domain, the transmembrane domain, the cytoplasmic domain, the chemokine-like domain, and various functional domains of neurotactin. Also within the invention are nucleic acids encoding polypeptides corresponding to one or more domains of neurotactin, e.g., the extracellular domain or the chemokine-like domain. Preferred nucleic acids encode polypeptides that are soluble under normal physiological conditions. Also within the invention are nucleic acids encoding fusion proteins in which a portion of neurotactin or a portion (e.g., one or more domains) thereof is fused to an unrelated protein or polypeptide (i.e., a fusion partner) to create a fusion protein.

Encompassed within the invention are nucleic acid sequences that encode forms of neurotactin in which sequences are altered or deleted.

The nucleic acids of the invention include nucleic acids encoding mature neurotactin as well as neurotactin polypeptides fused to a polypeptide which facilitates secretion, e.g., a secretory sequence. Such a fused protein is typically referred to as a preprotein. The secretory sequence can be removed by the host cell to form the mature protein. Also within the invention are nucleic acids that encode mature neurotactin fused to a polypeptide sequence to produce an inactive proprotein. Proproteins can be converted into the active form of the protein by removal of the inactivating sequence.

The invention also encompasses nucleic acids that hybridize under stringent conditions to a nucleic acid encoding a neurotactin polypeptide. Examples of stringent conditions include: 1) hybridization at 50° C. in Church buffer (7% SDS, 0.5% NaHPO$_4$, 1 mM EDTA, 1% BSA) and washing at 50° C. in 2× SSC; and 2) hybridization in 6× sodium chloride/sodium citrate (SSC) at about 45° C., followed by one or more washes in 0.2×SSC, 0.1% SDS at 50–65° C. Other stringent conditions are known to those skilled in the art and can be found in *Current Protocols in Molecular Biology*, John Wiley & Sons, N.Y. (1989), 6.3.1–6.3.6. The hybridizing portion of the hybridizing nucleic acids are preferably 20, 30, 50, or 70 bases long. Preferably, the hybridizing portion of the hybridizing nucleic acid is 95% or even 98% identical to the sequence of a portion of a nucleic acid encoding a neurotactin polypeptide. Hybridizing nucleic acids of the type described above can be used as a cloning probe, a primer (e.g., a PCR primer), or a diagnostic probe. Preferred hybridizing nucleic acids encode a polypeptide having some or all of the biological activities possessed by naturally-occurring neurotactin. Hybridizing nucleic acids can be splice variants encoded by one of the neurotactin genes described herein. Thus, they may encode a protein which is shorter or longer than the various forms of neurotactin described herein. Hybridizing nucleic acids may also encode proteins which are related to neurotactin (e.g. proteins encoded by genes which include a portion having a relatively high degree of identity to a neurotactin gene described herein).

The invention also features substantially pure neurotactin polypeptides. Among the polypeptides encompassed within the invention are those corresponding to the extracellular domain, the transmembrane domain, the cytoplasmic domain, and various functional domains of neurotactin including the chemokine-like domain which corresponds to a domain extending from about amino acid 22 to about amino acid 92 of the form of murine neurotactin described herein and to a domain extending from about amino acid 22 to about amino acid 92 of the form of human neurotactin described herein.

The invention also encompasses polypeptides and nucleic acids whose sequences are substantially identical to that of a form of neurotactin described herein. By "protein" and "polypeptide" is meant any chain of amino acids, regardless of length or post-translational modification (e.g., glycosylation or phosphorylation).

By "substantially pure" is meant a preparation which is at least 60% by weight (dry weight) the compound of interest, i.e., a neurotactin polypeptide. Preferably the preparation is at least 75%, more preferably at least 90%, and most preferably at least 99%, by weight the compound of interest. Purity can be measured by any appropriate standard method, e.g., column chromatography, polyacrylamide gel electrophoresis, or HPLC analysis.

The term "nucleic acid" encompasses both RNA and DNA, including cDNA, genomic DNA, and synthetic (e.g., chemically synthesized) DNA. The nucleic acid may be double-stranded or single-stranded. Where single-stranded, the nucleic acid may be the sense strand or the antisense strand.

The polypeptides of the invention include, but are not limited to: recombinant polypeptides, natural polypeptides, and synthetic polypeptides as well as polypeptides which are preproteins or proproteins.

The polypeptides of the invention can be expressed fused to another polypeptide, e.g., a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

The invention features transformed cells harboring a nucleic acid encompassed by the invention. The invention also features vectors which include a nucleic acid of the invention which is properly positioned for expression. For example, the vector can be an expression vector, and can include one or more regulatory elements. Regulatory elements that can influence the expression of the nucleic acid inserted into the vector, such as regulatory elements that direct tissue-specific expression, are well known to those of skill in the art. Examples of regulatory elements include the cytomegalovirus hCMV immediate early gene, the early promoter of SV40 adenovirus, the late promoter of SV40 adenovirus, the lac system, the trp system, the TAC system, the TRC system, the major operator and promoter regions of phage lambda, the control regions of fd coat protein, the promoter for 3-phosphoglycerate kinase, the promoters of acid phosphatase, and the promoters of the yeast α-mating factors. The vector can be a plasmid, or a virus, such as a retrovirus.

By "transformed cell" is meant a cell into which (or into an ancestor of which) has been introduced, by means of recombinant DNA techniques, a DNA molecule encoding (as used herein) neurotactin polypeptide.

By "positioned for expression" is meant that the selected DNA molecule is positioned adjacent to one or more sequence elements which direct transcription and/or translation of the sequence such that the sequence elements can control transcription and/or translation of the selected DNA (i.e., the selected DNA is operably associated with the sequence elements). Such operably associated elements can be used to facilitate the production of a neurotactin polypeptide.

The invention also features purified antibodies which specifically bind a neurotactin protein or polypeptide.

By "purified antibody" is meant an antibody which is at least 60%, by dry weight, free from the proteins and naturally-occurring organic molecules with which it is naturally associated. Preferably, the preparation is at least 75%, more preferably at least 90%, and most preferably at least 99%, by dry weight, antibody.

By "specifically binds" is meant an antibody that recognizes and binds to a particular antigen, e.g., neurotactin polypeptide, but which does not substantially recognize and bind to other molecules in a sample, e.g., a biological sample. In a preferred embodiment the sample is one which naturally includes neurotactin.

The invention also features antagonists and agonists of neurotactin. Antagonists can inhibit one or more of the functions of neurotactin. Suitable antagonists can include large or small molecules (e.g., organic molecules), antibodies to neurotactin, and neurotactin polypeptides which compete with a native form of neurotactin. Agonists of neurotactin will enhance or facilitate one or more of the functions of neurotactin. Suitable agonists can include, for example, large or small molecules (e.g., organic molecules), and antibodies to neurotactin.

Also within the invention are nucleic acid molecules which can be used to interfere with neurotactin expression, e.g., antisense molecules and ribozymes.

The invention features substantially pure neurotactin polypeptides. In various preferred embodiments the polypeptide is soluble, the polypeptide includes the chemokine-like domain of neurotactin, the polypeptide includes the extracellular domain of neurotactin, the polypeptide is at least 80% identical to the amino acid sequence from amino acid 22 to amino acid 92 in SEQ ID NO:4, the polypeptide is at least 90% identical to the amino acid sequence from amino acid 22 to amino acid 92 in SEQ ID NO:4, the polypeptide has an amino acid sequence identical to the amino acid sequence from amino acid 22 to amino acid 92 in SEQ ID NO:4, the polypeptide is at least 80% identical to the amino acid sequence from amino acid 22 to amino acid 397 in SEQ ID NO:4, the polypeptide is at least 90% identical to the amino acid sequence from amino acid 22 to amino acid 397 in SEQ ID NO:4, and the polypeptide has an amino acid sequence identical to the amino acid sequence from amino acid 22 to amino acid 397 in SEQ ID NO:4.

The invention also features a substantially pure polypeptide which includes a first portion and a second portion; the first portion includes a neurotactin polypeptide (e.g., the extracellular or chemokine-like domain of neucotactin) and the second portion includes an immunoglabulin constant region. Such polypeptides can be prepared by expressing a gene fusion encoding a neurotactin polypeptide-encoding DNA sequence fused in frame to a DNA sequence encoding, for example, the hinge, CH2 region, and CH3 region of human IgG1. A DNA sequence encoding human IgG heavy chain is described by Ellison et al. (*Nucl. Acids Res.* 10:4071, 1982).

The invention also features a substantially pure polypeptide which includes a first portion and a second portion; the first portion includes a neurotactin polypeptide and the second portion includes a detectable marker. Examples of detectable markers include β-lactamase, chloramphenicol acetyltransferase (CAT), alkaline phosphatase (AP), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), β-galactosidase, and xanthine guanine phosphoribosyl-transferase (XGPRT).

In another aspect the invention features a recombinant nucleic acid encoding a neurotactin polypeptide. In various preferred embodiments the nucleic acid encodes a soluble neurotactin polypeptide, the nucleic acid encodes the chemokine-like-like domain of neurotactin, and the nucleic acid encodes the extracellular domain of neurotactin.

The invention also features a nucleic acid encoding a hybrid polypeptide. This hybrid polypeptide includes a first portion and a second portion; the first portion includes a neurotactin polypeptide; the second portion comprising an immunoglobulin constant region.

The invention also features a cell which harbors a recombinant nucleic acid encoding a neurotactin polypeptide; a vector which includes a nucleic acid encoding a neurotactin polypeptide.

In another aspect, the invention features an antibody which selectively binds to a neurotactin polypeptide. In a preferred embodiment, the antibody is a monoclonal antibody.

The invention also features a pharmaceutical composition which includes a neurotactin polypeptide.

The invention features a method for detecting inflammation. This method includes: (a) obtaining a biological sample; (b) contacting the sample with an antibody which selectively binds a neurotactin polypeptide; and (c) determining the amount of the antibody selectively bound to said biological sample as a measure of inflammation.

In another aspect, the invention features a method for treating a patient who has a disorder (e.g. an inflammatory disorder) associated with abnormal expression or activity of a polypeptide having the amino acid sequence of SEQ ID NO:4. The method includes administering to the patient an inhibitor of neurotactin expression or activity. Preferably, the inhibitor is an antibody which selectively binds to neurotactin (preferably an extracellular portion of neurotactin or the chemokine-like domain of neurotactin) and inhibits neurotactin activity. Thus, the invention includes a method for treating a patient suffering from an unwanted inflammatory process, comprising administering to the patient an antibody which selectively binds a polypeptide having the sequence of SEQ ID NO:4. In a preferred embodiment the unwanted inflammatory process is an inflammation of the brain (e.g., inflammation associated with viral meningitis, inflammation associated with bacterial meningitis; inflammation associated with viral encephalitis; inflammation associated with multiple sclerosis; inflammation associated with severe head trauma; inflammation associated with stroke; inflammation associated with a neurodegenerative disorder; inflammation associated with HIV encephalopathy; inflammation associated with post seizure brain injury; inflammation associated with a primary brain tumor; inflammation associated with a Th1-related disorder; or inflammation associated with Lupus-associated cerebritis). The antibody administered is preferably a human antibody and the dosage is 1–100 mg/kg, more preferably 10–20 mg/kg.

The invention also features a method for inhibiting proliferation of progenitor cells in a patient. The method includes administering to the patient a substantially pure neurotactin polypeptide capable of inhibiting progenitor cell proliferation. The invention also includes a method of suppressing proliferation of an actively dividing myeloid cell. This method includes contacting the cell with an effective amount of a neurotactin polypeptide that is capable of inhibiting proliferation of myeloid cells.

The invention also features an adjunctive method for use with chemotherapy or radiation therapy in a patient. The method includes: administering an effective amount of a neurotactin polypeptide to the patient, and administering chemotherapy or radiation therapy to the patient in conjunction with administration of the neurotactin polypeptide. By "adjunctive method" means administration before, during, or after chemotherapy or radiation therapy.

The invention also features a method of treating a hyperproliferative myeloid disease in a patient. The method includes administering to the patient an effective amount of a neurotactin polypeptide. In preferred embodiments, the disease is chronic myelogenous leukemia, polycythemia vera, and a hypermegakaryocytopoietic disorder.

The invention features a substantially pure protein which functionally interacts with neurotactin and a nucleic acid encoding a protein which functionally interacts with neurotactin.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed descriptions, and from the claims.

BRIEF DESCRIPTION OF THE DRAWINGS

FIGS. 1A–1B depict the nucleotide (SEQ ID NO:1) and amino acid (SEQ ID NO:2) sequences of a form of murine neurotactin, including a putative signal sequence. Amino acids R337 and R338 define a potential enzyme cleavage site.

FIGS. 2A–2B depict the nucleotide (SEQ ID NO:3) and amino acid (SEQ ID NO:4) sequence of a form of human neurotactin, including a putative signal sequence. Amino acids R339 and R340 define a potential enzyme cleavage site.

FIG. 3 is a sequence alignment of full-length human (SEQ ID NO:4) and mouse (SEQ ID NO:2) neurotactin. In this alignment, a vertical line between the two aligned sequences indicates an exact match, a single dot between the two aligned sequences indicates a conservative substitution, a pair of dots between the two aligned sequences indicates a very conservative substitution, and a series of dots within a sequence indicates a gap introduced to maximize alignment.

DETAILED DESCRIPTION

Neurotactin, described for the first time herein, is a novel chemokine that plays a role in inflammation, particularly inflammation of the brain.

Neurotactin mediates chemotaxis of specific cell types and is likely to induce release of inflammatory mediators. As a consequence, neurotactin may enhance leukocyte infiltration through the endothelial cell wall and have effect on microglial cells. Neurotactin, like certain other proteins, may have a functional secreted form as well as a functional membrane-bound form.

While it is clear that neurotactin is a chemokine, it is also clear that neurotactin is an example of a novel class of chemokines.

First, neurotactin has three spacer amino acids between the first two cysteines (CXXXC), compared with none or one in the CC or CXC chemokines, respectively.

Second, neurotactin has an unusual expression pattern. As with other chemokines, neurotactin can be upregulated in bone marrow stromal cells, endothelial cells, and fibroblasts when treated with LPS and PMA. However, unlike other chemokines, neurotactin is highly expressed in normal brain, which suggests involvement in brain function.

Third, the length of the predicted neurotactin protein, 395 amino acids for the murine form described herein and 397 amino acids for the human form described herein, is considerably longer than the majority of known chemokines. Further, the portions of murine and human neurotactin after the first 92 amino acids of the mature protein do not bear significant resemblance to any presently known, sequenced protein. The first 92 amino acids of both the murine and human forms of neurotactin described herein have greater than 40% identity to murine MCP-1 and human MCP-1, respectively.

Fourth, the neurotactin gene maps to a different chromosomal location than the three known classes of mouse chemokines. It is located on human chromosome 16 and mouse chromosome 8. The murine C-C, C-X-C, and lymphotactin chemokines have been mapped to chromosomes 11, 5, and 1 respectively.

Taken together, these facts demonstrate that neurotactin represents a new class of chemokine, referred to herein as the δ class.

Figure 4:
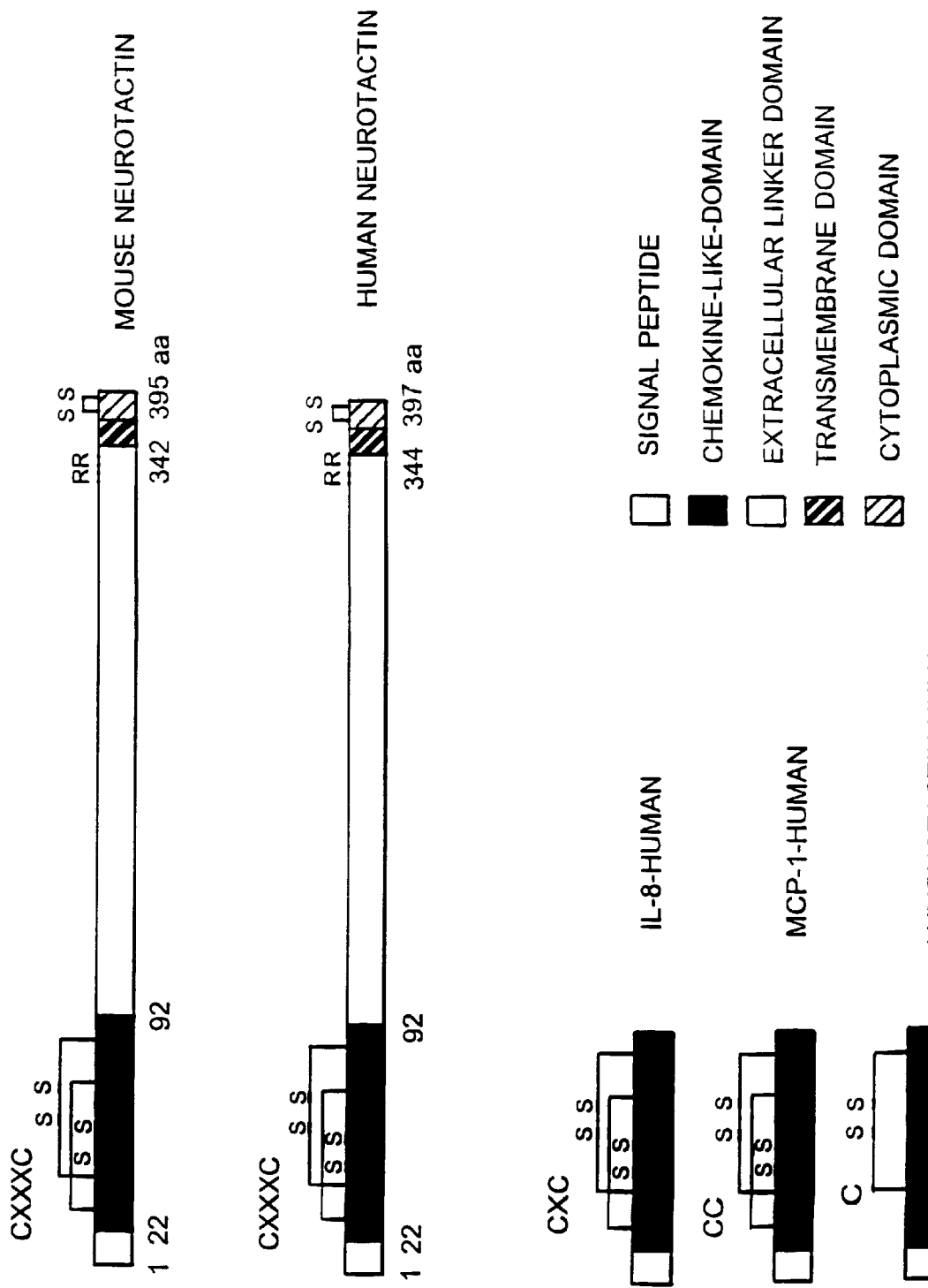
FIG. 4 is a comparison of the primary structure of neurotactin to that of known chemokine subfamilies.

FIG. 4 shows the primary structure of the murine and human forms of neurotactin, as well as the primary structures of human IL-8, human MCP-1, and human lymphotactin. Also shown in this figure are comparisons between the proteins. As can be seen from this figure, the primary structure of the first 92 amino acids of all five proteins are similar, whereas the two forms of neurotactin include an extracellular linker domain, a transmembrane domain, and a cytoplasmic domain not found in the other chemokines. The extracellular linker domain is the domain between the chemotactin-like domain and the transmembrane domain. The extracellular domain extends from about amino acid 93 to about amino acid 341 of the human form of neurotactin described herein and from about amino acid 93 to about amino acid 339 or the murine form of neurotactin described herein.

The two neighboring arginines adjacent to the transmembrane region (amino acids 339 and 340 in the human form; amino acids 337 and 338 in the murine form) provide for the possibility of processing these proteins with proteolytic enzymes to detach them from the cell membrane.

Neurotactin Proteins and Polypeptides

Neurotactin proteins and polypeptides and neurotactin fusion proteins can be prepared for a wide range of uses including, but not limited to, generation of antibodies, preparation of reagents or diagnostic assays, identification of other molecules involved in inflammation (particularly brain inflammation), preparation of reagents for use in screening assays for inflammatory modulators, and preparation of therapeutic agents for treatment of inflammation-related disorders.

FIGS. 1A–1B show the amino acid sequence of a form of murine neurotactin (SEQ ID NO:2). The domain from amino acid 1 to about amino acid 21 forms a putative signal sequence. This putative signal sequence is followed by an extracellular domain of approximately 318 amino acids extending from about amino acid 22 to about amino acid 339; a transmembrane domain of approximately 21 amino acids extending from about amino acid 340 to about amino acid 360; and a cytoplasmic domain of approximately 35 amino acids extending from about amino acid 361 to amino acid 395.

FIGS. 2A–2B show the amino acid sequence of a form of human neurotactin (SEQ ID NO: 4). The domain from amino acid 1 to about amino acid 21 forms a putative signal sequence. This putative signal sequence is followed by an extracellular domain of approximately 321 amino acids extending from about amino acid 22 to about amino acid 341; a transmembrane domain of approximately 22 amino acids extending from about amino acid 342 to about amino acid 362; and a cytoplasmic domain of approximately 35 amino acids extending from about amino acid 363 to amino acid 397.

The invention encompasses, but is not limited to, neurotactin proteins and polypeptides that are functionally related to neurotactin encoded by the nucleotide sequence of FIGS. 1A–1B (murine, SEQ ID NO:1) or FIGS. 2A–2B (human, SEQ ID NO:3). Functionally related proteins and polypeptides include any protein or polypeptide sharing a functional characteristic with neurotactin, e.g., the ability to affect proliferation, differentiation, survival, apoptosis, or activation of a cell type whose proliferation, differentiation, survival, apoptosis, or activation is affected by neurotactin. Such functionally related neurotactin polypeptides include, but are not limited to, additions or substitutions of amino acid residues within the amino acid sequence encoded by the neurotactin sequences described herein which result in a silent change, thus producing a functionally equivalent gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to neurotactin DNA (using random mutagenesis techniques well known to those skilled in the art) and the resulting mutant neurotactin proteins can be tested for activity, site-directed mutations of the neurotactin coding sequence can be engineered (using site-directed mutagenesis techniques well known to those skilled in the art) to generate mutant neurotactins with increased function, e.g., greater stimulation of cell proliferation, or decreased function, e.g., lesser stimulation of cell proliferation.

To design functionally related and functionally variant neurotactin polypeptides, it is useful to distinguish between conserved positions and variable positions. FIG. 4 shows an alignment between the amino acid sequence of human neurotactin and murine neurotactin, which can be used to determine the conserved and variable amino acid positions.

To preserve neurotactin function, it is preferable that conserved residues are not altered. Moreover, alteration of non-conserved residues are preferably conservative alterations, e.g., a basic amino acid is replaced by a different basic amino acid. produce altered function variants, it is preferable to make non-conservative changes at variable and/or conserved positions. Deletions at conserved and variable positions can also be used to create altered function variants.

Other mutations to the neurotactin coding sequence can be made to generate neurotactins that are better suited for expression, scale up, etc. in a selected host cell. For example, N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur (in N-X-S or N-X-T), and/or an amino acid deletion at the second position of any one or more of such recognition sequences, will prevent glycosylation at the modified tripeptide sequence. (See, e.g., Miyajima et al., *EMBO J*. 5:1193, 1986).

In one embodiment, neurotactin polypeptides, or variants thereof, can stimulate chemotaxis of leukocytes (e.g., neutrophils) or mediate adhesion of T cells and natural killer cells expressing neurotactin receptor (V28). In determining whether a particular neurotactin polypeptide or variant thereof stimulates chemotaxis of neutrophils, one can use any standard neutrophil chemotaxis assay. One preferred assay is the chemotaxis assay described herein. Preferred neurotactin polypeptides and variants have 20%, 40%, 50%, 75%, 80%, or even 90% of the activity of the full-length, mature human form of neurotactin described herein. Such comparisons are generally based on equal concentrations of the molecules being compared. The comparison can also be based on the amount of protein or polypeptide required to reach 50% of the maximal stimulation obtainable.

Polypeptides corresponding to one or more domains of neurotactin, e.g., the extracellular domain and the chemokine like domain, are also within the scope of the invention. Preferred polypeptides are those which are soluble under normal physiological conditions. Also within the invention are fusion proteins in which a portion (e.g., one or more domains) of neurotactin is fused to an unrelated protein or polypeptide (i.e., a fusion partner) to create a fusion protein. The fusion partner can be a moiety selected to facilitate purification, detection, or solubilization, or to provide some other function. Fusion proteins are generally produced by expressing a hybrid gene in which a nucleotide sequence encoding all or a portion of neurotactin is joined in-frame to a nucleotide sequence encoding the fusion partner. Fusion partners include, but are not limited to, the constant region of an immunoglobulin (IgFc). A fusion protein in which a neurotactin polypeptide is fused to IgFc can be more stable and have a longer half-life in the body than the neurotactin polypeptide on its own.

Also within the scope of the invention are various soluble forms of neurotactin. For example, the entire extracellular domain of neurotactin or a portion thereof can be expressed on its own or fused to a solubilization partner, e.g., an immunoglobulin.

The invention also features neurotactin polypeptides that can inhibit proliferation of progenitor cells. Such polypeptides are can be used to protect progenitor cells from the effects of chemotherapy and/or radiation therapy. Any convenient in vitro or in vivo assay can be used to determine whether a selected neurotactin polypeptide or variant thereof inhibits progenitor cell proliferation and is thus likely to be a suitable chemoprotective agent. Suitable in vitro assays include those described by Gentile et al. (U.S. Pat. Nos. 5,149,544 and 5,294,544). In addition, inhibition of progenitor cell proliferation can be tested using an in vivo assay. A suitable murine model for assessing progenitor cell proliferation has been described by Cooper et al. (*Exp. Hematol.* 22:186, 1994). The results of this in vivo model, together with the in vitro assay results, are predictive of the efficacy of the tested molecules in treating patients, e.g., humans.

In general, neurotactin proteins according to the invention can be produced by transformation (transfection, transduction, or infection) of a host cell with all or part of a neurotactin-encoding DNA fragment (e.g., the cDNA described herein) in a suitable expression vehicle. Suitable expression vehicles include: plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LACSWITCH™ Inducible Expression System (Stratagene; LaJolla, Calif.).

Those skilled in the field of molecular biology will understand that any of a wide variety of expression systems can be used to provide the recombinant protein. The precise host cell used is not critical to the invention. The neurotactin protein can be produced in a prokaryotic host (e.g., *E. coli* or *B. subtilis*) or in a eukaryotic host (e.g., Saccharomyces or Pichia; mammalian cells, e.g., COS, NIH 3T3, CHO, BHK, 293, or HeLa cells; or insect cells).

Proteins and polypeptides can also be produced by plant cells. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection (ATCC), Manassas, Va.; also, see, e.g., Ausubel et al., *Current Protocols in Molecular Biology*, John Wiley & Sons, New York, 1994). The methods of transformation or transfection and the choice of expression vehicle will depend on the host system selected. Transformation and transfection methods are described, e.g., in Ausubel et al. (*Current Protocols in Molecular Biology*, John Wiley & Sons, New York, 1994); expression vehicles may be chosen from those provided, e.g., in *Cloning Vectors: A Laboratory Manual* (P. H. Pouwels et al., 1985, Supp. 1987).

The host cells harboring the expression vehicle can be cultured in conventional nutrient media adapted as needed for activation of a chosen gene, repression of a chosen gene, selection of transformants, or amplification of a chosen gene.

One preferred expression system is the mouse 3T3 fibroblast host cell transfected with a pMAMneo expression vector (Clontech; Palo Alto, Calif.). pMAMneo provides an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a neurotactin protein can be inserted into the pMAMneo vector in an orientation designed to allow expression. The recombinant neurotactin protein can be isolated as described below. Other preferable host cells that can be used in conjunction with the pMAMneo expression vehicle include COS cells and CHO cells (ATCC Accession Nos. CRL 1650 and CCL 61, respectively).

Neurotactin polypeptides can be produced as fusion proteins. For example, the expression vector pUR278 (Ruther et al., *EMBO J.* 2:1791, 1983), can be used to create lacZ fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect cell expression system, *Autographa californica* nuclear polyhidrosis virus (AcNPV), which grows in *Spodoptera frugiperda* cells, is used as a vector to express foreign genes. A neurotactin coding sequence can be cloned individually into non-essential regions (for example the polyhedrin gene) of the virus and placed under control of an AcNPV promoter, e.g., the polyhedrin promoter. Successful insertion of a gene encoding a neurotactin polypeptide or protein will result in inactivation of the polyhedrin gene and production of non-occluded recombinant virus (i.e., virus lacking the proteinaceous coat encoded by the polyhedrin gene). These recombinant viruses are then used to infect *Spodoptera frugiperda* cells in which the inserted gene is expressed (see, e.g., Smith et al., *J. Virol.* 46:584, 1983; Smith, U.S. Pat. No. 4,215,051).

In mammalian host cells, a number of viral-based expression systems can be utilized. In cases where an adenovirus is used as an expression vector, the neurotactin nucleic acid sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing a neurotactin gene product in infected hosts (see, e.g., Logan, *Proc. Natl. Acad. Sci. USA* 81:3655, 1984).

Specific initiation signals may also be required for efficient translation of inserted nucleic acid sequences. These signals include the ATG initiation codon and adjacent sequences. In cases where an entire native neurotactin gene or cDNA, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators (Bittner et al., *Methods in Enzymol.* 153:516, 1987).

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, and in particular, choroid plexus cell lines.

Alternatively, a neurotactin protein can be produced by a stably-transfected mammalian cell line. A number of vectors suitable for stable transfection of mammalian cells are available to the public, see, e.g., Pouwels et al. (supra); methods for constructing such cell lines are also publicly available, e.g., in Ausubel et al. ( supra). In one example, cDNA encoding the neurotactin protein is cloned into an expression vector that includes the dihydrofolate reductase (DHFR) gene. Integration of the plasmid and, therefore, the neurotactin protein-encoding gene into the host cell chromosome is selected for by including 0.01–300 µM methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. ( supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification.

A number of other selection systems can be used, including but not limited to the herpes simplex virus thymidine kinase, hypoxanthine-guanine phosphoribosyl-transferase, and adenine phosphoribosyltransferase genes can be employed in tk, hgprt, or aprt cells, respectively. In addition, gpt, which confers resistance to mycophenolic acid (Mulligan et al., *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1981), can be used.

Alternatively, any fusion protein can be readily purified by utilizing an antibody specific for the fusion protein being expressed. For example, a system described in Janknecht et al., *Proc. Natl. Acad. Sci. USA,* 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, neurotactin or a portion thereof, can be fused to an immunoglobulin Fc domain. Such a fusion protein can be readily purified using a protein A column. Moreover, such fusion proteins permit the production of a dimeric form of a neurotactin polypeptide having increased stability in vivo.

Neurotactin proteins and polypeptides can also be expressed in transgenic animals. Animals of any species, including, but not limited to, mice, rats, rabbits, guinea pigs, pigs, micropigs, goats, cows and non-human primates, e.g., baboons, monkeys, and chimpanzees, can be used to generate neurotactin-expressing transgenic animals.

Any technique known in the art can be used to introduce a neurotactin transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983).

The present invention provides for transgenic animals that carry the neurotactin transgene in all their cells, as well as animals that carry the transgene in some, but not all of their cells, i.e., mosaic animals. The transgene can be integrated as a single transgene or in concatamers, e.g., head-to-head tandems or head-to-tail tandems The transgene can also be selectively introduced into and activated in a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

When it is desired that the neurotactin transgene be integrated into the chromosomal site of the endogenous neurotactin gene, gene targeting is preferred. Briefly, when such a technique is to be used, vectors containing some nucleotide sequences homologous to an endogenous neurotactin gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous neurotactin gene in only that cell type (Gu et al., *Science* 265:103, 1984). The regulatory sequences required for such a cell-type specific inactivation will depend upon the particular cell type of interest, and will be apparent to those of skill in the art.

Once transgenic animals have been generated, the expression of the recombinant neurotactin gene can be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of neurotactin gene-expressing tissue, also can be evaluated immunocytochemically using antibodies specific for the neurotactin transgene product.

Once the recombinant neurotactin protein is expressed, it is isolated. Secreted forms can be isolated from the culture media, while non-secreted forms must be isolated from the host cells. Proteins can be isolated by affinity chromatography. In one example, an anti-neurotactin protein antibody (e.g., produced as described herein) is attached to a column and used to isolate the neurotactin protein. Lysis and fractionation of neurotactin protein-harboring cells prior to affinity chromatography can be performed by standard methods (see, e.g., Ausubel et al., supra). Alternatively, a neurotactin fusion protein, for example, a neurotactin-maltose binding protein, a neurotactin-β-galactosidase, or a neurotactin-trpE fusion protein, can be constructed and used for neurotactin protein isolation (see, e.g., Ausubel et al., supra; New England Biolabs; Beverly, Mass.).

Once isolated, the recombinant protein can, if desired, be further purified, e.g., by high performance liquid chromatography using standard techniques (see, e.g., Fisher, *Labo-* ratory Techniques In Biochemistry And Molecular Biology, eds., Work and Burdon, Elsevier, 1980).

Polypeptides of the invention, particularly short neurotactin fragments, can also be produced by chemical synthesis (e.g., by the methods described in *Solid Phase Peptide Synthesis,* 2nd edge 1984 The Pierce Chemical Co., Rockford, Ill.).

These general techniques of polypeptide expression and purification can also be used to produce and isolate useful neurotactin fragments or analogs (described herein).

The invention also features proteins which interact with neurotactin and are involved in the function of neurotactin. Also included in the invention are the genes encoding these interacting proteins. Interacting proteins can be identified using methods known to those skilled in the art. One suitable method is the "two-hybrid system," detects protein interactions in vivo (Chien et al., *Proc. Natl. Acad. Sci. USA* 88:9578, 1991). A kit for practicing this method is available from Clontech (Palo Alto, Calif.).

Anti-Neurotactin Antibodies

Human and murine neurotactin proteins and polypeptides (or immunogenic fragments or analogs thereof) can be used to raise anti-neurotactin antibodies useful in the invention. Broadly, anti-neurotactin antibodies can be produced using non-recombinant methods or recombinant methods (or a combination of both methods).

In non-recombinant methods, a protein, polypeptide, or other antigen is used to immunize an animal, e.g., a mouse. The animal produces polyclonal antibodies. Cells isolated from the immunized animal can be used to generate monoclonal antibodies. The animal to be immunized can be a transgenic animal which has been modified to harbor the immunoglobulin heavy and light chain genes from another species. For example, the animal can be a transgenic mouse which is capable of expressing human immunoglobulin heavy and light chain genes, but is incapable of expressing murine immunoglobulin heavy and light chain genes. Such a transgenic mouse, when immunized with a selected antigen, will produce polyclonal human antibodies directed against the antigen. Cells isolated from the animal can be used to generate human monoclonal antibodies.

In recombinant methods, antibody-encoding DNA sequences are manipulated using recombinant DNA technology. Recombinant methods include: "phage display technology," "guided selection," "single chain antibody generation," and "humanized antibody generation." In nearly all recombinant methods, the source of the antibody-encoding DNA sequences being manipulated is either an animal that has been immunized with the antigen of interest or a monoclonal antibody-producing cell line generated using cells isolated from such an animal. Thus, many recombinant methods for producing antibodies also entail the use of non-recombinant methods for producing antibodies.

Antibodies within the invention include, e.g., monoclonal antibodies, polyclonal antibodies, humanized or chimeric antibodies, single chain antibodies, Fab fragments, $F(ab')_2$ fragments, molecules produced using a Fab expression library, and human antibodies (polyclonal or monoclonal) produced in transgenic mice or antibody fragments therof. The term "antibody" as used herein refers to immunoglobulin molecules and immunologically active portions of immunoglobulin molecules, i.e., molecules that contain an antigen binding site which specifically binds an antigen. A molecule which specifically binds to neurotactin is a molecule which binds neurotactin, but does not substantially bind other molecules in a sample, preferably, a biological sample which contains (e.g., naturally contains) neurotactin. Examples of immunologically active portions of immunoglobulin molecules include F(ab) and $F(ab')_2$ fragments which can be generated by treating the antibody with an enzyme such as pepsin. The term "monoclonal antibody" or "monoclonal antibody composition", as used herein, refers to a population of antibody molecules that contain only one species of an antigen binding site capable of immunoreacting with a particular epitope of neurotactin. A monoclonal antibody composition thus typically displays a single binding affinity for a particular neurotactin protein with which it immunoreacts.

To produce non-recombinant antibodies or starting material for the production of recombinant antibodies, a host animal can be immunized by injection with a neurotactin protein or polypeptide. For example, an isolated neurotactin protein, or a portion or fragment thereof, can be used as an immunogen to generate antibodies that bind neurotactin using standard techniques for polyclonal and monoclonal antibody preparation. An appropriate immunogenic preparation can contain, for example, recombinantly expressed neurotactin protein or a chemically synthesized neurotactin polypeptide (see, e.g., *Solid Phase Peptide Synthesis*, supra; Ausubel et al., supra). A full-length neurotactin protein can be used or, alternatively, the invention provides antigenic peptide fragments of neurotactin for use as an immunogen. The antigenic peptide of neurotactin comprises at least 7 (preferably 10, 15, 20, 30, or more) amino acid residues of human neurotactin (SEQ ID NO:4), preferably the chemokine-like domain of human neurotactin (SEQ ID NO:19; amino acids 22 to 92 of SEQ ID NO:4) and encompasses at least one epitope of neurotactin such that an antibody raised against the peptide forms a specific immune complex with neurotactin. Other preferred immunogens include all or a portion (e.g., a portion which comprises at least 7 amino acid residues) of the extracellular domain of human neurotactin (amino acid 22 to amino acid 341 of SEQ ID NO:4; e.g., amino acids 22–28, 23–29, 24–30, 25–31, 26–32, 27–33, 28–34, 29–35, 30–36, 31–37, 32–38, 33–39, 34–40, 35–41, 36–42, 37–43, 38–44, 39–45, 40–46, 41–47, 42–48, 43–49, 44–50, 45–51, 46–52, 47–53, 48–54, 49–55, 50–56, 51–57, 52–58, 53–59, 54–60, 55–61, 56–62, 57–63, 58–64, 59–65, 60–66, 61–67, 62–68, 63–69, 64–70, 65–71, 66–72, 67–73, 68–74, 69–75, 70–76, 71–77, 72–78, 73–79, 74–80, 75–81, 76–82, 77–83, 78–84, 79–85, 80–86, 81–87, 82–88, 83–89, 84–90, 85–91, 86–92, 87–93, 88–94, 89–95, 90–96, 91–97, 92–98, 93–99, 94–100, 95–101, 96–102, 97–103, 98–104, 99–105, 100–106, 101–107, 102–108, 103–109, 104–110, 105–111, 106–112, 107–113, 108–114, 109–115, 110–116, 111–117, 112–118, 113–119, 114–120, 115–121, 116–122, 117–123, 118–124, 119–125, 120–126, 121–127, 122–128, 123–129, 124–130, 125–131, 126–132, 127–133, 128–134, 129–135, 130–136, 131–137, 132–138, 133–139, 134–140, 135–141, 136–142, 137–143, 138–144, 139–145, 140–146, 141–147, 142–148, 143–149, 144–150, 145–151, 146–152, 147–153, 148–154, 149–155, 150–156, 151–157, 152–158, 153–159, 154–160, 155–161, 156–162, 157–163, 158–164, 159–165, 160–166, 161–167, 162–168, 163–169, 164–170, 165–171, 166–172, 167–173, 168–174, 169–175, 170–176, 171–177, 172–178, 173–179, 174–180, 175–181, 176–182, 177–183, 178–184, 179–185, 180–186, 181–187, 182–188, 183–189, 184–190, 185–191, 186–192, 187–193, 188–194, 189–195, 190–196, 191–197, 192–198, 193–199, 194–200, 195–201, 196–202, 197–203, 198–204, 199–205, 200–206, 201–207, 202–208, 203–209, 204–210, 205–211, 206–212, 207–213, 208–214, 209–215, 210–216, 211–217, 212–218, 213–219, 214–220, 215–221, 216–222, 217–223, 218–224, 219–225, 220–226, 221–227, 222–228, 223–229, 224–230, 225–231, 226–232, 227–233, 228–234, 229–235, 230–236, 231–237, 232–238, 233–239, 234–240, 235–241, 236–242, 237–243, 238–244, 239–245, 240–246, 241–247, 242–248, 243–249, 244–250, 245–251, 246–252, 247–253, 248–254, 249–255, 250–256, 251–257, 252–258, 253–259, 254–260, 255–261, 256–262, 257–263, 258–264, 259–265, 260–266, 261–267, 262–268, 263–269, 264–270, 265–271, 266–272, 267–273, 268–274, 269–275, 270–276, 271–277, 272–278, 273–279, 274–280, 275–281, 276–282, 277–283, 278–284, 279–285, 280–286, 281–287, 282–288, 283–289, 284–290, 285–291, 286–292, 287–293, 288–294, 289–295, 290–296, 291–297, 292–298, 293–299, 294–300, 295–301, 296–302, 297–303, 298–304, 299–305, 300–306, 301–307, 302–308, 303–309, 304–310, 305–311, 306–312, 307–313, 308–314, 309–315, 310–316, 311–317, 312–318, 313–319, 314–320, 315–321, 316–322, 317–323, 318–324, 319–325, 320–326, 321–327, 322–328, 323–329, 324–330, 325–331, 326–332, 327–333, and 328–334), all or a portion (e.g., a portion which comprises at least 7 amino acid residues) of the transmembrane domain of human neurotactin (amino acid 342 to amino acid 362 of SEQ ID NO:4; e.g., amino acids 342–348, 343–349, 344–350, 345–351, 346–352, 347–353, 348–354, 349–355, 350–356, 351–357, 352–358, 353–359, 354–360, 355–361, and 356–362), and all or a portion (e.g., a portion which comprises at least 7 amino acid residues) of the cytoplasmic domain of human neurotactin (amino acid 363 to amino acid 397 of SEQ ID NO:4; e.g., amino acids 363–369, 364–370, 365–371, 366–372, 367–373, 368–374, 369–375, 370–376, 371–377, 372–378, 373–379, 374–380, 375–381, 376–382, 377–383, 378–384, 379–385, 380–386, 381–387, 382–388, 383–389, 384–390, 385–391, 386–392, 387–393, 388–394, 389–395, 390–396, and 391–397).

Preferably, antibodies of the invention are produced using fragments of the neurotactin protein which include highly conserved regions and appear likely to be antigenic, by criteria such as hydrophilicity or high frequency of charged residues. In one specific example, such fragments are generated by standard techniques of PCR, and are then cloned into the pGEX expression vector (Ausubel et al., supra) to produce a construct encoding a fusion protein that can be used for immunization. The fusion proteins are expressed in *E. coli* and purified using a glutathione agarose affinity matrix as described in Ausubel, et al., supra. It can be desirable to generate two or three fusion proteins for each polypeptide fragment of interest and inject each fusion protein into two or more animals.

Host animals for the production of antibodies include, for example, rabbits, mice, guinea pigs, and rats. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Generally, animals are injected with antigen using several injections in a series, preferably including at least three booster injections.

Monoclonal antibodies can be prepared using the neurotactin proteins described above and standard hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., In *Monoclonal Antibodies and T Cell Hybridomas*, Elsevier, N.Y., 1981; Ausubel et al., supra). In particular, monoclonal antibodies can be obtained by any technique that provides for the production of antibody molecules by continuous cell lines in culture such as described in Kohler et al., *Nature* 256:495, 1975, and U.S. Pat. No. 4,376,110; the human B-cell hybridoma technique (Kosbor et al., *Immunology Today* 4:72, 1983; Cole et al., *Proc. Natl. Acad. Sci. USA* 80:2026, 1983), and the EBV-hybridoma technique (Cole et al., *Monoclonal Antibodies and Cancer Therapy*, Alan R. Liss, Inc., pp. 77–96, 1983). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this the presently preferred method of production.

Any of the many well known protocols used for fusing lymphocytes and immortalized cell lines can be applied for the purpose of generating an anti-neurotactin monoclonal antibody (see, e.g., Current Protocols in Immunology, Coligan et al. (eds.) John Wiley & Sons, New York, (1996); Galfre et al., *Nature* 266:55052–60, 1977; R. H. Kenneth, in *Monoclonal Antibodies: A New Dimension In Biological Analyses*, Plenum Publishing Corp., New York (1980); and Lerner, Yale *J. Biol. Med.* 54:387–402, 1981). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind neurotactin, e.g., using a standard ELISA assay.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of neurotactin. Monoclonal antibodies directed against the antigen can be obtained using conventional hybridoma technology. The human immunoglobulin transgenes harbored by the transgenic mice rearrange during B cell differentiation and subsequently undergo class switching and somatic mutation. Thus, using such a technique, it is possible to produce therapeutically useful IgG, IgA and IgE antibodies. For an overview of this technology for producing human antibodies, see Lonberg and Huszar (*Int. Rev. Immunol.* 13:65–93, 1995). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806.

Using antibodies produced by non-recombinant (or recombinant) methods, one can generate antibody fragments that recognize and bind to specific epitopes. Such fragments include but are not limited to F(ab')$_2$ fragments that can be produced by pepsin digestion of the antibody molecule, and Fab fragments that can be generated by reducing the disulfide bridges of F(ab')$_2$ fragments.

Recombinant methods can be used to produce single chain antibodies, chimeric antibodies, humanized antibodies, and fully human antibodies directed against neurotactin. Recombinant methods for producing antibodies are described, for example, in: PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., *Science* 240:1041–1043, 1988; Liu et al., *Proc. Natl. Acad. Sci. USA* 84:3439–3443, 1987; Liu et al., *J. Immunol.* 139:3521–3526, 1987; Sun et al., *Proc. Natl. Acad. Sci. USA* 84:214–218, 1987; Nishimura et al., *Canc. Res.* 47:999–1005, 1987; Wood et al., *Nature* 314:446–449, 1985; and Shaw et al., *J. Natl. Cancer Inst.* 80:1553–1559, 1988; Morrison, *Science* 229:1202–1207, 1985; Oi et al., *Bio/Techniques* 4:214, 1986; U.S. Pat. No. 5,225,539; Jones et al., *Nature* 321:552–525, 1986; Verhoeyan et al., *Science* 239:1534, 1988; and Beidler et al., *J. Immunol.* 141:4053–4060, 1988.

A chimeric antibody is a molecule in which different portions are derived from different animal species. For example, a chimeric antibody can have a variable region derived from a murine immunoglobulin variable region and a human immunoglobulin constant region. Techniques developed for the production of chimeric antibodies (Morrison et al., *Proc. Natl. Acad. Sci. USA* 81:6851, 1984; Neuberger et al., *Nature* 312:604, 1984; Takeda et al., *Nature* 314:452, 1984) can be used to produce a chimeric antibody by splicing the genes from a mouse antibody molecule of appropriate antigen specificity (e.g., an anti-neurotactin antibody produced by non-recombinant methods) together with genes from a human antibody molecule of appropriate biological activity. Chimeric antibodies can be humanized by making selected alterations in the murine variable domain CDRs. Humanization methods are described in U.S. Pat. No. 5,585,089.

Recombinant methods can be used to produce single chain antibodies. Single chain antibodies are formed by linking the heavy and light chain fragments of the Fv region via an amino acid bridge, resulting in a single chain polypeptide. Methods for producing such antibodies are described in: U.S. Pat. Nos. 4,946,778; and 4,946,778 and 4,704,692. These methods can be adapted to produce single chain antibodies against a neurotactin protein or polypeptide.

A recombinant combinatorial immunoglobulin library (e.g., an antibody phage display library) can be used to identify and isolate anti-neurotactin antibodies. In this technique, anti-neurotactin antibodies are identified by screening a phage display library with neurotactin to thereby isolate immunoglobulin library members that bind neurotactin. Kits for generating and screening phage display libraries are commercially available (e.g., the *Pharmacia Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display libraries can be found in, for example, U.S. Pat. No. 5,223,409; PCT Publication No. WO 92/18619; PCT Publication No. WO 91/17271; PCT Publication WO 92/20791; PCT Publication No. WO 92/15679; PCT Publication WO 93/01288; PCT Publication No. WO 92/01047; PCT Publication No. WO 92/09690; PCT Publication No. WO 90/02809; Fuchs et al. *Bio/Technolog* 9:1370–1372, 1991; Hay et al., *Hum. Antibod. Hybridomas* 3:81–85, 1992; Huse et al., *Science* 246:1275–1281, 1989; Griffiths et al., *EMBO J.* 12:725–734, 1993.

Guided selection is a recombinant method for generating completely human antibodies which recognize a selected epitope, e.g., an epitope of neurotactin. In this approach, a selected non-human monoclonal antibody, e.g., a murine antibody, is used to guide the selection of a completely human antibody recognizing the same epitope.

First, a non-human monoclonal antibody which binds a selected antigen (epitope), e.g., an antibody which inhibits neurotactin activity, is identified. The heavy chain and the light chain of the non-human antibody are cloned and used to create phage display Fab fragments. For example, the heavy chain gene can be cloned into a plasmid vector so that the heavy chain can be secreted from bacteria. The light chain gene can be cloned into a phage coat protein gene so that the light chain can be expressed on the surface of phage. A repertoire (random collection) of human light chains fused to phage is used to infect the bacteria which express the non-human heavy chain. The resulting progeny phage display hybrid antibodies (human light chain/non-human heavy chain). The selected antigen is used in a panning screen to select phage which bind the selected antigen. Several rounds of selection may be required to identify such phage. Next, human light chain genes are isolated from the selected phage which bind the selected antigen. These selected human light chain genes are then used to guide the selection of human heavy chain genes as follows. The selected human light chain genes are inserted into vectors for expression by bacteria. Bacteria expressing the selected human light chains are infected with a repertoire of human heavy chains fused to phage. The resulting progeny phage display human antibodies (human light chain/human heavy chain). Next, the selected antigen is used in a panning screen to select phage which bind the selected antigen. The phage selected in this step display completely human antibodies which recognize the same epitope recognized by the original selected, non-human monoclonal antibody. The genes encoding both the heavy and light chains are readily isolated and can be further manipulated for production of human antibody. This technology is described by Jespers et al. (*Bio/technology* 12:899–903, 1994).

Fab fragments directed to a selected epitope can be produced recombinantly by constructing a Fab expression library (Huse et al., *Science* 246:1275, 1989). Such libraries allow rapid and easy identification of monoclonal Fab fragments with the desired specificity, e.g., anti-neurotactin antibodies.

Antibodies to neurotactin, produced by any of a number of methods, can be used to generate anti-idiotypic antibodies that resemble a portion of neurotactin using techniques well known to those skilled in the art (see, e.g., Greenspan et al., *FASEB J.* 7:437, 1993; Nissinoff, *J. Immunol.* 147:2429, 1991). For example, antibodies that bind to neurotactin and competitively inhibit the binding of a ligand of neurotactin can be used to generate anti-idiotypes that resemble a ligand binding domain of neurotactin and, therefore, bind and neutralize a ligand of neurotactin. Such neutralizing anti-idiotypic antibodies or Fab fragments of such anti-idiotypic antibodies can be used in therapeutic regimens.

Once produced, anti-neurotactin antibodies are tested for specific neurotactin recognition by Western blot or immunoprecipitation analysis by standard methods, e.g., as described in Ausubel et al., supra or by one of the methods described below in the examples.

The invention includes anti-murine neurotactin antibodies that bind human neurotactin. For example, the invention includes monoclonal antibodies 5b1.4 and 5all.5. These antibodies were created by immunizing mice with a polypeptide that included amino acids 22–337 of murine neurotactin. Monoclonal antibody 561.Y binds immobilized human neurotactin with a $K_D$ of $1.23 \times 10^{-8}$ M. Monoclonal antibody 5all.5 binds immobilized human neurotactin with a $K_D$ of $1.21 \times 10^{-9}$.

Antibodies that specifically recognize and bind to neurotactin are useful in the invention. For example, such antibodies, particularly antibodies which block binding of neurotactin to its receptor, can be used to inhibit neurotactin-associated inflammation associated with a variety of inflammatory disorders. Antibodies which recognize cell-surface neurotactin can be used to label or target, e.g., for killing, cells which express cell surface neurotactin.

Antibodies that recognize and bind neurotactin can also can be used in an immunoassay to monitor the level of neurotactin produced by a mammal (for example, to determine the amount or subcellular location of neurotactin), e.g., in a diagnostic assay.

Antibodies directed against neurotactin also can be used in a screening assay to measure the effect of a candidate compound on expression or localization of neurotactin. Anti-neurotactin antibodies can be used diagnostically to monitor protein levels in tissue as part of a clinical testing procedure to, for example, determine the efficacy of a given treatment regimen. Additionally, such antibodies can be used in conjunction with the gene therapy techniques described to, for example, evaluate the normal and/or engineered neurotactin-expressing cells prior to their introduction into the patient. Such antibodies additionally can be used in a method for inhibiting abnormal neurotactin activity.

An anti-neurotactin antibody (e.g., a monoclonal antibody) can also be used to isolate neurotactin by standard techniques, such as affinity chromatography or immunoprecipitation. An anti-neurotactin antibody can facilitate the purification of natural neurotactin from cells and of recombinantly produced neurotactin expressed in host cells.

Where an antibody is used to detect the presence of, or quantify the level of, a neurotactin polypeptide, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Reducing Neurotactin Expression

In alternate embodiments, anti-inflammation therapy can be designed to reduce the level of endogenous neurotactin gene expression, e.g., using antisense or ribozyme approaches to inhibit or prevent translation of neurotactin mRNA transcripts; triple helix approaches to inhibit transcription of the neurotactin gene; or targeted homologous recombination to inactivate or "knock out" the neurotactin gene or its endogenous promoter. Because the neurotactin gene is expressed in the brain, including the choroid plexus and arcuate nucleus, delivery techniques should be preferably designed to cross the blood-brain barrier (see, e.g., PCT Publication No. WO89/10134). Alternatively, the antisense, ribozyme, or DNA constructs described herein can be administered directly to the site containing the target cells; e.g., brain, heart, kidney, lung, uterus, endothelial cells, fibroblasts, and bone marrow stromal cells.

Antisense Nucleic Acids

Antisense approaches involve the design of oligonucleotides (either DNA or RNA) that are complementary to neurotactin mRNA. The antisense oligonucleotides bind to the complementary neurotactin mRNA transcripts and prevent translation. Absolute complementarity, although preferred, is not required. A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs recently have been shown to be effective at inhibiting translation of mRNAs as well (Wagner, Nature 372:333, 1984). Thus, oligonucleotides complementary to either the 5'- or 3'-non-translated, non-coding regions of the neurotactin gene, e.g., the human gene shown in FIG. 2, could be used in an antisense approach to inhibit translation of endogenous neurotactin mRNA. Oligonucleotides complementary to the 5' untranslated region of the mRNA should include the complement of the AUG start codon.

Antisense oligonucleotides complementary to mRNA coding regions are less efficient inhibitors of translation but could be used in accordance with the invention. Whether designed to hybridize to the 5'-, 3'-, or coding region of neurotactin mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., Proc. Natl. Acad. Sci. USA 86:6553, 1989; Lemaitre et al., Proc. Natl. Acad. Sci. USA 84:648, 1987; PCT Publication No. WO 88/09810) or the blood-brain barrier (see, e.g., PCT Publication No. WO 89/10134), or hybridization-triggered cleavage agents (see, e.g., Krol et al., BioTechniques 6:958, 1988), or intercalating agents (see, e.g., Zon, Pharm. Res. 5:539, 1988). To this end, the oligonucleotide can be conjugated to another molecule, e.g., a peptide, hybridization triggered cross-linking agent, transport agent, or hybridization-triggered cleavage agent.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids. Res. 15:6625, 1987). The oligonucleotide is a 2'-0-methylribonucleotide (Inoue et al., Nucl. Acids Res. 15:6131, 1987), or a chimeric RNA-DNA analog (Inoue et al., FEBS Lett. 215:327, 1987).

Antisense oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthe-sized by the method of Stein et al. (Nucl. Acids Res. 16:3209, 1988), and methylphosphonate oligonucleotides can be prepared by use of controlled pore glass polymer supports (Sarin et al., Proc. Natl. Acad. Sci. USA 85:7448, 1988).

While antisense nucleotides complementary to the neurotactin coding region sequence could be used, those complementary to the transcribed untranslated region are most preferred.

One example of a 15 nucleotide antisense sequence to the human neurotactin gene is 5'-TATCGGAGCCATGGC-3' (SEQ ID NO:5), where the underlined sequence represents the complement of the initiator methionine codon.

The antisense molecules can be delivered to cells that express neurotactin in vivo, e.g., brain, heart, kidney, lung, uterus, endothelial cells, fibroblasts, and bone marrow stromal cells. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

To achieve intracellular concentrations of the antisense molecule sufficient to suppress translation of endogenous mRNAs, a preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous neurotactin transcripts and thereby prevent translation of the neurotactin mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include, but are not limited to: the SV40 early promoter region (Bernoist et al., Nature 290:304, 1981); the promoter contained in the 3' long terminal repeat of Rous sarcoma virus (Yamamoto et al., Cell 22:787–797, 1988); the herpes thymidine kinase promoter (Wagner et al., Proc. Natl. Acad. Sci. USA 78:1441, 1981); or the regulatory sequences of the metallothionein gene (Brinster et al., Nature 296:39, 1988).

Any type of plasmid, cosmid, YAC, or viral vector can be used to prepare the recombinant DNA construct which can be introduced directly into the tissue site; e.g., the brain, heart, kidney, lung, uterus, endothelial cells, fibroblasts, and bone marrow stromal cells. Alternatively, viral vectors can be used that selectively infect the desired tissue (e.g., for brain, herpesvirus vectors may be used), in which case administration can be accomplished by another route (e.g., systemically).

Ribozymes

Ribozyme molecules designed to catalytically cleave neurotactin mRNA transcripts also can be used to prevent translation of neurotactin mRNA and expression of neurotactin (see, e.g., PCT Publication No. WO 90/11364; Saraver et al., Science 247:1222, 1990). While various ribozymes that cleave mRNA at site-specific recognition sequences can be used to destroy neurotactin mRNAs, the use of hammerhead ribozymes is preferred. Hammerhead ribozymes cleave mRNAs at locations dictated by flanking regions that form complementary base pairs with the target mRNA. The sole requirement is that the target its mRNA have the following sequence of two bases: 5'-UG-3'. The construction and production of hammerhead ribozymes is well known in the art (Haseloff et al., *Nature* 334:585, 1988). There are numerous examples of potential hammerhead ribozyme cleavage sites within the nucleotide sequence of human neurotactin cDNA (FIGS. 2A–2B). Preferably, the ribozyme is engineered so that the cleavage recognition site is located near the 5' end of the neurotactin mRNA, i.e., to increase efficiency and minimize the intracellular accumulation of non-functional mRNA transcripts.

Examples of potential ribozyme sites in human neurotactin include 5'-UG-3' sites which correspond to the initiator methionine codon (nucleotides 87–88) and the codons for each of the cysteine residues of the chemokine-like domain (e.g., nucleotides 179–180, 191–192, 257–258, and 305–306).

The ribozymes of the present invention also include RNA endoribonucleases (hereinafter "Cech-type ribozymes"), such as the one that occurs naturally in *Tetrahymena Thermophila* (known as the IVS or L-19 IVS RNA), and which has been extensively described by Cech and his collaborators (Zaug et al., *Science* 224:574, 1984; Zaug et al., *Science* 231:470, 1986; Zug et al., *Nature* 324:429, 1986; PCT Application No. WO 88/04300; and Been et al., *Cell* 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in neurotactin.

As in the antisense approach, the ribozymes can be composed of modified oligonucleotides (e.g., for improved stability, targeting, etc.), and should be delivered to cells which express the neurotactin in vivo, e.g., brain, heart, kidney, lung, uterus, endothelial cells, fibroblasts, and bone marrow stromal cells. A preferred method of delivery involves using a DNA construct "encoding" the ribozyme under the control of a strong constitutive pol III or pol II promoter, so that transfected cells will produce sufficient quantities of the ribozyme to destroy endogenous neurotactin messages and inhibit translation. Because ribozymes, unlike antisense molecules, are catalytic, a lower intracellular concentration is required for efficiency.

Other Methods for Reducing Neurotactin Expression

Endogenous neurotactin gene expression can also be reduced by inactivating or "knocking out" the neurotactin gene or its promoter using targeted homologous recombination (see, e.g., U.S. Pat. No. 5,464,764). For example, a mutant, non-functional neurotactin (or a completely unrelated DNA sequence) flanked by DNA homologous to the endogenous neurotactin gene (either the coding regions or regulatory regions of the neurotactin gene) can be used, with or without a selectable marker and/or a negative selectable marker, to transfect cells that express neurotactin in vivo. Insertion of the DNA construct, via targeted homologous recombination, results in inactivation of the neurotactin gene. Such approaches are particularly suited for use in the agricultural field where modifications to ES (embryonic stem) cells can be used to generate animal offspring with an inactive neurotactin. However, this approach can be adapted for use in humans, provided the recombinant DNA constructs are directly administered or targeted to the required site in vivo using appropriate viral vectors, e.g., herpes virus vectors for delivery to brain tissue; e.g., the arcuate nucleus or the choroid plexus.

Alternatively, endogenous neurotactin gene expression can be reduced by targeting deoxyribonucleotide sequences complementary to the regulatory region of the neurotactin gene (i.e., the neurotactin promoter and/or enhancers) to form triple helical structures that prevent transcription of the neurotactin gene in target cells in the body (Helene, *Anticancer Drug Des.* 6:569, 1981; Helene et al., *Ann. N.Y. Acad. Sci.* 660:27, 1992; and Macer, *Bioassay* 14:807, 1992).

The Identification of Proteins and Compounds Which Interact with Neurotactin

The invention also features proteins and compounds which interact with neurotactin. Any method suitable for detecting protein-protein interactions may be employed for identifying transmembrane proteins, intracellular, or extracellular proteins that interact with neurotactin. Among the traditional methods which may be employed are co-immunoprecipitation, crosslinking and co-purification through gradients or chromatographic columns of cell lysates or proteins obtained from cell lysates and the use of neurotactin to identify proteins in the lysate that interact with the neurotactin. For these assays, the neurotactin polypeptide can be a full length neurotactin, a soluble extracellular domain of neurotactin, or some other suitable neurotactin polypeptide. Once isolated, such an interacting protein can be identified and cloned and then used, in conjunction with standard techniques, to identify proteins with which it interacts. For example, at least a portion of the amino acid sequence of a protein which interacts with the neurotactin can be ascertained using techniques well known to those of skill in the art, such as via the Edman degradation technique. The amino acid sequence obtained may be used as a guide for the generation of oligonucleotide mixtures that can be used to screen for gene sequences encoding the interacting protein. Screening may be accomplished, for example, by standard hybridization or PCR techniques. Techniques for the generation of oligonucleotide mixtures and the screening are well-known. (Ausubel, supra; and *PCR Protocols: A Guide to Methods and Applications,* 1990, Innis et al., eds. Academic Press, Inc., New York, N.Y.).

Additionally, methods may be employed which result directly in the identification of genes which encode proteins which interact with neurotactin. These methods include, for example, screening expression libraries, in a manner similar to the well known technique of antibody probing of λgt11 libraries, using labeled neurotactin polypeptide or a neurotactin fusion protein, e.g., an neurotactin polypeptide or domain fused to a marker such as an enzyme, fluorescent dye, a luminescent protein, or to an IgFc domain.

In a related aspect, the invention features a method of identifying a compound that modulates the expression or activity of neurotactin. The method is carried out by assessing the expression or activity of neurotactin in the presence and absence of the potential modulatory compound.

In one embodiment, the invention provides assays for screening candidate or test compounds which bind to or modulate the activity of the membrane-bound form of a neurotactin protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, *Anticancer Drug Des.* 12:145, 1997).

Examples of methods for the synthesis of molecular libraries can be found in the art, for example in: DeWitt et al., *Proc. Natl. Acad. Sci. USA* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994.

Libraries of compounds may be presented in solution (e.g., Houghten, *Bio/Techniques* 13:412–421, 1992), or on beads (Lam, *Nature* 354:82–84, 1991), chips (Fodor, *Nature* 364:555–556, 1993), bacteria (U.S. Pat. No. 5,223,409), spores (U.S. Pat. Nos. 5,571,698; 5,403,484; and 5,223,409), plasmids (Cull et al., *Proc. Natl. Acad. Sci. USA* 89:1865–1869, 1992) or phage (Scott and Smith, *Science* 249:386–390, 1990; Devlin, *Science* 249:404–406, 1990; Cwirla et al., *Proc. Natl. Acad. Sci. USA* 87:6378–6382, 1990; and Felici, *J. Mol. Biol.* 222:301–310, 1991).

In one embodiment, an assay is a cell-based assay in which a cell which expresses a membrane-bound form of XXX protein, or a biologically active portion thereof, on the cell surface is contacted with a test compound and the ability of the test compound to bind to a neurotactin protein determined. The cell, for example, can be a yeast cell or a cell of mammalian origin. Determining the ability of the test compound to bind to the XXX protein can be accomplished, for example, by coupling the test compound with a radioisotope or enzymatic label such that binding of the test compound to the neurotactin protein or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of neurotactin protein, or a biologically active is portion thereof, on the cell surface with a known compound which binds neurotactin to form an assay mixture, contacting the assay mixture with a test compound, and determining the ability of the test compound to interact with a neurotactin protein, wherein determining the ability of the test compound to interact with a neurotactin protein comprises determining the ability of the test compound to preferentially bind to neurotactin or a biologically active portion thereof as compared to the known compound.

In another embodiment, an assay is a cell-based assay comprising contacting a cell expressing a membrane-bound form of neurotactin protein, or a biologically active portion thereof, on the cell surface with a test compound and determining the ability of the test compound to modulate (e.g., stimulate or inhibit) the activity of the neurotactin protein or biologically active portion thereof. Determining the ability of the test compound to modulate the activity of neurotactin or a biologically active portion thereof can be accomplished, for example, by determining the ability of the neurotactin protein to bind to or interact with a neurotactin target molecule, e.g., a molecule with which a neurotactin protein binds or interacts in nature (e.g., neurotactin receptor), for example, a molecule on the surface of a cell which expresses a neurotactin protein, a molecule on the surface of a second cell, a molecule in the extracellular milieu, a molecule associated with the internal surface of a cell membrane or a cytoplasmic molecule. A neurotactin target molecule can be a non-neurotactin molecule or a neurotactin protein or polypeptide of the present invention.

Determining the ability of the neurotactin protein to bind to or interact with a neurotactin target molecule can be accomplished by one of the methods described above for determining direct binding. In a preferred embodiment, determining the ability of the neurotactin protein to bind to or interact with a neurotactin target molecule can be accomplished by determining the activity of the target molecule.

In yet another embodiment, an assay of the present invention is a cell-free assay comprising contacting a neurotactin protein or biologically active portion thereof with a test compound and determining the ability of the test compound to bind to the neurotactin protein or biologically active portion thereof. Binding of the test compound to the neurotactin protein can be determined either directly or indirectly as described above. In a preferred embodiment, the assay includes contacting the neurotactin protein or biologically active portion thereof with a known compound which binds neurotactin to form an assay mixture, contacting the assay mixture with a test compound, and determining the ability of the test compound to interact with a neurotactin protein, wherein determining the ability of the test compound to interact with a neurotactin protein comprises determining the ability of the test compound to preferentially bind to neurotactin or biologically active portion thereof as compared to the known compound.

In another embodiment, an assay is a cell-free assay comprising contacting neurotactin protein or biologically active portion thereof with a test compound and determining the ability of the test compound to modulate (e.g., stimulate or inhibit) the activity of the neurotactin protein or biologically active portion thereof. Determining the ability of the test compound to modulate the activity of neurotactin can be accomplished, for example, by determining the ability of the neurotactin protein to bind to a neurotactin target molecule by one of the methods described above for determining direct binding. In an alternative embodiment, determining the ability of the test compound to modulate the activity of neurotactin can be accomplished by determining the ability of the neurotactin protein to further modulate a neurotactin target molecule. For example, the catalytic/enzymatic activity of the target molecule on an appropriate substrate can be determined as previously described.

In yet another embodiment, the cell-free assay comprises contacting the neurotactin protein or biologically active portion thereof with a known compound which binds neurotactin to form an assay mixture, contacting the assay mixture with a test compound, and determining the ability of the test compound to interact with a neurotactin protein, wherein determining the ability of the test compound to interact with a neurotactin protein comprises determining the ability of the neurotactin protein to preferentially bind to or modulate the activity of a neurotactin target molecule.

The cell-free assays of the present invention are amenable to use of both the soluble form or the membrane-bound form of neurotactin. In the case of cell-free assays comprising the membrane-bound form of neurotactin, it may be desirable to utilize a solubilizing agent such that the membrane-bound form of neurotactin is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton? X-100, Triton? X-114, Thesit?, Isotridecypoly(ethylene glycol ether)n, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either neurotactin or its target molecule to facilitate separation of complexed from uncomplexed forms of one or both of the proteins, as well as to accommodate automation of the assay. Binding of a test compound to neurotactin, or interaction of neurotactin with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a to domain that allows one or both of the proteins to be bound to a matrix. For example, glutathione-S-transferase/neurotactin fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or neurotactin protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of neurotactin binding or activity determined using standard techniques.

Other techniques for immobilizing proteins on matrices can also be used in the screening assays of the invention. For example, either neurotactin or its target molecule can be immobilized utilizing conjugation of biotin and streptavidin. Biotinylated neurotactin or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with neurotactin or target molecules but which do not interfere with binding of the neurotactin protein to its target molecule can be derivatized to the wells of the plate, and unbound target or neurotactin trapped in the wells by antibody conjugation. Methods for detecting such complexes, in addition to those described above for the GST-immobilized complexes, include immunodetection of complexes using antibodies reactive with the neurotactin or target molecule, as well as enzyme-linked assays which rely on detecting an enzymatic activity associated with the neurotactin or target molecule.

In another embodiment, modulators of neurotactin expression are identified in a method in which a cell is contacted with a candidate compound and the expression of neurotactin mRNA or protein in the cell is determined. The level of expression of neurotactin mRNA or protein in the presence of the candidate compound is compared to the level of expression of neurotactin mRNA or protein in the absence of the candidate compound. The candidate compound can then be identified as a modulator of neurotactin expression based on this comparison. For example, when expression of neurotactin mRNA or protein is greater (statistically significantly greater) in the presence of the candidate compound than in its absence, the candidate compound is identified as a stimulator of neurotactin mRNA or protein expression. Alternatively, when expression of neurotactin mRNA or protein is less (statistically significantly less) in the presence of the candidate compound than in its absence, the candidate compound is identified as an inhibitor of neurotactin mRNA or protein expression. The level of neurotactin mRNA or protein expression in the cells can be determined by methods described herein for detecting neurotactin mRNA or protein.

Methods which can be used to detect protein interaction are known to those of skill in the art. For example, one method which detects protein interactions in vivo is the two-hybrid system (Chien et al., *Proc. Natl. Acad. Sci. USA* 88:9578, 1991). A kit for practicing this method is available from Clontech (Palo Alto, Calif.).

Briefly, utilizing such a system, plasmids are constructed that encode two hybrid proteins: one plasmid includes a nucleotide sequence encoding the DNA-binding domain of a transcription activator protein fused to a nucleotide sequence encoding neurotactin, a neurotactin polypeptide, or a neurotactin fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, neurotactin may be used as the bait gene product. Total genomic or cDNA sequences are fused to the DNA encoding an activation domain. This library and a plasmid encoding a hybrid of bait neurotactin gene product fused to the DNA-binding domain are cotransformed into a yeast reporter strain, and the resulting transformants are screened for those that express the reporter gene. For example, a bait neurotactin gene sequence, such as neurotactin or a domain of neurotactin can be cloned into a vector such that it is translationally fused to the DNA encoding its the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait neurotactin gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait neurotactin gene-GAL4 fusion plasmid into a yeast strain which contains a lacZ gene driven by a promoter which contains GAL4 activation sequence. A cDNA encoded protein, fused to GAL4 transcriptional activation domain, that interacts with bait neurotactin gene product will reconstitute an active GAL4 protein and thereby drive expression of the HIS3 gene. Colonies which express HIS3 can then be purified from these strains, and used to produce and isolate the bait neurotactin gene-interacting protein using techniques routinely practiced in the art.

Neurotactin and the Treatment of Inflammation

Because neurotactin is highly expressed in the brain, is upregulated in response to inflammatory stimuli (e.g., LPS and PMA) in endothelial cells (e.g., cells which line the vasculature) and is chemotactic for leukocytes (described in detail below), neurotactin may play a significant role in brain inflammation. Accumulation of neutrophils in tissues is a hallmark of inflammation. Accordingly, undesirable inflammation of the brain associated with disorders such as viral encephalitis, multiple sclerosis, viral or bacterial meningitis, severe head trauma, stroke, neuro-degenerative diseases (e.g., Alzheimer's disease is and Lou Gehrig's disease), HIV encephalopathy, primary brain tumors (e.g., glioblastomas), Lupus associated cerebritis, and post-seizure brain injury, as well as a variety of TH-1-related inflammatory disorders can be reduced by the administration of a compound that interferes with neurotactin expression or function. Compounds which interfere with neurotactin function or expression can also be used to treat other undesirable inflammatory processes, e.g., atherosclerosis or respiratory infections.

Of course, in some circumstances, including certain phases of many of the above-described conditions, it may be desirable to enhance neurotactin function or expression, e.g., to recruit immune cells that will resolve the primary infection or mediate an anti-tumor response.

Neurotactin as a Chemoprotective Agent

This invention also relates to the use of neurotactin polypeptides to protect myeloid cells, e.g., myeloid progenitor cells, and myeloid stem cells, from drugs or therapies which kill or injure actively dividing cells. Agents which protect myeloid progenitor cells and stem cells in this manner are referred to as chemoprotective agents. Such agents place myeloid progenitor cells (e.g., stem cells) into a protected, slow cell-cycling state, thereby inhibiting or decreasing cell damage or death that could otherwise be caused by cell-cycle active chemotherapy drugs such as cytosine arabinoside, 5-fluorouracil, or hydroxyurea. The use of chemoprotective agents permits the administration of higher doses of chemotherapeutics (or radiation) without compromising the ability of the patient to generate mature functional blood cells.

Many patients who undergo chemotherapy or radiation therapy lose a substantial number of stem cells and other actively dividing myeloid progenitor cells. This loss causes the patients to become susceptible to infection and anemia. One approach for preventing neutropenia is to inhibit cell proliferation with low doses of a molecule which inhibits cell cycling, thereby protecting the progenitor cells from the effects of chemotherapy and/or radiation therapy. After chemotherapy has ended, the protective treatment is also stopped, which allows the progenitor cells to resume normal proliferation.

Any convenient in vitro or in vivo assay can be used to identify preferred neurotactin polypeptides or variants thereof which inhibit progenitor cell proliferation and are thus likely to be a suitable chemoprotective agent.

Suitable in vitro assays include those described by Gentile et al. (U.S. Pat. Nos. 5,149,544 and 5,294,544). In these assays, bone marrow or spleen cells are stimulated with, e.g., CSF, in an in vitro system. The inhibitory activity of a candidate molecule (e.g., neurotactin) is assessed by determining the extent to which it decreases CSF-stimulated colony and cluster formation.

For example, a neurotactin polypeptide or variant can be tested as follows. LD cells are plated at a density of $5\times10^5$ cells in 0.3% agar culture medium with 10% FBS (Hyclone, Logan, Utah) for assessment of CFU-GM. CFU-GM colonies (>40 cells/group) are stimulated by human rGM-CSF (100 U/ml) in combination with human rSLF (50 ng/ml). All colonies are tested in the absence or presence of different concentrations of a neurotactin polypeptide (or variant thereof) to determine the degree inhibition of proliferation.

Colonies are scored after 14 days incubation at lowered (5%) $O_2$ tension, and 5% $CO_2$ in a humidified environment in an ESPEC $N_2$-$O_2$-$CO_2$ incubator BNP-210 (Taoi ESPEC Corp., South Plainfield, N.J.). Three plates are scored per determination.

Suitable molecules are those which are effective to significantly inhibit colony formation by human bone marrow GM progenitor cells at concentrations of at least 200 ng/ml, preferably 100 ng/ml, more preferably 50 ng/ml, or even 10 ng/ml. By assaying a number of neurotactin polypeptides it is possible to identify a domain of neurotactin which causes significant inhibition of proliferation.

In addition, inhibition of progenitor cell proliferation can be tested using an in vivo assay. A suitable murine model for assessing progenitor cell proliferation has been described by Cooper et al. (*Exp. Hematol.* 22:186, 1994). The results of this in vivo model, together with the in vitro assay results, are predictive of the efficacy of the tested molecules in treating patients, e.g., humans.

In suitable in vivo tests, molecules are evaluated for effects on myelopoiesis in mice, with endpoints being nucleated cellularity and differentials in the bone marrow, spleen, and peripheral blood, and absolute numbers and cycling status of myeloid progenitor cells in the marrow and spleen. In each test, groups of C3H/HeJ mice are exposed to a particular test sample. C3H/HeJ mice are preferred because they are relatively insensitive to the effects of endotoxin. Thus, any potential endotoxin contamination in the test samples will not influence the in vivo results.

Neurotactin polypeptides can be tested as follows, although other assays are also useful. C3H/HeJ mice are obtained from the Jackson Laboratory (Bar Harbor, Me.) and housed in a conventional animal facility. The mice are injected intravenously with 0.2 ml/mouse sterile pyrogen-free saline, or the stated amount of a selected neurotactin polypeptide or variant as described in Mantel et al. (*Proc. Natl Acad. Sci. USA* 90:2232, 1993). The mice are sacrificed 24 hours later.

The cycling status of hematopoietic progenitor cells, i.e., the proportion of progenitor cells in DNA synthesis (S phase of the cell cycle), is estimated as described in Maze et al. (*J. Immunol.* 149:1004, 1992) and Cooper et al. (*Exp. Hematol.* 22:186, 1994). The high specific activity (20 Ci/mM)-tritiated thymidine (50 µCi/mL) (New England Nuclear; Boston, Mass.) kill technique is used, and is based on a calculation in vitro of the reduction in the number of colonies formed after pulse exposure of cells for 20 minutes to "hot" tritiated thymidine as compared with a control such as McCoy's medium or a comparable amount of non-radioactive "cold" thymidine.

Femoral bone marrow is removed from the sacrificed mice, treated with high-specific-activity tritiated thymidine, and plated in 0.3% agar culture medium with 10% FBS in the presence of 10% volume/volume pokeweed mitogen mouse spleen cell cultured medium. Colonies (>40 cells/aggregate) and clusters (3–40 cells) are scored after 7 days of incubation.

Three plates are scored for each sample for a statistical analysis. Each mouse is evaluated separately in groups of three mice each.

Preferred neurotactin polypeptides and variants are effective at a dosage of 200 µg/mouse, 100 µg/mouse, 50 µg/mouse, or even 10 µg/mouse or lower. An effective dosage will reduce progenitor cell cycling by at least 25% or at least 50% or even more.

Chemoprotective neurotactin polypeptides can be administered to a patient as adjunctive agents before and/or during chemotherapy or radiation therapy to protect progenitor cells from the cytotoxic effects of the chemotherapeutic agents or radiation. Chemoprotective neurotactin polypeptides place myeloid cells into a protected, slow-cycling state, thereby inhibiting or decreasing cell damage that could otherwise be caused by cell-cycle active chemotherapy drugs such as cytosine arabinoside, 5-fluorouracil, or hydroxyurea. The use of chemoprotective agents permits the administration of higher doses of chemotherapeutics without compromising the ability of the patient to generate mature functional blood cells.

Chemoprotective neurotactin polypeptides are administered to a patient in the same manner as chemokines generally, e.g., injected intravenously or subcutaneously, in a pharmaceutically acceptable carrier.

In chemotherapy, specific protocols may vary, and factors such as tumor size, growth rate, and location of the tumor all affect the course of therapy. The administration protocols for chemotherapeutic agents as well as chemoprotective agents will depend on the extent of disease, the toxicity of previous treatment courses, and the degree of the expected chemotherapeutic drug toxicity.

EXAMPLES

Example 1 describes the identification and sequencing of a murine neurotactin gene and a human neurotactin gene. Example 2 describes the characterization of neurotactin, including its expression pattern and its ability to act as a chemoattractant for neutrophils. Example 3 describes the chromosomal mapping of the neurotactin gene. Example 4 demonstrates that a soluble form of recombinant neurotactin can act as a chemoattractant. Example 5 describes the expression of neurotactin in a murine model of multiple sclerosis. Example 6 describes genomic mapping of the neurotactin gene. Example 7 describes studies involving the administration of anti-neurotactin antibodies to the mice of Example 5. Example 8 describes the distribution of neurotactin in murine brain. Example 9 describes a study demonstrating that neurotactin-deficient mice are less susceptible to ischemia-reperfusion injury than wild-type mice. Example 10 describes additional studies involving the administration of anti-neurotactin antibodies to the mice of Example 5. Example 11 describes the production of monoclonal anti-murine neurotactin antibodies. Example 12 describes the production of anti-human neurotactin antibodies. Example 13 describes a method for measuring the binding of neurotactin to target cells. Example 14 describes an analysis of anti-murine neurotactin antibody binding to human neurotactin. Example 15 describes experiments concerning the displacement of human neurotactin from THP-1 cells by anti-murine neurotactin monoclonal antibodies. Example 16 describes a method for producing human anti-neurotactin antibodies. Example 17 describes a method which can be used to measure neurotactin-stimulated chemotaxis. Example 18 describes a method which can be used to detect cell surface expression of neurotactin. Example 19 describes the treatment of Th1-associated disorders with neurotactin or modulators of neurotactin expression or activity. Example 20 describes certain therapeutic applications of the invention. Example 21 describes certain diagnostic applications of the invention.

Example 1

Cloning of the Neurotactin Gene

The gene for murine neurotactin was identified in a murine choroid plexus cDNA library. This murine neurotactin gene was used to identify a human neurotactin gene. The identification and sequencing of both genes is described in this first example.

Choroid-Plexus mRNA Isolation

The murine mRNA used to create the murine choroid plexus library was prepared as follows. Total RNA was isolated from mouse choroid plexus tissue using the guanidinium isothiocyanate/CsCl method of Chirgwin et al. (*Biochemistry* 18:5294, 1979) as described in Current Protocols for Molecular Biology (supra). The RNA was quantitated, diluted to 1 mg/ml in water, and then incubated for 30 minutes at 37° C. with an equal volume of DNase solution (20 mM $MgCl_2$, 2 mM DTT, 0.1 units DNase, 0.6 units RNase inhibitor in TE) to remove contaminating DNA. The RNA was then extracted with phenol-chloroform-isoamyl alcohol, and ethanol precipitated. After to quantitation at 260 nm, an aliquot was electrophoresed to check the integrity of the RNA. Next, PolyA$^+$ RNA was isolated using an Oligotex-dT kit from Qiagen (Chatsworth, Calif.) as described by the manufacturer. After quantitation, the mRNA was precipitated in ethanol and resuspended at a concentration of 1 mg/ml in water.

cDNA Library Construction

The isolated choroid plexus mRNA described above was used to prepare cDNA as follows.

Choroid plexus mRNA was used as a template for preparation of cDNA according to the method of Gubler et al. (*Gene* 25: 263, 1983) using a Superscript Plasmid cDNA synthesis kit (Life Technologies; Gaithersburg, Md.). The cDNA obtained was ligated into the NotI/SalI sites of the mammalian expression vector pMET7, a modified version of pME18S, which utilizes the SRa promoter as described previously (Takebe, *Mol. Cell. Bio.* 8:466, 1988). Ligated cDNA was transformed into electrocompetent DH101B *E. coli* either prepared by standard procedures or obtained from Life Technologies.

DNA Preparation and Sequence Analysis

A number of cDNA clones in the murine choroid plexus library were sequenced to identify sequences of interest. The identified sequences were then used to clone and sequence a complete murine neurotactin gene. The identification and analysis was performed as follows.

First, 96-well plates were inoculated with individual choroid plexus library transformants in 1 ml of LB-amp. These inoculations were based on the titers of the cDNA transformants. The resulting cultures were grown for 15 to 16 hours at 37° C. with aeration. Prior to DNA preparation, 100 µl of cell suspension was removed and added to 100 µl of 50% glycerol, mixed and stored at −80° C. (glycerol freeze plate). DNA was then prepared using the Wizard™ miniprep system (Promega; Madison, Wis.) employing modifications for a 96-well format.

The insert cDNAs of a number of clones were sequenced by standard, automated fluorescent dideoxynucleotide sequencing using dye-primer chemistry (Applied Biosystems, Inc., Foster City, Calif.) on Applied Biosystems 373 and 377 sequenators (Applied Biosystems). The primer used in this sequencing was proximal to the SRa promoter of the vector and therefore selective for the 5' end of the clones, although other primers with this selectivity can also be used. The short cDNA sequences obtained in this manner were screened as follows.

First, each sequence was checked to determine if it was a bacterial, ribosomal, or mitochondrial contaminant. Such sequences were excluded from the subsequent analysis. Second, sequence artifacts, such as vector and repetitive elements, were masked and/or removed from each sequence. Third, the remaining sequences were searched against a copy of the GenBank nucleotide database using the BLASTN program (BLASTN 1.3MP; Altschul et al., *J. Mol. Bio.* 215:403, 1990). Fourth, the sequences were analyzed against a non-redundant protein database with the BLASTX program (BLASTX 1.3MP; Altschul et al., supra). This protein database is a combination of the Swiss-Prot, PIR, and NCBI GenPept protein databases. The BLASTX program was run using the default BLOSUM-62 substitution matrix with the filter parameter: "xnu+seg". The score cutoff utilized was 75.

Overlapping clones were assembled into contigs using the Sequencher program(Gene Codes Corp.; Ann Arbor, Mich.). The assembled contigs were analyzed using the programs in the GCG package (Genetic Computer Group, University Research Park, 575 Science Drive, Madison, Wis. 53711).

The above-described analysis resulted in the identification of a clone (clone ID jfmjd006h11) having an open reading frame of 395 amino acids (FIGS. 1A–1B). The protein encoded by this clone was named neurotactin. The first approximately 21 amino acids in this open reading frame were predicted to be a signal sequence using the method of Von Heijne (*J. Membrane Biol.* 115:195, 1990). The amino-terminal portion of murine neurotactin has significant homology to the known C-C family of chemokines. This portion is 40% identical to mouse monocyte MCP-1 based on a primary sequence alignment of residues 23 to 92 of murine neurotactin with murine MCP-1.

The sequence of the murine neurotactin gene was used to search the DBEST expressed sequence tag (EST) database using the BLASTN program. The clone corresponding to a selected EST was obtained from Genome Systems Inc. and sequenced in full (FIGS. 2A–2B). The sequence of this clone differed from that of the initially identified EST at position 319. Compared to the sequence of the clone, there is a one base pair deletion in the EST sequence which results in a reading frame shift. Because of this deletion, the predicted amino acid sequence of the clone differs from the predicted amino acid sequence corresponding to the EST. This form of human neurotactin is 42% identical to human MCP-1 based on a primary sequence alignment of residue 23 to 92 of human neurotactin with human MCP-1 (Swiss Prot # 13500). Overall human neurotactin contains 397 amino acids and is 67% identical to the form of murine neurotactin described herein (FIG. 4). Higher than average homology is observed at the chemokine-like region at the N-terminal. The regions having the greatest homology are the transmembrane domain and the cytoplasmic domain.

Example 2

Characterization of Neurotactin

The expression pattern of neurotactin was examined as described below. Also described below is the expression of a recombinant form of soluble murine neurotactin and experiments demonstrating that neurotactin stimulates chemotaxis of neutrophils.

Analysis-of Neurotactin Expression

Northern analysis was used to examine neurotactin expression as follows. First, total RNA from the following cell types was extracted with RNAsol when the cells were at 80% confluence: WEH1-3 and Pu5-1.8 (myelomonocytes), P388D1 and IC-21 (macrophages), AKR.G.2 (thymoma), BaF3 (Pro B cell), EL-4 (Lymphoma), NFS-1.0 (B cell lymphoma), BCL (B cell leukemia), STO (embryonic fibroblasts), EOMA (endothelial), and BMS-12 (bone marrow stromal). Except for EOMA cells and BMS-12 cells, all of these cells were maintained according to procedures described by the American Type Culture Collection (Bethesda, Md.). EOMA cells were maintained in DMEM with 10% FCS, and BMS-12 cells were maintained in DMEM with 10% horse serum. In order to determine the effect of activators on neurotactin, cells were treated with 100 ng/ml LPS or 30 ng/ml PMA for 4 hours prior to RNA extraction or were left untreated.

Northern blots containing 20 μg of total RNA were probed using standard techniques (Chirgwin et al., *Biochemistry* 18:5294, 1979) with a $^{32}$P-labeled DNA fragment encoding the full-length neurotactin.

This Northern analysis revealed that a 3.5 kb neurotactin mRNA is constitutively expressed in endothelial cells (EOMA) and embryonic fibroblasts (STO). The 3.5 kb mRNA is upregulated in these cells when they are stimulated with LPS and PMA. This mRNA is also upregulated in bone marrow stromal cells (BMS-12) when treated with LPS and PMA. It is not expressed by unstimulated BMS-12 cells. This expression pattern is characteristic of modulators of inflammation.

Neurotactin mRNA was not detected in several cell lines of hematopoietic origin with or without stimulation by PMA and LPS. These cell lines were WEHI-3 and Pu5-1.8 (myelomonocytic), P388D1 and IC-21 (monocytic/macrophage), ARK.G.2 (thymoma), BaF3 (pro B cell), EL-4 (lymphoma), NFS-1.0 (B cell lymphoma) and BCL (B cell leukemia).

This same Northern analysis revealed the presence of messages having the following approximate sizes: 1.5 kb, 4.4 kb, and 5.5 kb. These messages are likely to represent alternatively spliced forms of neurotactin or the transcription products of related genes.

Human tissue Northern blots showed that human neurotactin is highly expressed in the brain and the heart. Furthermore, hybridization to a brain tissue Northern blot (Clontech) showed that the mRNA was expressed in all parts of the brain.

In situ hybridizations were also used to examine neurotactin expression. Tissues for these hybridization were prepared as follows. Four to six week old C57BL/6 mice were anesthetized and perfused with PBS followed by 4% paraformaldehyde (PFA/PBS). The brains were then removed and stored in 10% buffered formalin. Ten μm coronal frozen sections of brain were post-fixed with 4% PFA/PBS for 15 minutes. After washing with PBS, sections were digested with 2 μg/ml proteinase K at 37° for 15 minutes, and then incubated with 4% PFA/PBS for 10 minutes. Sections were then washed with PBS, incubated with 0.2 N HCl for 10 minutes, washed with PBS, incubated with 0.25% acetic anhydride/1 M triethanolamine for 10 minutes, washed with PBS, and dehydrated with 70% ethanol and 100% ethanol.

Hybridizations were performed with $^{35}$S-radiolabeled ($5\times10^7$ cpm/ml) antisense cRNA probes encoding a 1.9 kb segment of the coding region of the murine neurotactin gene (clone 6h11) in the presence of 50% formamide, 10% dextran sulfate, 1× Denhardt's solution, 600 mM NaCl, 10 mM DTT, 0.25% SDS, and 100 µg/ml tRNA for 18 hours at 55° C. After hybridization, the slides were washed with 5× SSC at 55° C., 50% formamide/2× SSC at 55° C. for 30 minutes, 10 mM Tris-HCl (pH 7.6)/500 mM NaCl/1 mM EDTA (TNE) at 37° C. for 10 minutes, incubated in 10 µg/ml RNase A in TNE at 37° C. for 30 minutes, washed in TNE at 37° C. for 10 minutes, incubated once in 2× SSC at 50° C. for 30 minutes, twice in 0.2× SSC at 50° C. for 30 minutes, and dehydrated with 70% ethanol and 100% ethanol. Localization of mRNA transcripts was detected by dipping slides in Kodak NBT-2 photoemulsion and exposed for 4 days at 4° C. Controls for the in situ hybridization experiments included the use of a sense probe which showed no signal above background levels.

These in situ hybridizations with murine neurotactin probe showed that neurotactin is expressed in the arcuate nucleus. Expression was also detected in the cortex and choroid plexus.

To determine the association of neurotactin with the cell membrane, a construct containing the full-length murine neurotactin coding region was made in a mammalian expression vector, pN83. Full-length murine neurotactin cDNA was modified for expression in a mammalian system by PCR with the following primers: 5'-GGGAAAGAATTCATG GCTCCCTCGCCGCTCGCGTCC-3' (SEQ ID NO:12) and 5'-GGGAAACTCGAGTCATTTATCATCATCATCTTTAT AATCCACTGGCACCAGGACGTATGA-3' (SEQ ID NO:13). Nucleotides encoding a FLAG epitope tag (DYKDDDDK (SEQ ID NO:14), which can be detected with an M2 anti-FLAG antibody, were incorporated into the 3' "reverse" primer. The PCR products were cloned into the pN83 vector bearing the EBV origin of replication. The construct DNA was prepared with the Qiagen Maxiprep™ kit (Qiagen, Chatsworth, Calif.) and transfected with lipofectamine™ (Gibco, Gaithersburg, Md.) into 293 EBNA cells that were cultured in 8-well chamber slides. Forty-eight hours after transfection, the cells were fixed with 50% methanol and 50% acetone for 1 minute at room temperature, washed four times with 2.5 ml TBS, and incubated with 10 µg/ml of M2 anti-FLAG monoclonal antibody (Eastman Kodak Co., New Haven, Conn.) and then with FITC-conjugated goat anti-mouse antibody at 1:1000 dilution (Jackson Immuno Research, West Grove, Pa.). The cells were exposed to the primary and secondary antibodies for one hour each. The immunofluorescent staining was visualized under 200-fold magnification. Strong staining was detected on the surface of the transfected 293 EBNA cells, suggesting full-length neurotactin is indeed membrane-anchored. The signal observed could be competed out by adding an excess of the FLAG peptide to the incubation.

Example 3

Preparation of Soluble Neurotactin

A soluble form of murine neurotactin (amino acids 22–105) was produced in bacteria using the pGEX expression system. The pGEX-neurotactin was purified on glutathione agarose and the neurotactin moiety released by thrombin digestion. Following endotoxin removal on an Endotoxin BX column (Cape Cod Associates: Falmouth, Mass.) the neurotactin preparation was determined to contain low levels of endotoxin (<0.01 EU/ml) by the Limulus amebocyte lysate (LAL) assay (Cape Cod Associates).

Soluble murine neurotactin (amino acids 22–105) was produced as follows. First, the coding region of murine neurotactin was amplified with a primer corresponding to a sequence at the 5' end of the sequence encoding the chemokine-like domain (5' primer). The 5' primer, 5'-GGGAAAGAATTCCTGCCGGGTCAGCACCTCGGC ATG-3' (SEQ ID NO:6), has an EcoRI restriction enzyme cleavage site followed by 24 nucleotides encoding the beginning of the chemokine-like domain of murine neurotactin. The 3' primer used was 5'-GGGAAACTCGA GTCATTCTCAAACTTGCCACCATTTTTA-3' (SEQ ID NO:7). This primer has complementary sequences encoding amino acids 99 to 105 preceded by a termination codon and XhoI site.

These primers pairs were used for PCR amplification using the following conditions: 94° C. for 30 seconds; 55° C. for 30 seconds and 72° C. for 90 seconds with 30 cycles. The resulting PCR product was cloned into the GST fusion protein vector pGEX-4T (Pharmacia, Piscataway, N.J.). The fusion protein was produced in E. coli and purified according to the protocol supplied by the manufacturer. The neurotactin construct produced a protein of approximately 10,000 kDa after the cleavage of GST by thrombin.

Example 4

Bacterially-expressed, Soluble Murine Neurotactin as a Chemoattractant

The ability the soluble murine neurotactin (amino acids 22–105) described above was tested for its ability to act as a chemoattractant for neutrophils.

The human neutrophils used in these experiments were isolated by layering 20 ml of human blood over 10 ml of FICCOL 1119 and 10 ml of FACIAL 1077 (Sigma; St Louis, Mo.) in a 50 ml conical polypropylene tube and centrifuging at 1800 rpm for 15 minutes at room temperature. Following centrifugation, the neutrophil layer was washed with sterile, ice cold, calcium and magnesium-free phosphate buffered saline (Gibco; Bethesda, Md.), and the neutrophil pellet was resuspended in 45 ml sterile, cold $H_2O$ and 5 ml sterile 10× phosphate buffered saline (PBS) to lyse contaminating red blood cells. The cells were pelleted by centrifugation at 1800 rpm for 5 minutes at 4° C. The pelleted neutrophils were resuspended in 10 ml of sterile PBS, quantitated, and kept on ice until needed for in vitro assays.

The ability of soluble murine neurotactin (amino acids 22–105) to elicit neutrophil chemotaxis was tested in an in vitro assay as described by Falk et al. (*J. Immunol. Meth.* 33:39, 1980). Approximately 50,000 neutrophils were added to each well of a 48-well micro chemotaxis chamber containing a 5 μm pore size filter. Varying concentrations of soluble murine neurotactin (amino acids 22–105) or human interleukin-8 (Biosource International, Camarillo, Calif.) were added to the lower chamber of each appropriate well. The cells were then incubated at 37° C., 5% $CO_2$ for 30 minutes. The upper chamber was removed and the cells on the filter from the upper chamber were removed by scraping. The filter was fixed in 100% ethanol and stained with a solution of 0.5% toluidine blue in 3.7% formaldehyde. Excess stain was removed with distilled water. Migrated cells were quantitated by counting three high power fields (400× magnification) per well. The number of cells that migrated to the buffer control were subtracted as background. The activities of compounds in this assay are predictive of the ability of compounds to elicit neutrophil chemotaxis in vivo.

Figure 5:
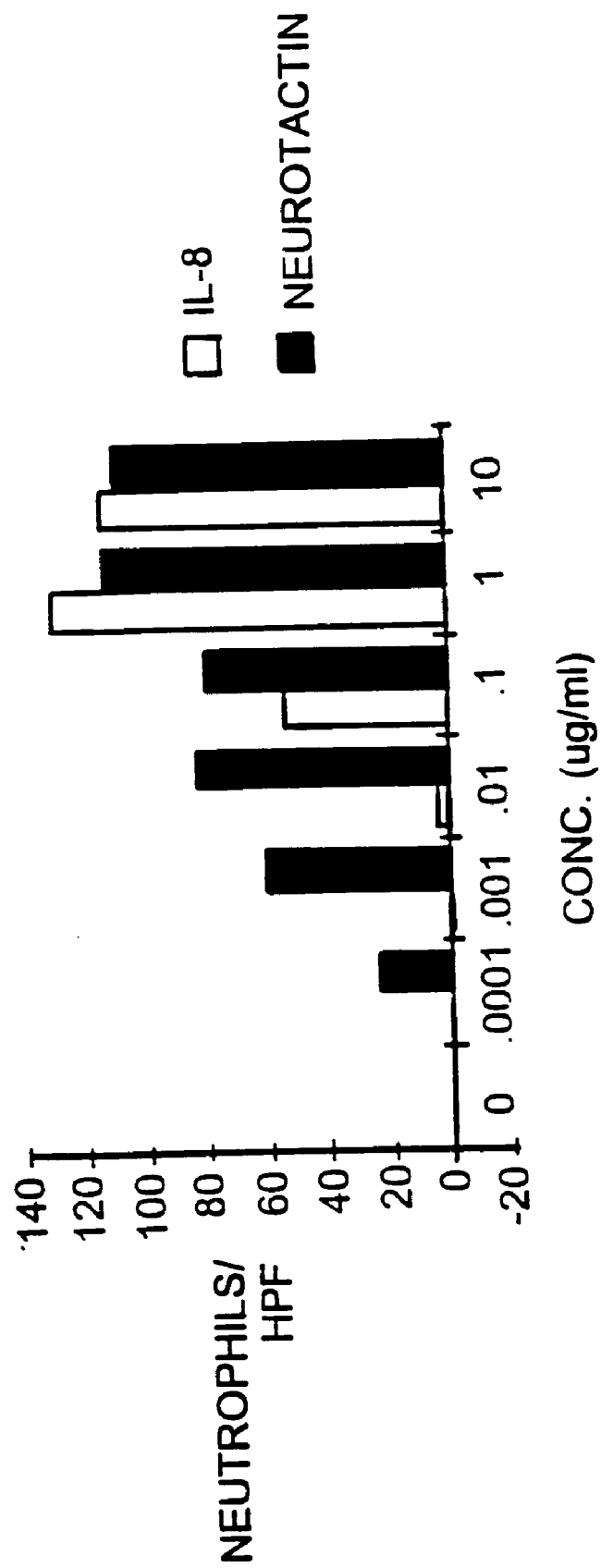
FIG. 5 is a graph illustrating the results of a neutrophil chemotaxis assay.

The results of this assay are presented in FIG. 5. This figure provides a comparison of the ability of human interleukin-8 and soluble murine neurotactin (amino acids 22–105) to elicit neutrophil chemotaxis. As can be seen in the figure, the soluble murine neurotactin is chemotactic for human neutrophils with an approximate endpoint titer (concentration giving 50% of the maximal stimulation level) of 1 ng/ml. This endpoint titer compares favorably with that of human interleukin-8, a known neutrophil chemoattractant.

The soluble murine neurotactin (amino acids 22–105) is also chemotactic for human T lymphocytes. However, further testing showed that neither this soluble murine neurotactin (amino acids 22–105) nor a second soluble form of murine neurotactin (amino acids 22–337) is chemotactic for human monocytes, human myelomonocytic THP-1 cells (ATCC TIB-202; Raport et al., *Gene* 163:295, 1995), murine P388D1 monocytic cells.

Two soluble forms of murine neurotactin (amino acids 22 to 105 or amino acids 22–337) were injected into C57BL/6J mice intraperitoneally to determine the chemotactic efficacy in vivo. Bacterial lysate containing only glutathione S-transferase was purified in the same fashion as these soluble forms of neurotactin and served as a control for the in vivo assay. Neurotactin and the control protein were both administered at a dose of 0.5 μg/400 μl PBS/mouse. In addition, some mice received only 400 μl of PBS. Two hours after the injection, peritoneal exudate was collected and the number and subtype of leukocytes recovered in the fluid were determined by typing and counting the cells in four high power fields (40× magnification; total area 0.5 mm$^2$). The neutrophils and eosinophils were identified by staining with Wright-Giemsa, and lymphocytes were assessed by Thy 1.2 (53-2.1) and IgM (II/41) immunostaining.

The smaller soluble murine neurotactin (amino acids 22 to 105) was chemotactic for neutrophils and lymphocytes (as predicted from in vitro studies), and was also chemotactic for monocytes. However, the activity of this soluble murine neurotactin towards monocytes may be due to a secondary effect in vivo and may not, therefore, reflect the chemotactic specificity of neurotactin. This soluble murine neurotactin was not chemotactic for eosinophils. The larger soluble murine neurotactin (amino acids 22 to 337) failed to act as a chemoattractant for monocytes and lymphocytes in vivo but was chemotactic for neutrophils.

Example 5

Neurotactin Expression Normal Mice, LPS-treated Mice, and Mice with Severe Experimental Autoimmune Encephalomyelitis Experimental autoimmune encephalomyel it is (EAE) is a mouse model of T cell mediated autoimmune disease that shares many clinical and histological features with multiple sclerosis. Central nervous system myelin is the target of an immune attack in multiple sclerosis, but the cellular and molecular mechanisms that lead to myelin breakdown have not been fully elucidated. Two major proteins of CNS myelin that can induce EAE are myelin basic protein (MBP) and proteolipid protein (PLP) (Zamvil and Steinman, *Annual Rev. Immunol* 8:579; 1990). It is generally thought that EAE is a delayed-type hypersensitivity (DTH) reaction. Although myelin antigen-specific Th1 cells are required to initiate the disease, most of the cells in the EAE lesions are non-specifically recruited. The infiltrating cells consist primarily of T cells and macrophages and, to a lesser extent, B cells. In some cases, polymorphs are also detected in EAE lesions (Sobel et al., *J. Neuropathol. Exp. Neurol.* 49:468, 1989). It is likely that the infiltrating cells play a major role in the tissue damage. Activated macrophages have been demonstrated to strip axons of myelin. In addition, activated macrophages secrete numerous cytokines, including IL-1 and TNF-α, nitric oxide, free oxygen radicals, and proteolytic enzymes, all of which can further perpetuate non-specific inflammatory reactions and contribute to tissue damage (Oppenheim and Gery, *Immunol. Today* 3:113, 1982; Scheurich et al., *J. Immunol.* 138:1786, 1987). Moreover, activated T cells produce proinflammatory chemotactic cytokines (chemokines), which play an important role in the non-specific recruitment of inflammatory cells (Oppenheim et al., *Annu. Rev. Inmmunol.* 9:617, 1991).

EAE can be induced by immunizing susceptible strains of mice with either proteins found in myelin (e.g., MBP or PLP) or with their peptides (Milner et al., *Cell* 42:931, 1985; Kuchroo et al., *J. Immunol.* 151:4371, 1985).

In addition, EAE develops spontaneously in immunodeficient α-myelin basic protein T cell receptor transgenic mice, which are used as a model of chronic inflammatory diseases.

Neurotactin expression in the brain was determined by immunohistochemistry in mice with severe experimental autoimmune encephalomyelitis (EAE), normal mice, and mice treated with LPS using a polyclonal anti-neurotactin antibody.

For these experiments, polyclonal anti-neurotactin antibody was raised in rabbits against a peptide located at the amino terminus of murine neurotactin (LPGQHLGMTKCEIM; SEQ ID NO:15; Research Genetics, Huntsville, Ala.). The antibody was affinity purified from 12-week bleeds. For LPS treatment, 8 week old CD1 mice were injected intravenously with 40 μg LPS and sacrificed 2 hours later by cervical dislocation. Their brains were removed, bisected transversely, and coated with Tissue Tek™ OCT compound (Cryoform). The OCT-coated tissue was then snap frozen in a mixture of isopentane and dry ice and stored at −70° C. Sections (3 μm thick) were cut onto microscope slides, air dried, fixed in 2% paraformaldehyde (for 5 minutes at 4° C.) and methanol (10 minutes at −20° C.). To study neurotactin expression in the EAE model, brains were collected from male α-myelin basic protein T cell receptor (MBP TCR) transgenic mice (at about 4 months of age) and fixed in 10% neutral buffered formalin and embedded in paraffin. Sections (4 μm) were microwaved twice for 5 minutes in 0.01 M sodium citrate (pH 6.0) before staining.

The fixed sections were stained with antibody using an avidin/biotin staining method. All incubations were carried out under humidified conditions and slides were washed twice between the steps for 5 minutes each in 0.1 M phosphate buffered saline supplemented with 0.2% gelatin (PBSG). The sections were overlaid with 20% fetal calf serum in PBS for 15 minutes and then incubated overnight at 4° C. with polyclonal anti-neurotactin or normal rabbit serum (both diluted to 1:200 in PBS supplemented with 0.1% bovine serum albumin). Endogenous peroxide was blocked by incubation for 20 minutes in methanol containing 0.3% hydrogen peroxide. Non-specific staining due to cross reaction with endogenous avidin or biotin was blocked by incubation with avidin solution followed by biotin solution, both for 20 minutes. Bound monoclonal antibody was visualized by incubation with biotinylated swine anti-rabbit immunoglobulin (Dako, Calif.) and then streptavidin peroxidase complex, both diluted in 10% normal mouse serum with PBS, and incubated for one hour. The slides were then flooded with peroxidase substrate solution (400 μg diaminobenzidine in 10 ml PBS containing 0.01% hydrogen peroxide) for 10 minutes. The sections were counterstained with haematoxylin. Control sections were generated by selectively omitting monoclonal antibody, biotinylated anti-rat immunoglobulin or streptavidin complex. In addition, competitive inhibition of the antibody was accomplished by preincubation of antibody with the peptide (25 μg/ml) for 45 minutes at 37° C. prior to incubation with the tissue sections.

In the normal mouse brain, staining was localized to capillary vessels and resident microglia. An increased intensity of labeling was observed on the same cell types two hours after LPS treatment. In addition, an increased number of activated microglial cells stained positive for the anti-neurotactin antibody. In both normal and LPS-treated brain, staining of larger vessels was restricted to the apical region of the endothelium. It is known that, in addition to resident microglial cells, two other subtypes of microglial cell are present in the CNS at the blood-brain barrier: perivascular and juxtavascular microglia. The anti-neurotactin antibody staining associated with capillary vessels was consistent with the staining of those microglial cells. Neurotactin expression was also up-regulated in activated microglial in the brains of EAE mice. The staining of both capillary vessels and microglial cells could be due to either direct neurotactin expression or expression of neurotactin repressor to which neurotactin in bound.

Example 6

Mapping of the Neurotactin Gene

Described in this example is the chromosome mapping of neurotactin. Also described below is the potential relationship between neurotactin and Bardet-Biedl Syndrome.
Mouse Chromosome Mapping The following PCR primers were used to amplify mouse genomic DNA.

Forward primer: 5'-CACAGTCCACCCCTCAG-3' (SEQ ID NO:8)

Reverse primer, 5'-GCTCTGGTAAGCAAACATGG-3' (SEQ ID NO:9).

PCR reactions were performed on genomic DNA from a panel of interspecific backcrossed mice. The amplification profile was as follows: 94° C. (30 seconds); 55° C. (30 seconds); and 72° C. (45 seconds) with 30 cycles. Samples were run on nondenaturing 10% acrylamide SSCP gel at 20 W and 4° C. for 2.5 hours.

Murine neurotactin was mapped to the long arm of mouse chromosome 8, between D8MIT35 and D8MIT74, by using a panel of backcrossed progeny of the C57Bl/6J and *Mus spretus*. The region is syntenic to human chromosome 16.
Human Chromosome Mapping Human neurotactin was mapped to chromosome 16q, between W17078 and WI6174, using a panel of radiation hybrids.

The following primers were used to amplify human genomic DNA from a panel of radiation hybrids (Genebridge 4, Research Genetics, Huntsville, Ala.).

Forward: 5'-TGTGAACTCCTCTGGCCTGT-3' (SEQ ID NO:10)

Reverse: 5'-GAAGGGGCTGGGCATTTAAT-3' (SEQ ID No:11) The amplification profile was as follows: 94° C. for 30 seconds; 55° C. for 30 seconds, and 72° C. for 45 seconds with 30 cycles. Samples were resolved on 1% agarose TEA gel.

Based on a published article (Kwitek-Black et al., *Nature Genetics* 5:392, 1993) and the integrated genetic map of Chromosome 16 (Genome Directory, *Nature* 377:335, 1995), the region to which neurotactin gene maps overlaps with a locus for the a gene important in Bardet-Biedl Syndrome (BBS).

BBS is a heterogeneous autosomal recessive disorder characterized by obesity, mental retardation, polydactyly, retinitis pigmentosa and hypogonadism. Patients suffering from this syndrome have a high incident of renal and cardiovascular abnormalities. The fact that neurotactin is expressed in tissues and organs which may be affected in BBS suggests that neurotactin may play a role in BBS. For example, BBS is characterized by obesity and mental retardation, and neurotactin is expressed in the arcuate nucleus, a region of the brain thought to play a role in weight control, and other parts of the brain. BBS is also associated with renal and cardiovascular symptoms, and neurotactin is expressed in the kidney and heart. In addition, BBS is associated with hypogonadism, and neurotactin is expressed in the uterus.

Example 7

Anti-Neuratactin Antibodies Slow the Progression of Experimental Autoimmune Encephalomyelitis The experiments described in this section demonstrate that anti-neurotactin antibodies can slow the progression of EAE in mice.
Generation of Anti-neurotactin Antibodies A fusion protein (GST-P3) consisting of nearly the entire extracellular domain of murine neurotactin (amino acids L22 to R337) was fused to GST was prepared as follows. DNA encoding the extracellular domain of murine neurotactin was constructed by PCR using modified oligonucleotides and Taq polymerase (Stratagene; La Jolla, Calif.). The forward primer was 5'-GGGAAAGAATTCCTGCCGG GTCAGCACCTCGGCATG-3' (SEQ ID NO:16) and the reverse primer was 5'-GGGAAACTCGAGTCACCTTGTGGCTGCCTG GGTGTCGGG-3' (SEQ ID NO:17). The PCR products were ligated to EcoRI/XhoI digested pGEX-4T (Pharmacia; Piscataway, N.J.) and the ligation products were used to transform *E. coli* DH5α (Life Technology; Gaithersburg, Md.). A clone encoding the desired soluble neurotactin fragment fused in frame to GST was identified. This clone was used to express the fusion protein, GST-P3 which was purified with glutathione-sepharose according to the manufacturer's instructions. Polyclonal anti-neurotactin antibody (anti-GST-P3) was raised in rabbits (Research Genetics) and the antibody was purified from serum by protein A chromatography.

In this experiment EAE mice were generated as follows. Female SJL mice (12 weeks of age) were immunized with 40 μg PLP peptide 139-151 (Prabhu et al., *J. Exp. Med.* 186:867, 1997; HSLGKWLGHPDKF; SEQ ID NO:18) in complete Freund's adjuvant (CFA). Pertussis toxin (400 ng/mouse) was also administered intravenously. Anti-neurotactin antibody was administered (30 μg/mouse) every other day. The disease course was followed for about a month. The control mice received 0.2 ml PBS every other day intravenously. The disease is scored as follows: 1=limp tail (tail atony); 2=hind limb weakness, no righting ability; 3=hind limb paralysis and incontinence; 4=all four limbs are paralyzed; and 5=moribund.

Figure 6:
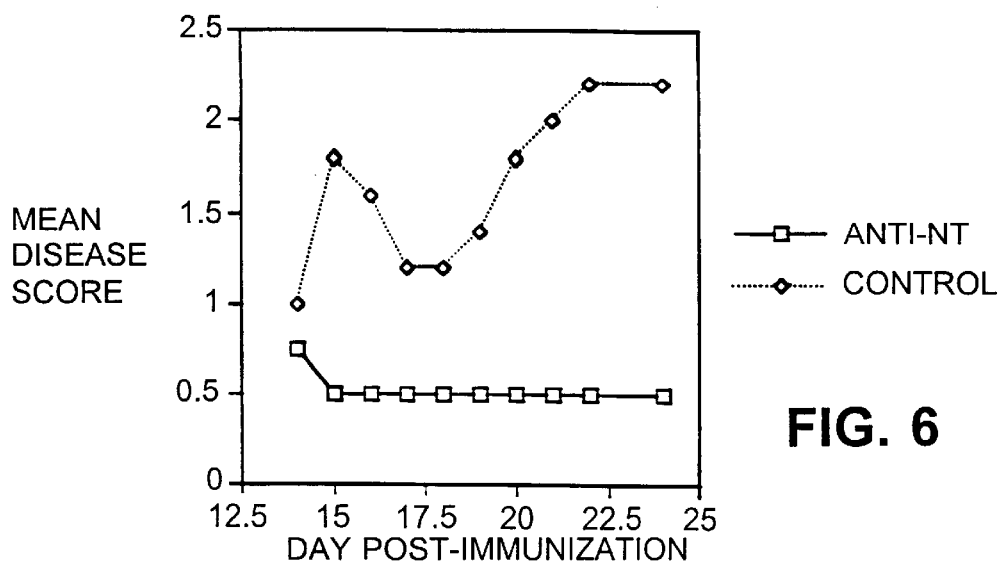
FIG. 6 is a graph demonstrating that an anti-neurotactin antibody can slow the progression of experimental autoimmune encephalomyelitis.

The results of this study are summarized in FIG. 6, which shows that the mean disease score for mice treated with antineurotactin antibody (anti-GST-P3; open squares) is considerably lower than the mean disease score for untreated mice (open diamonds).

Example 8

Neurotactin Distribution in the Brain

As discussed above, in situ hybridization studies carried out using a murine neurotactin probe revealed that neurotactin is expressed in the arcuate nucleus, the cortex, and the choroid plexus.

Additional in situ hybridizations studies were carried out on fresh frozen adult mouse brain. Sections of the hypothalamus, hippocampus, and cerebral cortex were examined using a cRNA probe specific for neurotactin. These studies revealed that neurotactin mRNA is expressed predominantly by neuronal cells.

Example 9

Neurotactin-Deficient Mice are Less Susceptible to Ischemia-Reperfusion Injury than Wild-Type Mice A neurotactin (NTN) knockout (KO) mouse line was generated by targeted gene-disruption using standard procedures. Briefly, two out of the three neurotactin exons were deleted by homologous recombination in 129/SvEv ES cells. The neurotactin exon remaining in the recombinant cells encodes only the neurotactin signal sequence. Using standard techniques, recombinant ES cells were injected into a mouse blastocyst to generate a chimeric embryo which was implanted into a pseudopregnant female foster mouse. The resulting chimeric mice were outbred with Balb/c ByJ mice to generate neurotactin –/– mice. Genomic DNA from neurotactin –/– mice was tested by Southern and Northern hybridization to verify that the neurotactin coding sequences had been deleted. No gross abnormality was found in any of the neurotactin –/– or +/– mice.

The role of neurotactin in inflammation following brain injury was tested using a standard model of ischemia-reperfusion model of brain injury and neurotactin –/– mice. These studies revealed that, following middle cerebral artery occlusion, neurotactin –/– mice were less susceptible to cerebral injury their wild-type litter mates. After 24 hours of reperfusion followed by two hours ischemia, the average infarct volume in neurotactin –/– mice was 50 mm$^3$ (n=4). The average infarct volume in the wild-type litter mates was over 80 mm$^3$ (n=3). These results suggest that neurotactin plays a role in brain ischemia and that neurotactin antagonists (e.g., neutralizing antibodies directed against neurotactin) may be useful in the treatment of stroke and other diseases involving neuronal damage.

Example 10

Anti-neurotactin Antibodies Prevent Relapsing Experimental Autoimmune Encephalomyelitis As described above in Example 7, anti-neurotactin antibodies can slow the progression of experimental autoimmune encephalomyelitis (EAE) in mice. In this example, anti-neurotactin antibodies were shown to prevent relapsing EAE in mice.

Female SJL mice (12–14 weeks old) were immunized with 100 μg PLP peptide 139-151 in complete Freund's adjuvant and pertussis toxin (400 ng/mouse) as described in Example 7. The mice were allowed to complete their first phase of disease and recover to a disease score of 0 or 1, at which time (day 16 post-immunization) they were injected intravenously with either 30 Mg polyclonal anti-neurotactin antibody (anti-GST-P3; see Example 7) or control rabbit Ig every other day. The development of EAE relapse was assessed by monitoring paralysis.

Figure 7:
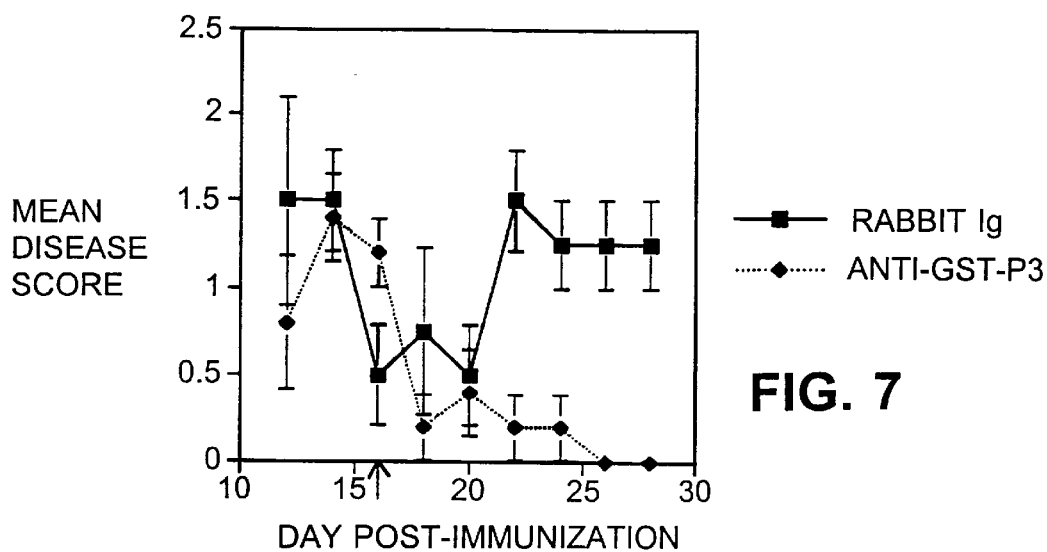
FIG. 7 is a graph demonstrating that an anti-neurotactin antibody can prevent relapse of experimental autoimmune encephalomyelitis.

As shown in FIG. 7, mice injected with control rabbit Ig began to relapse on day 22, reaching a mean disease score of between 1.2 and 1.3 through the end of the study. Mice treated with polyclonal anti-neurotactin antibody (anti-GST-P3) remained in remission (disease score below 0.5 through the end of the study).

These results further support the suggestion that inflammatory diseases of the central nervous system, e.g., multiple sclerosis, can be treated by administering an agent which reduces neurotactin activity or expression, e.g., an anti-neurotactin antibody.

Example 11

Production of Monoclonal Anti-Murine Neurotactin Antibodies

Anti-murine neurotactin antibodies were prepared by immunizing neurotactin –/– mice (prepared as described above in Example 9) with the murine neurotactin-GST fusion protein (GST-P3; amino acids 22–337 of murine neurotactin fused to GST) described in Example 7. The immunization and ELISA protocols were essentially those described above for the preparation of monoclonal anti-human neurotactin antibodies except that murine neurotactin was used in the ELISA measurements. Ninety anti-murine neurotactin monoclonal antibodies were analyzed. Of these, 30 cross-reacted with human neurotactin. Among the monoclonal antibodies which cross-react with human neurotactin. This analysis revealed that monoclonal antibody 5b1.4 binds human neurotactin with a $K_D$ of $1.23\times10^{-8}$ M (average of 5 analyses); and monoclonal antibody 5a11.5 binds human neurotactin with a $K_D$ of $1.21\times10^{-9}$ M (average of 5 analyses).

Example 12

Production of Monoclonal Anti-Human Neurotactin Antibodies

To prepare anti-human neurotactin antibodies, Balb/C mice are immunized with 50 μg of a human neurotactin peptide, preferably produced in mammalian cells and preferably including the chemokine-like domain (amino acids 22–105; R&D Systems; Minneapolis Minn.), four times over a period of eight weeks. The first immunization is intraperitoneal and includes Freund's complete adjuvant. The second and third immunizations are also interperitoneal and include Freund's incomplete adjuvant. The final immunization is intravenous and includes adjuvant. Four days after the last immunization, splenocytes are isolated and fused with SP2/0 cells as described previously to produce hybridomas. (Coligan et al., Current Protocols in Immunology, supra).

ELISA is used to screen anti-neurotactin monoclonal antibodies. Briefly, wells of NUNC 96-well Maxisorp plates are coated with 50 μl of a 10 μg/ml solution of human neurotactin polypeptide (R&D Systems; Minneapolis Minn.) in carbonate buffer. The wells are exposed to the polypeptide solution for at least four hours at 4° C. Next, 300 μl of blocking buffer (PBS+1% BSA) are added to each well for at least two hours. The wells are next washed four times with PBS/Tween 20.

Antibody activity is measured by adding a 50 μl aliquot of hybridoma culture supernatant to each prepared microliter well and incubating at 37° C. for one hour. The wells are then washed four times with PBS/Tween 20. Next, alkaline phophatase-conjugated second antibody (Jackson ImmunoResearch Laboratories; West Grove, Pa.), diluted 1:500 in PBS, is added to each well. After incubation at 37° C. for 30 min, the wells are washed four times with PBS/Tween 20. Alkaline phosphatase activity is measured using p-nitrophenylphosphate dissolved in diethanolamine buffer (Bio-Rad Laboratories, Inc.).

The procedures in this example can be used to generate and screen therapeutically and diagnostically useful anti-human neurotactin antibodies.

Example 13

Measurement of Neurotactin Binding to Target Cells

To test the ability of anti-neurotactin antibodies to block neurotactin binding to cells expressing a neurotactin receptor, neurotactin binding to THP-1 cells (human myleomonocytic cell line; ATCC TIB-202) was measured essentially as described by Wu et al. (J. Exp. Med 186:1373–1381, 1997).

Briefly, THP-1 cells, previously washed in PBS, were resuspended in PBS at a concentration of $1\times10^7$/ml. Approximately $5\times10^5$ cells were dispensed into a microfuge tube, spun down, and resuspended in 100 μl of 0.2 nM $^{125}$I labeled human neurotactin (amino acids 1–339 followed by KQNHHHHHH (SEQ ID NO:19) and expressed in mouse myeloma cell line NSO; R+D Systems; Minneapolis, Minn.; Cat# 365-FR-025).

The target cells were incubated for 60 minutes at room temperature in the presence of: (1) $^{125}$I labeled human neurotactin alone (human amino acids 1–339 fused to KQNHHHHH (SEQ ID NO:19); (2) $^{125}$I labeled human neurotactin and 1 mM unlabeled neurotactin (human amino acids 1–339 fused to KQNHHHHHH (SEQ ID NO:19); (3) $^{125}$I labeled human neurotactin and 1 mM murine neurotactin-GST fusion protein (GST-P3; murine amino acids 22–337 fused to GST); (4) $^{125}$I labeled human neurotactin and 1 mM control GST-fusion protein (a non-neurotactin cytokine fused to GST); (5) $^{125}$I labeled human neurotactin and 100 mg/ml rabbit polyclonal antibody raised against murine neurotactin-GST fusion protein (anti-GST-P3); (6) $^{125}$I labeled human neurotactin and 100 mg/ml rabbit polyclonal antibody raised against GST; (7) $^{125}$I labeled human neurotactin and culture supernatant from hybridoma cell line 5b1.4 producing an anti-murine neurotactin monoclonal antibody (hybridoma cells are grown in RPMI supplemented with 20% fetal bovine serum, HT, L-Glutamine, penicillin and streptomycin); (8) $^{125}$I labeled human neurotactin and culture supernatant from hybridoma cell line 5a11.5 producing an anti-murine neurotactin monoclonal antibody (hybridoma cells are grown in RPMI supplemented with 20% fetal bovine serum, HT, L-Glutamine, penicillin and streptomycin); or (9) $^{125}$I labeled human neurotactin and control hybridoma supernatant for 60 minutes at room temperature. The cells were then washed 3 times in 200 μl of wash buffer (50 mM HEPES, 1 mM $CaCl_2$, 5 mM $MgCl_2$, 0.5% BSA 0.5 M $NaCl_2$). Any label remaining in the cell pellet was counted. Counts were normalized for background non-specific binding. All experiments were carried out in duplicate or triplicate. The results of this analysis are presented in FIG. 8.

Figure 8:
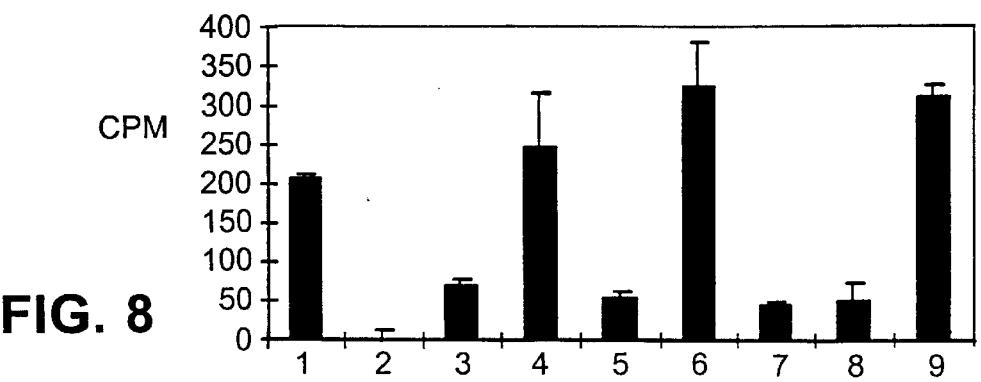
FIG. 8 is a graph illustrating the displacement of murine neurotactin (amino acids 1–339) by various anti-neurotactin antibodies and various forms of neurotactin.

As can be seen in FIG. 8, unlabeled human neurotactin, murine neurotactin-GST fusion protein, rabbit polyclonal antibody raised against murine neurotactin-GST fusion protein, and supernatant from monoclonal hybridoma cell lines 5b1.4 and 5a11.5 generated by immunization with murine neurotactin were shown to inhibit human neurotactin binding to THP-1 cells. Several other monoclonal antibodies generated by immunization with murine neurotactin-GST fusion protein (e.g., 4g8.1, 5b11.4, 9g4.11, 5b1.5, 2c3.8, and 5a11.9) were also shown to inhibit human neurotactin binding to THP-1 cells. This demonstrates that a number of the monoclonal anti-murine neurotactin antibodies cross-react with human neurotactin.

Example 14

Analysis of anti-Murine Neurotactin Antibody Binding to Human Neurotactin

The kinetics of binding of monoclonal antibodies 5b1.4 and 5a11.5 to immobilized human neurotactin (amino acids 1–339 fused to KQNHHHHHH (SEQ ID NO:19) expressed in mouse myeloma cell line Nso: R&D Systems, Inc) was measured a biosensor-based analytical system (Karlsson, et al., J. Immunol. Methods 145:229, 1991). This analysis revealed that monoclonal antibody 5b1.4 binds human neurotactin with a $K_D$ of $1.23\times10^{-8}$ M (average of 5 analyses); and monoclonal antibody 5a11.5 binds human neurotactin with a $K_D$ of $1.21\times10^{-9}$ M (average of 5 analyses).

Example 15

Displacement of Human Neurotactin from THP-1 Cells by Anti-Murine Neurotactin Monoclonal Antibodies The ability of monoclonal antibodies 5b1.4 and 5a11.5 to displace human neurotactin from THP-1 cells (ATCC TIB-202) was measured using a neurotactin-alkaline phosphatase fusion protein (amino acids 22–337 of human neurotactin fused to alkaline phosphatase; neurotactin-AP) produced in transiently transfected COS cells. Briefly, THP-1 cells were washed in PBS and resuspended in PBS at $10\times10^6$/ml. Fifty μl aliquots of cells were added to the wells of V-bottom 96 well plates. The plates were spun at 3200 rpm for 5 minutes and the supernatant was removed. Cells were resuspended in 50 μl of cell supernatant from transiently transfected COS cells producing neurotactin-AP (an amount selected by titration of neurotactin-AP binding to THP-1 cells) and hybridoma supernatant from anti-neurotactin antibody producing cells, hybridoma supernatant from control hybridomas, anti-GST-P3 antibody (described in Example 7), or human neurotactin polypeptide fragment (amino acids 22–92). The mixtures were incubated on ice for one hour and then for 30 minutes at room temperature. The cells were then washed four times with 250 μl PBS and resuspended in 40 μl of PBS. Neurotactin-AP binding was measured using the Phospha-Light™ chemiluminescent reporter gene assay system (Tropix, Inc.; Bedford, Mass.). The results of this analysis are presented in FIGS. 9a and 9b and 10.

Figure 9A:
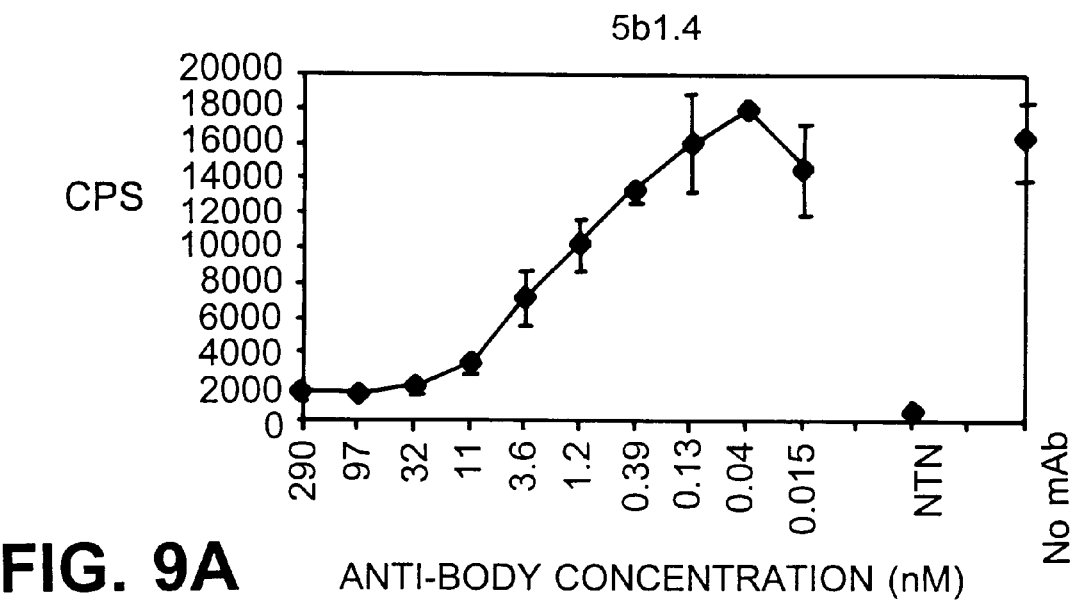
FIGS. 9A–9B are graphs illustrating the displacment of a human neurotactin-alkaline phosphatase fusion protein from THP-1 cells by monoclonal anti-murine neurotactin antibodies.
Figure 9B:
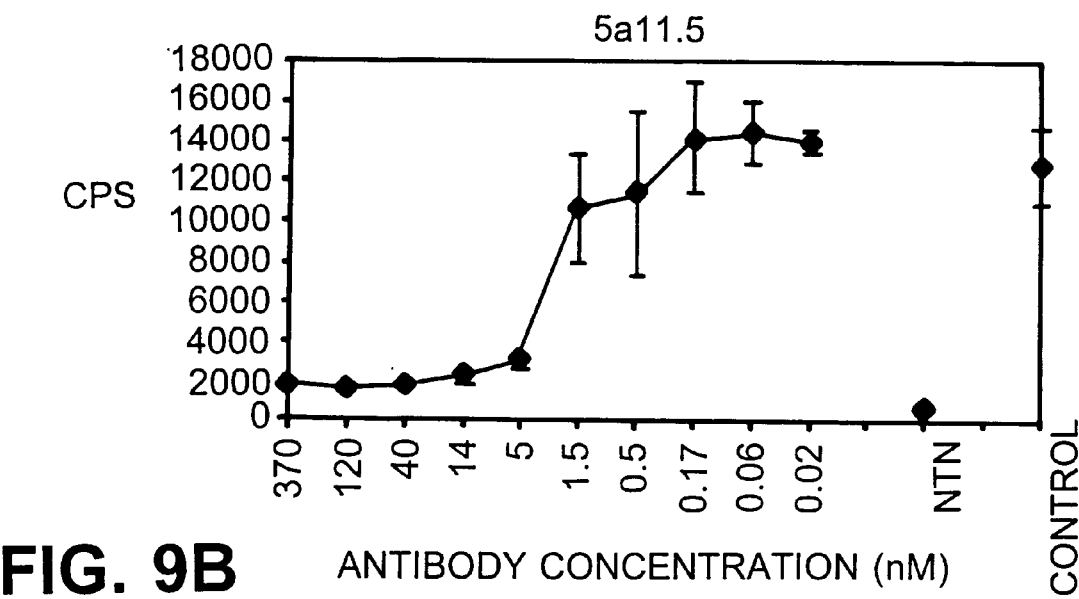
Figure 10:
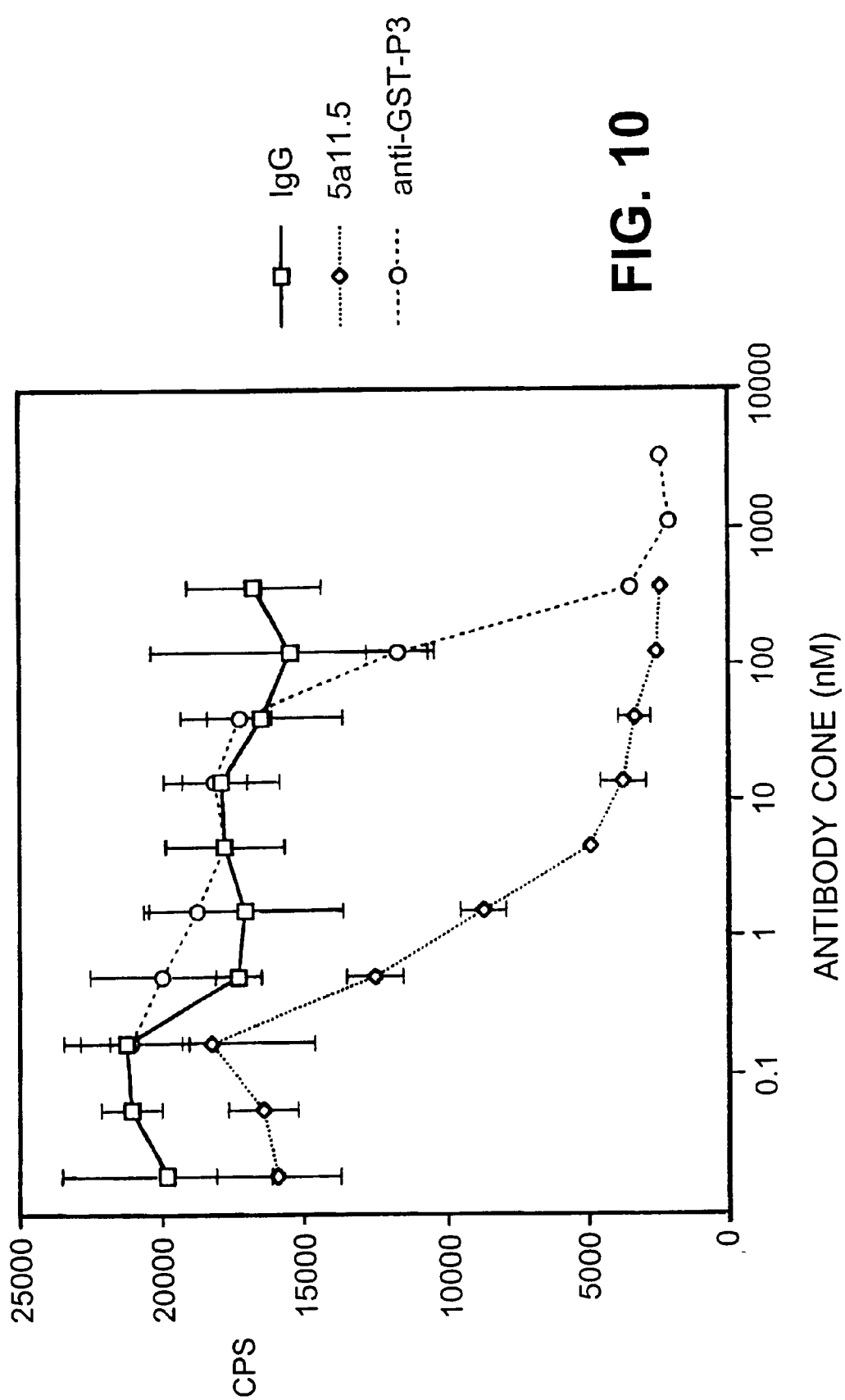
FIG. 10 is a graph illustrating displacment of a human neurotactin-alkaline phosphatase fusion protein from THP-1 cells by two different anti-murine neurotactin antibodies.

As shown in FIGS. 9A and 9B, both monoclonal antibody 5b1.4 and 5a11.5 effectively reduced binding of neurotactin-AP to THP-1 cells as did the human neurotactin fragment (NTN). FIG. 10 compares the ability of monoclonal antibody 5a11.5, anti-GST-P3, and a non-specific mouse Ig kappa control antibody to inhibit binding of neurotactin-AP to THP-1 cells. As can be seen from this figure, monoclonal antibody 5a11.5 effectively reduced binding of neurotactin- AP to THP-1 cells. The anti-GST-P3 antibody reduced binding, but only at much higher concentrations. The non-specific immunoglobulin was ineffective.

Example 16

Production of Human anti-Neurotactin Antibodies

Completely human anti-neurotactin antibodies (particularly anti-human neurotactin antibodies) are particularly desirable for therapeutic treatment of human patients. Such antibodies can be produced using transgenic mice which are incapable of expressing endogenous immunoglobulin heavy and light chains genes, but which can express human heavy and light chain genes. To produce human anti-neurotactin antibodies, the transgenic mice are immunized in the normal fashion with all or a portion of human neurotactin (preferably an extracellular portion thereof, e.g., all or a part of the chemokine-like domain). Monoclonal antibodies directed against neurotactin can be obtained from the immunized mice using conventional hybridoma technology. The human immunoglobulin transgenes harbored by the transgenic mice rearrange during B cell differentiation, and subsequently undergo class switching and somatic mutation. Thus, using such a technique, therapeutically useful IgG, IgA and IgE antibodies are produced.

For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. Nos. 5,625,126; U.S. Pat. No. 5,633,425; U.S. Pat. No. 5,569,825; U.S. Pat. No. 5,661,016; and U.S. Pat. No. 5,545,806.

Abgenix, Inc. (Freemont, Calif.) has produced transgenic mice (XenoMouse™) suitable for generating human antibodies. Such mice can be used to produce fully human anti-neurotactin antibodies.

Preferred anti-neurotactin antibodies bind the extracellular domain of neurotactin (amino acids 22–341). Within this region, antibodies which bind to the chemokine-like domain of neurotactin (about amino acid 22 to about amino acid 92 of SEQ ID NO:4; SEQ ID NO:20) are particularly desirable.

Preferred human anti-neurotactin antibodies are those which reduce the binding of neurotactin to cells bearing a neurotactin receptor. The assay described in Example 13 is suitable for identifying such antibodies. Also preferred are anti-neurotactin antibodies which inhibit neurotactin-stimulated chemotaxis. The assay described in Example 15 can be used to identify such antibodies. Both type of antibodies are expected to be useful in the treatment of disorders associated with inflammation of neuronal tissue or cells, e.g., stroke and multiple sclerosis.

Example 17

Measurement of Neurotactin-Stimulated Chemotaxis

Leukocyte chemotaxis stimulated by neurotactin can be assessed using a transendothelial assay (Qin et al., 1996, *Eur. Journal Immunol.*). Briefly, 24 hours before the assay, $2 \times 10^5$ endothelial cells (cell line ECV 304; ECACC, Porton Downs, UK) are cultured in M199, 10% FCS, L-glutamine, and antibiotics on 6.5 mm diameter (3.0 μm pore) Transwell culture inserts (Costar). A 24 well chemotaxis plate is prepared with an assay media that is equal parts RPMI 1640 and M199 with 0.5% BSA. Chemotactic factors, e.g., neurotactin, are added to the lower chambers of the wells of the chemotaxis plate in a final volume of 600 μl. The prepared endothelial cell-coated Transwell culture inserts are placed into each well and $10^6$ leukocytes are added to the top chamber in a final volume of 100 μl. The plate is then incubated at 37° C. in 5% $CO_2$/95% air for 1–4 hr, depending on the leukocyte type being studied. The cells that migrate to the lower chamber are counted using flow cytometry.

This assay can be used to identify inhibitors of neurotactin-stimulated chemotaxis of leukocytes and other cell types.

Example 18

Detection of Cell Surface Neurotactin

Immunofluorescent staining can be used to detect cell surface neurotactin and to screen antibodies for binding to neurotactin. To detect cell-surface neurotactin, $10^6$ cells are incubated with 50 μl of hybridoma supernatant from a hybridoma producing an murine anti-neurotactin antibody for 30 min at 4° C. The cells are then washed once and re-suspended in 50 μl of FITC-conjugated affinity purified $F(ab')_2$ goat anti-mouse IgG (Jackson Immunoresearch Labs, West Grove, Pa.). After a 30 min incubation at 4° C., the cells are washed twice and analyzed using a FACScan® (Becton Dickinson). Propidium iodide can be used to identify and exclude dead cells from analysis. For two-color immunofluorescence, cells are stained as described above and then stained with a PE-conjugated monoclonal antibody directed at a second target after first blocking with 20 μl of 10% normal mouse serum. After 30 min at 4° C., the cells are washed twice and analyzed by FACS.

Example 19

Treatment of Th1-associated Disorders

Neurotactin may play a role in Th1-associated immune disorders. Accordingly, anti-neurotactin antibodies and other inhibitors of neurotactin activity (or inhibitors of neurotactin expression) can be used to treat such disorders.

To determine whether anti-neurotactin antibodies can be used to treat rheumatoid arthritis, the SCID mouse-human rheumatoid arthritis model can be used (Oppenheimer-Marks et al., *J. Clin. Invest.* 101:126–72 (1998)).

To determine whether anti-neurotactin antibodies can be used to treat kidney nephritis, a murine model of the disorder can be used (Lloyd et al.,*J. Exp. Med.* 185:1371–80 (1997)).

Example 20

Therapeutic Applications

The neurotactin proteins and polypeptides described herein stimulate chemotaxis of neutrophils and lymphocytes. Accordingly, neurotactin proteins and polypeptides are likely to mediate inflammation. Consistent with this expectation is the fact that anti-neurotactin antibody slows the progression of EAE significantly. This suggests that anti-neurotactin antibodies and other inhibitors of neurotactin expression or activity can be used to treat other inflammatory disorders. Accordingly, undesirable inflammation of the brain associated with disorders such as viral encephalitis, multiple sclerosis, viral or bacterial meningitis, severe head trauma, stroke, neuro-degenerative diseases (e.g., Alzheimer's disease and Lou Gehrig's disease), HIV encephalopathy, primary brain tumors (e.g., glioblastomas), Lupus associated cerebritis, and post-seizure brain injury, can be reduced by the administration of a compound that interferes with neurotactin expression or function (e.g., an antibody). Compounds which interfere with neurotactin function may also be used to treat other undesirable inflammatory processes, e.g., atherosclerosis or respiratory infections.

Neurotactin, like other chemokines (Lord et al., *Blood* 85:3412, 1995; Laterveer et al., *Blood* 85:2269, 1995), can be used to mobilize hematopoietic stem cells and progenitor cells from the bone marrow to the peripheral blood. Because stem cells and progenitor cells can be more easily recovered from the peripheral blood than from bone marrow, neurotactin may be useful for isolating such cells for use in stem cell restorative therapy. Such therapy is useful for patients which have undergone myeloablative and/or myelosuppresive cancer treatments.

Neurotactin is likely to be involved in the regulation of hematopoietic cells. In particular, neurotactin, like other chemokines (Graham et al., *Nature* 344:442, 1994; Broxmeyer et al., *J. Immunol.* 150:3448, 1993), may be able to inhibit proliferation of hematopoietic stem cells and progenitor cells. Such inhibition can protect the cells from chemotherapeutic damage. Thus, neurotactin can be used to protect hematopoietic stem cells and progenitor cells from chemotherapeutic damage, e.g., damage during chemotherapy for cancer.

The neurotactin polypeptides which inhibit progenitor cell proliferation can be used to inhibit hyperproliferative myeloid based diseases such as chronic myelogenous leukemia, polycythemia vera, and hypermegakaryocytopoietic disorders. Hyperproliferative states in such disorders occur because the progenitor cells are unable to negatively regulate cell growth and replication. Administration of suitable neurotactin polypeptides is expected to inhibit cell replication resulting in the inhibition of the abnormal cell growth. Dosages of the neurotactin polypeptides for treating hyperproliferative myeloid based diseases would be similar to those dosages described above for use of the proteins as adjuncts to chemotherapy.

In addition, neurotactin polypeptides can be used to prevent myeloid progenitor cells from becoming leukemic as the result of the administration of chemotherapeutic agents. The neurotactin polypeptides are administered in the same way described above.

Recombinant neurotactin may facilitate the production of pharmacologic modifiers of neurotactin function. Such therapeutic polypeptides of the invention can be administered by any appropriate route, e.g., intravenously, at a dosage that is effective to modulate neurotactin function. Treatment may be repeated as necessary for alleviation of disease symptoms.

As noted above, agents which inhibit neurotactin activity, e.g., anti-neurotactin antibodies, can be used to treat a variety of disorders, e.g., disorders associated with inflammation (e.g., atherosclerosis or respiratory infections), particularly within the brain. Accordingly, undesirable inflammation of the brain associated with disorders such as viral encephalitis, multiple sclerosis, viral or bacterial meningitis, severe head trauma, stroke, neurodegenerative diseases (e.g., Alzheimer's disease and Lou Gehrig's disease), HIV encephalopathy, primary brain tumors (e.g., glioblastomas), Lupus associated cerebritis, and postseizure brain injury, can be reduced by the administration of a compound that interferes with neurotactin expression or function (e.g., an antibody).

In therapeutic applications, anti-neurotactin antibodies, like other therapeutic antibodies, are administered parenterally, preferably intravenously or intramuscularly daily, monthly, biweekly, weekly, or more frequently. The preferred dosage is 0.1 mg/kg to 100 mg/kg of body weight, preferably 10 to 20 mg/kg of body weight. Dosages of 50 mg/kg or higher are preferred if the antibody is to be effective within the brain. The preferred dosage for treatment of a particular disorder can be based on results observed with other therapeutic antibodies or it can be determined by one skilled based on testing in animal models. The suitable dosage of antibody in a given situation depends on the disease being treated, the severity of the disease, whether the antibody is being administered for therapeutic or preventative reasons, previous therapies administered, and the patient's clinical history. Treatment is generally continued until the desired therapeutic or preventative effect is observed. Dosage regimes of the type that can be adapted to the methods of the present invention are found in PCT Publication No. WO 94/04188.

Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation is described by Cruikshank et al. (*J. Acquired Immune Deficiency Syndromes and Human Retrovirology*, 14:193, 1997)

Example 21

Diagnostic Applications

The nucleic acids, polypeptides, and antibodies of the invention are useful for identifying those compartments of mammalian cells which contain proteins important to the function of neurotactin. Antibodies specific for neurotactin may be produced as described above. The normal subcellular location of the protein is then determined either in situ or using fractionated cells by any standard immunological or immunohistochemical procedure (see, e.g., Ausubel et al., supra; Bancroft and Stevens, *Theory and Practice of Histological Techniques*, Churchill Livingstone, 1982).

Antibodies specific for neurotactin also find diagnostic use in the detection or monitoring of neurotactin-related diseases. Levels of a neurotactin protein in a sample can be assayed by any standard technique. For example, neurotactin protein expression can be monitored by standard immunological or immunohistochemical procedures (e.g., those described above) using the antibodies described herein. Alternatively, neurotactin expression can be assayed by standard Northern blot analysis or can be aided by PCR (see, e.g., Ausubel et al., supra; *PCR Technology: Principles and Applications for DNA Amplification*, ed., H. A. Ehrlich, Stockton Press, N.Y.). If desired or necessary, analysis can be carried out to detect point mutations in the neurotactin sequence (for example, using well known nucleic acid mismatch detection techniques). All of the above techniques are enabled by the neurotactin sequences described herein.

Accordingly, the nucleic acids, polypeptides and antibodies of the invention can be used in a method for determining whether a patient has a disorder associated with abnormal expression of neurotactin. The method can be carried out by quantitating the level of expression of neurotactin in a biological sample obtained from the patient. As a control, the quantitation can be carried out using a biological sample obtained from a patient who is healthy.

Neurotactin expression can be assessed at the level of gene expression, for example, by quantitating the level of neurotactin mRNA expression in the biological sample, or at the level of protein expression, by quantitating the level of neurotactin protein expressed. Quantitation can be carried out using the techniques described above, which are well within the abilities of those of skill in the art to perform.

Should it be determined that a patient has a disorder that is associated with abnormal expression or activity of neurotactin, the patient can be given a compound that modulates is that expression or activity. For example, the patient can receive a compound such as a small molecule, an antisense nucleic acid molecule, or a ribozyme, that inhibits the expression of neurotactin. The patient can also receive a compound that inhibits the activity of neurotactin. An antibody that specifically binds neurotactin can be used for this purpose. Alternatively, the patient can receive a compound that enhances the expression or activity of neurotactin. Compounds that inhibit or enhance the expression or activity of neurotactin can include synthetic molecules. These methods of treatment can be used to treat inflammatory disorders and disorders associated with cellular proliferation, as described more fully above.

The following hybridomas were deposited with the American Type Culture Collection (ATCC) 10801 University Boulevard, Manassas, Va., on the dates indicated and were assigned the indicated accession number:

Hybridoma Accession Number Date of Deposit
M7 5b1.4 HB-12555 Aug. 12, 1998
5a11.5 HB-12556 Aug. 12, 1998

Other Embodiments

The invention also features fragments, variants, analogs and derivatives of the neurotactin polypeptides described above that retain one or more of the biological activities of neurotactin such as neutrophil chemotaxis.

The invention includes naturally-occurring and non-naturally-occurring allelic variants. Compared to the most common naturally-occurring nucleotide sequence encoding neurotactin, the nucleic acid sequence encoding allelic variants may have a substitution, deletion, or addition of one or more nucleotides. The preferred allelic variants are functionally equivalent to naturally-occurring neurotactin.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

SEQUENCE LISTING

<160> NUMBER OF SEQ ID NOS: 20

<210> SEQ ID NO 1
<211> LENGTH: 1784
<212> TYPE: DNA
<213> ORGANISM: Mus musculus
<220> FEATURE:
<221> NAME/KEY: CDS
<222> LOCATION: (40)...(1224)

<400> SEQUENCE: 1

```
gtcgacccac gcgtccggcc gaattcctgc actccagcc atg gct ccc tcg ccg        54
                                           Met Ala Pro Ser Pro
                                             1               5 ctc gcg tgg ctg ctg cgc ctg gcc gcg ttc ttc cat ttg tgt act ctg       102
Leu Ala Trp Leu Leu Arg Leu Ala Ala Phe Phe His Leu Cys Thr Leu
                 10                  15                  20 ctg ccg ggt cag cac ctc ggc atg acg aaa tgc gaa atc atg tgc gac       150
Leu Pro Gly Gln His Leu Gly Met Thr Lys Cys Glu Ile Met Cys Asp
             25                  30                  35 aag atg acc tca cga atc cca gtg gct ttg ctc atc cgc tat cag cta       198
Lys Met Thr Ser Arg Ile Pro Val Ala Leu Leu Ile Arg Tyr Gln Leu
         40                  45                  50 aac cag gag tcc tgc ggc aag cgt gcc att gtc ctg gag acg aca cag       246
Asn Gln Glu Ser Cys Gly Lys Arg Ala Ile Val Leu Glu Thr Thr Gln
     55                  60                  65 cac aga cgc ttc tgt gct gac ccg aag gag aaa tgg gtc caa gac gcc       294
His Arg Arg Phe Cys Ala Asp Pro Lys Glu Lys Trp Val Gln Asp Ala
 70                  75                  80                  85 atg aag cat ctg gat cac cag gct gct gcc ctc act aaa aat ggt ggc       342
Met Lys His Leu Asp His Gln Ala Ala Ala Leu Thr Lys Asn Gly Gly
                 90                  95                 100 aag ttt gag aag cgg gtg gac aat gtg aca cct ggg atc acc ttg gcc       390
Lys Phe Glu Lys Arg Val Asp Asn Val Thr Pro Gly Ile Thr Leu Ala
            105                 110                 115
```

```
act agg gga ctg tcc cca tct gcc ctg aca aag cct gaa tcc gcc aca       438
Thr Arg Gly Leu Ser Pro Ser Ala Leu Thr Lys Pro Glu Ser Ala Thr
        120                 125                 130 ttg gaa gac ctt gct ttg gaa ctg act act att tcc cag gag gcc agg       486
Leu Glu Asp Leu Ala Leu Glu Leu Thr Thr Ile Ser Gln Glu Ala Arg
135                 140                 145 ggg acc atg ggg act tcc caa gag cca ccg gca gca gtg acc gga tca       534
Gly Thr Met Gly Thr Ser Gln Glu Pro Pro Ala Ala Val Thr Gly Ser
150                 155                 160                 165 tct ctc tca act tcc gag gca cag gat gca ggg ctt acg gct aag cct       582
Ser Leu Ser Thr Ser Glu Ala Gln Asp Ala Gly Leu Thr Ala Lys Pro
                170                 175                 180 cag agc att gga agt ttt gag gcg gct gac atc tcc acc acc gtt tgg       630
Gln Ser Ile Gly Ser Phe Glu Ala Ala Asp Ile Ser Thr Thr Val Trp
                185                 190                 195 ccg agt cct gct gtc tac caa tct gga tct agc tcc tgg gct gag gaa       678
Pro Ser Pro Ala Val Tyr Gln Ser Gly Ser Ser Ser Trp Ala Glu Glu
                200                 205                 210 aaa gct act gag tcc ccc tcc act aca gcc cca tct cct cag gtg tcc       726
Lys Ala Thr Glu Ser Pro Ser Thr Thr Ala Pro Ser Pro Gln Val Ser
215                 220                 225 act act tca cct tca acc cca gag gaa aat gtt ggg tcc gaa ggc caa       774
Thr Thr Ser Pro Ser Thr Pro Glu Glu Asn Val Gly Ser Glu Gly Gln
230                 235                 240                 245 ccc cca tgg gtc cag gga cag gac ctc agt cca gag aag tct cta ggg       822
Pro Pro Trp Val Gln Gly Gln Asp Leu Ser Pro Glu Lys Ser Leu Gly
                250                 255                 260 tct gag gag ata aac cca gtt cat act gat aat ttc cag gag agg ggg       870
Ser Glu Glu Ile Asn Pro Val His Thr Asp Asn Phe Gln Glu Arg Gly
                265                 270                 275 cct ggc aac aca gtc cac ccc tca gtg gct ccc atc tcc tct gaa gag       918
Pro Gly Asn Thr Val His Pro Ser Val Ala Pro Ile Ser Ser Glu Glu
                280                 285                 290 acc ccc agc cca gag ctg gtg gcc tcg ggc agc cag gct cct aag ata       966
Thr Pro Ser Pro Glu Leu Val Ala Ser Gly Ser Gln Ala Pro Lys Ile
295                 300                 305 gag gaa ccc atc cat gcc act gca gat ccc cag aaa ctg agt gtg ctt      1014
Glu Glu Pro Ile His Ala Thr Ala Asp Pro Gln Lys Leu Ser Val Leu
310                 315                 320                 325 atc act cct gtc ccc gac acc cag gca gcc aca agg agg cag gca gtg      1062
Ile Thr Pro Val Pro Asp Thr Gln Ala Ala Thr Arg Arg Gln Ala Val
                330                 335                 340 ggg cta ctg gct ttc ctt ggt ctt ctt ttc tgc cta ggg gtg gcc atg      1110
Gly Leu Leu Ala Phe Leu Gly Leu Leu Phe Cys Leu Gly Val Ala Met
                345                 350                 355 ttt gct tac cag agc ctt cag ggc tgt ccc cgc aaa atg gcg ggg gaa      1158
Phe Ala Tyr Gln Ser Leu Gln Gly Cys Pro Arg Lys Met Ala Gly Glu
                360                 365                 370 atg gta gaa ggc ctc cgc tac gtc ccc cgt agc tgt ggc agt aac tca      1206
Met Val Glu Gly Leu Arg Tyr Val Pro Arg Ser Cys Gly Ser Asn Ser
        375                 380                 385 tac gtc ctg gtg cca gtg tgagctgctt gcctgcctgc ctgtgtccag             1254
Tyr Val Leu Val Pro Val
390                 395 agtgtgattc ggacagctgt ctggggaccc cccccatcc tcatacccac cttcatccac     1314
gctggggaaa tgggaatgga gaagctggac cctccagggg ctgtgggctc catccaatcc    1374
cccctccccc gagggtggc cccggaggcc accctagacc actattcact tatcagagac     1434
```

```
agagcaggtg accttccagc tcctctatat ttgaaagaat cctctgctgc tggctggtta       1494
gaggggccct tgacacccca actccagtga acaattattt attggattcc cagcccctgc       1554
gacgacacct gtttcccgcg cgcaccgtgg tccgcccata tcacaagcag caggccaggc       1614
ctatctgcct gtcccctga cctccttgtg tctcctggct ttgctgcagt cgccagccct        1674
tctcctcccc ggccagctgc ggtgctatct gccctatgtc tccctctatc ccctgtacag       1734
agcgcaccac catcaccatc aaaaaaaaaa aaaaaaaaa gggcggccgc                   1784
```

<210> SEQ ID NO 2
<211> LENGTH: 395
<212> TYPE: PRT
<213> ORGANISM: Mus musculus

<400> SEQUENCE: 2

```
Met Ala Ser Pro Leu Ala Trp Leu Leu Arg Leu Ala Ala Phe Phe
 1               5                  10                  15

His Leu Cys Thr Leu Leu Pro Gly Gln His Leu Gly Met Thr Lys Cys
            20                  25                  30

Glu Ile Met Cys Asp Lys Met Thr Ser Arg Ile Pro Val Ala Leu Leu
        35                  40                  45

Ile Arg Tyr Gln Leu Asn Gln Glu Ser Cys Gly Lys Arg Ala Ile Val
    50                  55                  60

Leu Glu Thr Thr Gln His Arg Arg Phe Cys Ala Asp Pro Lys Glu Lys
65                  70                  75                  80

Trp Val Gln Asp Ala Met Lys His Leu Asp His Gln Ala Ala Leu
                85                  90                  95

Thr Lys Asn Gly Gly Lys Phe Glu Lys Arg Val Asp Asn Val Thr Pro
            100                 105                 110

Gly Ile Thr Leu Ala Thr Arg Gly Leu Ser Pro Ser Ala Leu Thr Lys
        115                 120                 125

Pro Glu Ser Ala Thr Leu Glu Asp Leu Ala Leu Glu Leu Thr Thr Ile
    130                 135                 140

Ser Gln Glu Ala Arg Gly Thr Met Gly Thr Ser Gln Glu Pro Pro Ala
145                 150                 155                 160

Ala Val Thr Gly Ser Ser Leu Ser Thr Ser Glu Ala Gln Asp Ala Gly
                165                 170                 175

Leu Thr Ala Lys Pro Gln Ser Ile Gly Ser Phe Glu Ala Ala Asp Ile
            180                 185                 190

Ser Thr Thr Val Trp Pro Ser Pro Ala Val Tyr Gln Ser Gly Ser Ser
        195                 200                 205

Ser Trp Ala Glu Glu Lys Ala Thr Glu Ser Pro Ser Thr Thr Ala Pro
    210                 215                 220

Ser Pro Gln Val Ser Thr Thr Ser Pro Ser Thr Pro Glu Glu Asn Val
225                 230                 235                 240

Gly Ser Glu Gly Gln Pro Pro Trp Val Gln Gly Gln Asp Leu Ser Pro
                245                 250                 255

Glu Lys Ser Leu Gly Ser Glu Glu Ile Asn Pro Val His Thr Asp Asn
            260                 265                 270

Phe Gln Glu Arg Gly Pro Gly Asn Thr Val His Pro Ser Val Ala Pro
        275                 280                 285

Ile Ser Ser Glu Glu Thr Pro Ser Pro Glu Leu Val Ala Ser Gly Ser
    290                 295                 300

Gln Ala Pro Lys Ile Glu Glu Pro Ile His Ala Thr Ala Asp Pro Gln
305                 310                 315                 320
```

-continued

```
Lys Leu Ser Val Leu Ile Thr Pro Val Pro Asp Thr Gln Ala Ala Thr
                325                 330                 335
Arg Arg Gln Ala Val Gly Leu Leu Ala Phe Leu Gly Leu Leu Phe Cys
            340                 345                 350
Leu Gly Val Ala Met Phe Ala Tyr Gln Ser Leu Gln Gly Cys Pro Arg
        355                 360                 365
Lys Met Ala Gly Glu Met Val Glu Gly Leu Arg Tyr Val Pro Arg Ser
    370                 375                 380
Cys Gly Ser Asn Ser Tyr Val Leu Val Pro Val
385                 390                 395

<210> SEQ ID NO 3
<211> LENGTH: 1654
<212> TYPE: DNA
<213> ORGANISM: Homo sapiens
<220> FEATURE:
<221> NAME/KEY: CDS
<222> LOCATION: (86)...(1276)

<400> SEQUENCE: 3
aagcttggca cgagggcact gagctctgcc gcctggctct agccgcctgc ctggcccccg      60
ccgggactct tgcccaccct cagcc atg gct ccg ata tct ctg tcg tgg ctg     112
                              Met Ala Pro Ile Ser Leu Ser Trp Leu
                                1               5 ctc cgc ttg gcc acc ttc tgc cat ctg act gtc ctg ctg gct gga cag     160
Leu Arg Leu Ala Thr Phe Cys His Leu Thr Val Leu Leu Ala Gly Gln
 10                  15                  20                  25 cac cac ggt gtg acg aaa tgc aac atc acg tgc agc aag atg aca tca     208
His His Gly Val Thr Lys Cys Asn Ile Thr Cys Ser Lys Met Thr Ser
                 30                  35                  40 aag ata cct gta gct ttg ctc atc cac tat caa cag aac cag gca tca     256
Lys Ile Pro Val Ala Leu Leu Ile His Tyr Gln Gln Asn Gln Ala Ser
             45                  50                  55 tgc ggc aaa cgc gca atc atc ttg gag acg aga cag cac agg ctg ttc     304
Cys Gly Lys Arg Ala Ile Ile Leu Glu Thr Arg Gln His Arg Leu Phe
         60                  65                  70 tgt gcc gac ccg aag gag caa tgg gtc aag gac gcg atg cag cat ctg     352
Cys Ala Asp Pro Lys Glu Gln Trp Val Lys Asp Ala Met Gln His Leu
     75                  80                  85 gac cgc cag gct gct gcc cta act cga aat ggc ggc acc ttc gag aag     400
Asp Arg Gln Ala Ala Ala Leu Thr Arg Asn Gly Gly Thr Phe Glu Lys
 90                  95                 100                 105 cag atc ggc gag gtg aag ccc agg acc acc cct gcc gcc ggg gga atg     448
Gln Ile Gly Glu Val Lys Pro Arg Thr Thr Pro Ala Ala Gly Gly Met
                110                 115                 120 gac gag tct gtg gtc ctg gag ccc gaa gcc aca ggc gaa agc agt agc     496
Asp Glu Ser Val Val Leu Glu Pro Glu Ala Thr Gly Glu Ser Ser Ser
            125                 130                 135 ctg gag ccg act cct tct tcc cag gaa gca cag agg gcc ctg ggg acc     544
Leu Glu Pro Thr Pro Ser Ser Gln Glu Ala Gln Arg Ala Leu Gly Thr
        140                 145                 150 tcc cca gag ctg ccg acg ggc gtg act ggt tcc tca ggg acc agg ctc     592
Ser Pro Glu Leu Pro Thr Gly Val Thr Gly Ser Ser Gly Thr Arg Leu
    155                 160                 165 ccc ccg acg cca aag gct cag gat gga ggg cct gtg ggc acg gag ctt     640
Pro Pro Thr Pro Lys Ala Gln Asp Gly Gly Pro Val Gly Thr Glu Leu
170                 175                 180                 185 ttc cga gtg cct ccc gtc tcc act gcc gcc acg tgg cag agt tct gct     688
Phe Arg Val Pro Pro Val Ser Thr Ala Ala Thr Trp Gln Ser Ser Ala
```

```
                    190                 195                 200
ccc cac caa cct ggg ccc agc ctc tgg gct gag gca aag acc tct gag       736
Pro His Gln Pro Gly Pro Ser Leu Trp Ala Glu Ala Lys Thr Ser Glu
            205                 210                 215 gcc ccg tcc acc cag gac ccc tcc acc cag gcc tcc act gcg tcc tcc       784
Ala Pro Ser Thr Gln Asp Pro Ser Thr Gln Ala Ser Thr Ala Ser Ser
            220                 225                 230 cca gcc cca gag gag aat gct ccg tct gaa ggc cag cgt gtg tgg ggt       832
Pro Ala Pro Glu Glu Asn Ala Pro Ser Glu Gly Gln Arg Val Trp Gly
        235                 240                 245 cag gga cag agc ccc agg cca gag aac tct ctg gag cgg gag gag atg       880
Gln Gly Gln Ser Pro Arg Pro Glu Asn Ser Leu Glu Arg Glu Glu Met
250                 255                 260                 265 ggt ccc gtg cca gcg cac acg gat gcc ttc cag gac tgg ggg cct ggc       928
Gly Pro Val Pro Ala His Thr Asp Ala Phe Gln Asp Trp Gly Pro Gly
                270                 275                 280 agc atg gcc cac gtc tct gtg gtc cct gtc tcc tca gaa ggg acc ccc       976
Ser Met Ala His Val Ser Val Val Pro Val Ser Ser Glu Gly Thr Pro
            285                 290                 295 agc agg gag cca gtg gct tca ggc agc tgg acc cct aag gct gag gaa      1024
Ser Arg Glu Pro Val Ala Ser Gly Ser Trp Thr Pro Lys Ala Glu Glu
        300                 305                 310 ccc atc cat gcc acc atg gac ccc cag agg ctg ggc gtc ctt atc act      1072
Pro Ile His Ala Thr Met Asp Pro Gln Arg Leu Gly Val Leu Ile Thr
315                 320                 325 cct gtc cct gac gcc cag gct gcc acc cgg agg cag gcg gtg ggg ctg      1120
Pro Val Pro Asp Ala Gln Ala Ala Thr Arg Arg Gln Ala Val Gly Leu
330                 335                 340                 345 ctg gcc ttc ctt ggc ctc ctc ttc tgc ctg ggg gtg gcc atg ttc acc      1168
Leu Ala Phe Leu Gly Leu Leu Phe Cys Leu Gly Val Ala Met Phe Thr
                350                 355                 360 tac cag agc ctc cag ggc tgc cct cga aag atg gca gga gag atg gcg      1216
Tyr Gln Ser Leu Gln Gly Cys Pro Arg Lys Met Ala Gly Glu Met Ala
            365                 370                 375 gag ggc ctt cgc tac atc ccc cgg agc tgt ggt agt aat tca tat gtc      1264
Glu Gly Leu Arg Tyr Ile Pro Arg Ser Cys Gly Ser Asn Ser Tyr Val
        380                 385                 390 ctg gtg ccc gtg tgaactcctc tggcctgtgt ctagttgttt gattcagaca          1316
Leu Val Pro Val
        395 gctgcctggg atccctcatc ctcataccca ccccaccca aggcctggc ctgagctggg      1376 atgattggag gggggaggtg ggatcctcca ggtgcacaag ctccaagctc ccaggcattc    1436 cccaggaggc cagccttgac cattctccac cttccaggga cagaggggt ggcctcccaa     1496 ctcaccccag ccccaaaact ctcctctgct gctggctggt tagaggttcc ctttgacgcc    1556 atcccagccc caatgaacaa ttatttatta aatgcccagc cccttctgaa aaaaaaaaa    1616 aaaaaaaaaa aaaaaaaaa aaaattcct gcggccgc                             1654

<210> SEQ ID NO 4
<211> LENGTH: 397
<212> TYPE: PRT
<213> ORGANISM: Homo sapiens

<400> SEQUENCE: 4

Met Ala Pro Ile Ser Leu Ser Trp Leu Leu Arg Leu Ala Thr Phe Cys
  1               5                  10                  15

His Leu Thr Val Leu Leu Ala Gly Gln His His Gly Val Thr Lys Cys
             20                  25                  30
```

```
Asn Ile Thr Cys Ser Lys Met Thr Ser Lys Ile Pro Val Ala Leu Leu
         35                  40                  45

Ile His Tyr Gln Gln Asn Gln Ala Ser Cys Gly Lys Arg Ala Ile Ile
     50                  55                  60

Leu Glu Thr Arg Gln His Arg Leu Phe Cys Ala Asp Pro Lys Glu Gln
 65                  70                  75                  80

Trp Val Lys Asp Ala Met Gln His Leu Asp Arg Gln Ala Ala Ala Leu
                 85                  90                  95

Thr Arg Asn Gly Gly Thr Phe Glu Lys Gln Ile Gly Glu Val Lys Pro
             100                 105                 110

Arg Thr Thr Pro Ala Ala Gly Gly Met Asp Glu Ser Val Val Leu Glu
         115                 120                 125

Pro Glu Ala Thr Gly Glu Ser Ser Leu Glu Pro Thr Pro Ser Ser
         130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                 165                 170                 175

Asp Gly Gly Pro Val Gly Thr Glu Leu Phe Arg Val Pro Pro Val Ser
             180                 185                 190

Thr Ala Ala Thr Trp Gln Ser Ser Ala Pro His Gln Pro Gly Pro Ser
         195                 200                 205

Leu Trp Ala Glu Ala Lys Thr Ser Glu Ala Pro Ser Thr Gln Asp Pro
         210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                 245                 250                 255

Glu Asn Ser Leu Glu Arg Glu Glu Met Gly Pro Val Pro Ala His Thr
             260                 265                 270

Asp Ala Phe Gln Asp Trp Gly Pro Gly Ser Met Ala His Val Ser Val
         275                 280                 285

Val Pro Val Ser Ser Glu Gly Thr Pro Ser Arg Glu Pro Val Ala Ser
    290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                 325                 330                 335

Ala Thr Arg Arg Gln Ala Val Gly Leu Leu Ala Phe Leu Gly Leu Leu
             340                 345                 350

Phe Cys Leu Gly Val Ala Met Phe Thr Tyr Gln Ser Leu Gln Gly Cys
         355                 360                 365

Pro Arg Lys Met Ala Gly Glu Met Ala Glu Gly Leu Arg Tyr Ile Pro
         370                 375                 380

Arg Ser Cys Gly Ser Asn Ser Tyr Val Leu Val Pro Val
385                 390                 395

<210> SEQ ID NO 5
<211> LENGTH: 15
<212> TYPE: DNA
<213> ORGANISM: Artificial Sequence
<220> FEATURE:
<223> OTHER INFORMATION: synthetic antisense

<400> SEQUENCE: 5
```
tatcggagcc atggc                                                    15

<210> SEQ ID NO 6
<211> LENGTH: 36
<212> TYPE: DNA
<213> ORGANISM: Artificial Sequence
<220> FEATURE:
<223> OTHER INFORMATION: synthetic primer

<400> SEQUENCE: 6
gggaaagaat tcctgccggg tcagcacctc ggcatg                             36

<210> SEQ ID NO 7
<211> LENGTH: 39
<212> TYPE: DNA
<213> ORGANISM: Artificial Sequence
<220> FEATURE:
<223> OTHER INFORMATION: synthetic primer

<400> SEQUENCE: 7
gggaaactcg agtcattctc aaacttgcca ccattttta                          39

<210> SEQ ID NO 8
<211> LENGTH: 17
<212> TYPE: DNA
<213> ORGANISM: Artificial Sequence
<220> FEATURE:
<223> OTHER INFORMATION: synthetic primer

<400> SEQUENCE: 8
cacagtccac ccctcag                                                  17

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
gctctggtaa gcaaacatgg                                               20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
tgtgaactcc tctggcctgt                                               20

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11 gaagggctg ggcatttaat                                                20

<210> SEQ ID NO 12
<211> LENGTH: 36
<212> TYPE: DNA

```
<213> ORGANISM: Artificial Sequence
<220> FEATURE:
<223> OTHER INFORMATION: synthetic primer

<400> SEQUENCE: 12
gggaaagaat tcatggctcc ctcgccgctc gcgtcc                               36

<210> SEQ ID NO 13
<211> LENGTH: 60
<212> TYPE: DNA
<213> ORGANISM: Artificial Sequence
<220> FEATURE:
<223> OTHER INFORMATION: synthetic primer

<400> SEQUENCE: 13
gggaaactcg agtcatttat catcatcatc tttataatcc actggcacca ggacgtatga    60

<210> SEQ ID NO 14
<211> LENGTH: 8
<212> TYPE: PRT
<213> ORGANISM: Homo sapiens

<400> SEQUENCE: 14

Asp Tyr Lys Asp Asp Asp Asp Lys
  1               5

<210> SEQ ID NO 15
<211> LENGTH: 14
<212> TYPE: PRT
<213> ORGANISM: Homo sapiens

<400> SEQUENCE: 15

Leu Pro Gly Gln His Leu Gly Met Thr Lys Cys Glu Ile Met
  1               5                  10

<210> SEQ ID NO 16
<211> LENGTH: 36
<212> TYPE: DNA
<213> ORGANISM: Artificial Sequence
<220> FEATURE:
<223> OTHER INFORMATION: synthetic primer

<400> SEQUENCE: 16
gggaaagaat tcctgccggg tcagcacctc ggcatg                               36

<210> SEQ ID NO 17
<211> LENGTH: 39
<212> TYPE: DNA
<213> ORGANISM: Artificial Sequence
<220> FEATURE:
<223> OTHER INFORMATION: synthetic primer

<400> SEQUENCE: 17
gggaaactcg agtcaccttg tggctgcctg ggtgtcggg                            39

<210> SEQ ID NO 18
<211> LENGTH: 13
<212> TYPE: PRT
<213> ORGANISM: Homo sapiens

<400> SEQUENCE: 18

His Ser Leu Gly Lys Trp Leu Gly His Pro Asp Lys Phe
  1               5                  10

<210> SEQ ID NO 19
```

```
<211> LENGTH: 9
<212> TYPE: PRT
<213> ORGANISM: Homo sapiens

<400> SEQUENCE: 19

Lys Gln Asn His His His His His His
  1               5

<210> SEQ ID NO 20
<211> LENGTH: 71
<212> TYPE: PRT
<213> ORGANISM: Mus musculus

<400> SEQUENCE: 20

Leu Ala Gly Gln His His Gly Val Thr Lys Cys Asn Ile Thr Cys Ser
  1               5                  10                  15

Lys Met Thr Ser Lys Ile Pro Val Ala Leu Leu Ile His Tyr Gln Gln
                 20                  25                  30

Asn Gln Ala Ser Cys Gly Lys Arg Ala Ile Ile Leu Glu Thr Arg Gln
             35                  40                  45

His Arg Leu Phe Cys Ala Asp Pro Lys Glu Gln Trp Val Lys Asp Ala
         50                  55                  60

Met Gln His Leu Asp Arg Gln
 65                  70
```

What is claimed is:

1. An antibody produced by the hybridoma deposited with ATCC as Accession Number HB-12555.

2. An antibody produced by the hybridoma deposited with ATCC as Accession Number HB-12556.

3. Hybridoma M7 5b1.4 deposited with ATCC as Accession Number HB-12555.

4. Hybridoma M7 5a11.5 deposited with ATCC as Accession Number HB-12556.

* * * * *